United States Patent [19]
Anderson et al.

[11] Patent Number: 5,658,133
[45] Date of Patent: Aug. 19, 1997

[54] PUMP CHAMBER BACK PRESSURE DISSIPATION APPARATUS AND METHOD

[75] Inventors: Robert L. Anderson; Daniel C. Colesworthy, III; Warren P. Heim; Larry Blankenship, all of Boulder, Colo.

[73] Assignee: Baxter International Inc., Deerfield, Ill.

[21] Appl. No.: 388,965

[22] Filed: Feb. 15, 1995

Related U.S. Application Data

[63] Continuation-in-part of Ser. No. 209,519, Mar. 9, 1994.
[51] Int. Cl.6 .................................................. F04B 49/00
[52] U.S. Cl. ........................... 417/63; 417/479; 73/19.1
[58] Field of Search .................................... 73/19.1, 64.53; 417/63, 474–477.14, 478, 479; 604/122, 123, 131

[56] References Cited

U.S. PATENT DOCUMENTS

| | | |
|---|---|---|
| 2,105,200 | 1/1938 | Phelps . |
| 2,412,397 | 12/1946 | Harper . |
| 3,701,618 | 10/1972 | Wall . |
| 3,778,195 | 12/1973 | Bamberg . |
| 3,966,358 | 6/1976 | Heimes et al. . |

(List continued on next page.)

FOREIGN PATENT DOCUMENTS

| | | |
|---|---|---|
| 0273714 | 12/1987 | European Pat. Off. . |
| 0388596 | 1/1990 | European Pat. Off. . |
| 9421918 | 9/1994 | WIPO . |

*Primary Examiner*—Timothy Thorpe
*Assistant Examiner*—Peter G. Korytnyk
*Attorney, Agent, or Firm*—F. C. Kowalik; P. E. Schaafsma; T. D. Bratschun

[57] ABSTRACT

A medical infusion pump (10) for delivering liquids to a patient includes an elastomeric pump chamber (140) contractable between a refill position and a discharge position. An inlet valve (122) is operatively associated with an elastomeric inlet (142) supplying liquid to the pump chamber (140). The inlet valve (122) is selectively positionable in an open position permitting and a closed position preventing flow of liquid between the inlet (142) and the pump chamber (142). An outlet valve (124) is operatively associated with an elastomeric outlet (144) which conveys liquid from the pump chamber (140). The outlet valve (124) is selectively positionable in an open position permitting and a closed position preventing flow of liquid between the outlet (144) and pump chamber (140). A pump motor (256) and associated plunger (120) contracts and expands the pump chamber (140) between the refill position and the discharge position. An electronic control (542) operatively associated with the pump motor (256) and plunger (120) and the inlet and outlet (122, 124) valves actuates the pump motor (256) and the inlet and outlet valves (122, 124) to drive liquid through the pump chamber (140) in a predetermined pumping cycle. The electronic control (542) includes a routine for dissipating ballooning in the pump chamber (140), the inlet (142) or the outlet (144) by delaying movement of the pump motor (256) with the pump chamber (140) in the contracted position and the outlet valve (124) in the open position a select amount of time.

6 Claims, 40 Drawing Sheets

U.S. PATENT DOCUMENTS

| | | | |
|---|---|---|---|
| 4,199,307 | 4/1980 | Jassawalla . | |
| 4,255,088 | 3/1981 | Newton et al. . | |
| 4,273,121 | 6/1981 | Jassawalla . | |
| 4,373,527 | 2/1983 | Fischell . | |
| 4,396,385 | 8/1983 | Kelly et al. . | |
| 4,411,652 | 10/1983 | Kramer et al. . | |
| 4,416,595 | 11/1983 | Cromie . | |
| 4,425,116 | 1/1984 | Bilstad et al. . | |
| 4,428,745 | 1/1984 | Williams . | |
| 4,456,009 | 6/1984 | Vcelka et al. . | |
| 4,460,358 | 7/1984 | Somerville et al. . | |
| 4,474,309 | 10/1984 | Solomon . | |
| 4,479,797 | 10/1984 | Kobayashi et al. . | |
| 4,498,843 | 2/1985 | Schneider et al. . | |
| 4,515,536 | 5/1985 | van Os . | |
| 4,551,133 | 11/1985 | Zegers de Beyl et al. . | |
| 4,586,691 | 5/1986 | Kozlow . | |
| 4,650,469 | 3/1987 | Berg et al. . | |
| 4,657,490 | 4/1987 | Abbott . | |
| 4,689,043 | 8/1987 | Bisha . | |
| 4,690,673 | 9/1987 | Bloomquist . | |
| 4,696,671 | 9/1987 | Epstein et al. . | |
| 4,731,051 | 3/1988 | Fischell . | |
| 4,735,558 | 4/1988 | Kienholz et al. . | |
| 4,764,166 | 8/1988 | Spani | 604/65 |
| 4,784,645 | 11/1988 | Fischell . | |
| 4,810,243 | 3/1989 | Howsen . | |
| 4,818,186 | 4/1989 | Pastrone et al. | 417/63 |
| 4,821,558 | 4/1989 | Pastrone et al. . | |
| 4,842,584 | 6/1989 | Pastrone . | |
| 4,893,991 | 1/1990 | Heminway et al. . | |
| 4,927,411 | 5/1990 | Pastrone et al. . | |
| 4,944,191 | 7/1990 | Pastrone et al. . | |
| 4,954,055 | 9/1990 | Raible et al. . | |
| 5,000,663 | 3/1991 | Gorton | 417/63 |
| 5,000,664 | 3/1991 | Lawless | 417/63 |
| 5,006,050 | 4/1991 | Cooke et al. . | |
| 5,006,110 | 4/1991 | Garrison et al. | 604/65 |
| 5,017,059 | 5/1991 | Davis . | |
| 5,039,279 | 8/1991 | Natwick et al. . | |
| 5,074,756 | 12/1991 | Davis . | |
| 5,088,522 | 2/1992 | Rath et al. . | |
| 5,088,981 | 2/1992 | Howsen et al. . | |
| 5,100,380 | 3/1992 | Epstein et al. . | |
| 5,116,203 | 5/1992 | Natwick et al. . | |
| 5,131,816 | 7/1992 | Brown et al. . | |
| 5,153,827 | 10/1992 | Coutre et al. . | |
| 5,158,437 | 10/1992 | Natwick . | |
| 5,166,203 | 11/1992 | Natwick et al. . | |
| 5,180,287 | 1/1993 | Natwick et al. | 417/53 |
| 5,191,795 | 3/1993 | Fellingham et al. . | |
| 5,211,548 | 5/1993 | Okada . | |
| 5,242,279 | 9/1993 | Knuth . | |
| 5,252,044 | 10/1993 | Raines et al. . | |
| 5,273,406 | 12/1993 | Feygin . | |
| 5,290,239 | 3/1994 | Classey et al. . | |
| 5,336,051 | 8/1994 | Tamari . | |
| 5,482,446 | 1/1996 | Williamson et al. | 417/474 |
| 5,551,850 | 9/1996 | Williamson et al. | 417/474 |

Fig. 38

| | | FLUID DELIVERY MODES | | |
|---|---|---|---|---|
| MODE 1 | MODE 2 | MODE 3 | MODE 4 | MODE 5 |
| 0.1 - 0.4 mL/HR | 0.5 - 7.9 mL/HR | 8 - 49.9 mL/HR | 50 - 249 mL/HR | 250-390 mL/HR |
| 20 -180 SEC/DELIVERY | 1.82 - 18 SEC/DELIVERY | 1.1 - 9 SEC/DELIVERY | 1.8 - 5.6 SEC/DELIVERY | 1.1 - 1.8 SEC/DELIVERY |
| CLOSE DISTAL VALVE EACH DELIVERY  50µL STROKE | DELIVER IN 5 µL INCREMENTS | DELIVER IN 25 µL INCREMENTS | DELIVER IN 125 µL INCREMENTS | |
| | DELIVERY FIRST FLUID INCREMENT BEFORE FILL TEST | | | |
| DWELL BETWEEN VALVE CLOSURES | | | NO RETRACT ON FILL TEST | |
| REFILL COMPENSATION | | | | CONCURRENT MOTOR OPERATIONS |

PUMP CHAMBER BACK PRESSURE DISSIPATION APPARATUS AND METHOD

This is a continuation-in-part of copending application Ser. No. 08/209,519 filed on Mar. 9, 1994 now allowed.

BACKGROUND OF THE INVENTION

The present invention is directed toward an ambulatory infusion pump and, more particularly, toward a programmable ambulatory infusion pump including a routine for dissipating pump back pressure.

BACKGROUND ART

Spiraling health care costs have led to the development of a variety of devices for facilitating administration of intravenous therapy to patients outside of a clinical setting. In addition, doctors have found that in many instances patients can return to substantially normal lives, provided that they can receive continuous intravenous administration of medication. These factors have combined to promote the development of lightweight, portable or ambulatory infusion pumps which can be worn by a patient and are capable of administering a continuous supply of medication at a desired rate.

A wide variety of ambulatory pumps in use in the medical field are intended to meet the need of a high degree of accuracy in the administration of fluids to maximize the effectiveness of medication and to protect the patient. Typically, these ambulatory infusion pumps include a pump control unit and drive mechanism including a variety of operating controls adapted to accept a disposable pump chamber assembly. One known pumping mechanism includes inlet and outlet valves and a single liquid displacement plunger, and will be referred to herein as a single plunger, two valve pump. Each pumping cycle in this type of pump begins with the outlet valve closed and the inlet valve open. Fluid flows from a source container into a section of elastomeric tubing disposed between the inlet and outlet valve. After this section of tubing has filled with liquid, the inlet valve closes and the outlet valve opens. The plunger then compresses the short section of tubing between the valves, displacing the liquid contained therein and forcing it through the pump. The outlet valve then closes and the pump cycle is ready to repeat itself.

Such known pumping mechanisms have proven to provide sufficiently accurate fluid delivery over a relatively narrow range of flow rates. With ever evolving therapies requiring increasingly disparate infusion rates, this relatively narrow range of accurate flow rates is no longer sufficient for a true multi-therapy pump. As a result, health care providers must maintain on hand numerous pumps having infusion rates within different relatively narrow range to meet the requirements of various therapies.

Many therapies require administration of precise drug dosages to assure an effective, safe treatment. Maintaining a precise pump output from single plunger, two valve pumps has proven difficult. One problem with such pumps is that at high pump rates the plunger may compress the elastomeric tubing faster than liquid can be expelled from the outlet or distal valve. This problem occurs most often when a distal line extending from the elastomeric tubing is connected to a small internal diameter tubing such as a PIC catheter. As a result of this problem, a back pressure develops in the distal line and elastomeric tube causing expansion or ballooning of the distal line and elastomeric tube, which results in degradation of pump accuracy.

In administering intravenous fluids to patients it is important to monitor the fluid being administered to prevent infusion of air to a patient. Not only can the presence of air degrade pump accuracy, excessive air could cause an embolism. Air may be introduced into the system through a leak in a tube connector, through a crack in a tube, or through air present in an IV container. Pastrone et al., U.S. Pat. No. 4,944,191 attempts to overcome the serious shortcomings of prior art optical detectors through the use of an ultrasonic air detect. In particular, Pastrone et al. attempts to overcome a problem of false air-in-line signals resulting from optical air detectors. However, even the ultrasonic air detect disclosed by Pastrone et al. is subject to false air-in-line signals. False signals are a significant problem because they cause shutdown of the pump. If a clinician finds the number of false signals is disrupting treatment, the clinician may be tempted to disable the air detect, placing the patient at serious risk of improper drug dosages or an embolism.

Prior art air detectors, including ultrasonic air detects, are also deficient in that they are designed only to detect whether a single bubble of greater than a select size is present in the line. If multiple bubbles of less than a select size are present, they may go undetected, notwithstanding that they may join downstream of the air detect, creating a potential for a harmful embolism. Even without joining, multiple air bubbles which escape detection degrade pump accuracy.

The present invention is directed toward overcoming one or more of the problems discussed above.

SUMMARY OF THE INVENTION

One aspect of the present invention is a medical infusion pump for delivering liquids to a patient. The infusion pump includes an elastomeric pump chamber contractible between a refill position and a discharge position. An inlet valve is operatively associated with an elastomeric inlet supplying liquid to the pump chamber. The inlet valve is selectively positionable in an open position permitting, and a closed position preventing, flow of liquid between the inlet and the pump chamber. An outlet valve is operatively associated with an elastomeric outlet which conveys liquid from the pump chamber. The outlet valve is selectively positionable in an open position permitting, and a closed position preventing, flow of liquid between the outlet and pump chamber. A pump motor and associated plunger contracts and expands the pump chamber between the refill position and the discharge position. An electronic control operatively associated with the pump motor and plunger and the first and second valves actuates the pump motor and the first and second valves to drive liquid through the pump chamber in a predetermined pumping cycle. The electronic control includes a routine for dissipating ballooning in the pump chamber, the inlet or the outlet by delaying movement of the pump motor with the pump chamber in the contracted position and the outlet valve in the open position a select amount of time. The select amount of time is calculated using the following equation: Select amount of time=½ $(T_1-T_2)$, where $T_1$ is the time required for the pumping operation in order to satisfy pump rate requirements and $T_2$ is the time to execute the pumping operation.

A second aspect of the present invention is a method of delivering liquid through a medical infusion pump to a patient where the medical infusion pump includes an elastomeric pump chamber contractible between a first position and a second position, an elastomeric inlet for supplying liquid to the pump chamber and an elastomeric outlet for conveying liquid from the pump chamber. An inlet valve is operatively associated with the inlet for selective positioning in an open position permitting, and a closed position preventing, flow of liquid between the inlet and the pump chamber. An outlet valve is operatively associated with the outlet for selective positioning in an open position permitting, and a closed position preventing, flow of liquid between the outlet and the pump chamber. A pump motor and associated plunger are provided for expanding and contracting the pump chamber between the first position and the second position. The method includes beginning with the pump chamber at the first position, the inlet valve in the closed position and the outlet valve in the open position. The pump chamber is contracted to the second position at a rate faster than liquid can be discharged through the distal line so as to cause ballooning in the pump chamber, the inlet or the outlet. The pump chamber is then maintained in the second position a select amount of time to allow for dissipation of ballooning in the pump chamber, inlet means or outlet means. Next, the outlet valve is positioned in the closed position following which the inlet valve is positioned in the open position. The pump chamber is then positioned in the first position, wherein the sequence of steps can be repeated.

A third aspect of the present invention is an apparatus for detecting an excessive concentration of air in a liquid flow through a conduit. The apparatus includes an ultrasonic sound generator and an ultrasonic receiver spaced from one another to receive a detection portion of liquid conveying conduit therebetween. The ultrasonic receiver detects whether the sound received from the generator is indicative of air or liquid within the conduit and outputs an "air" signal if air is indicated. An actuator periodically actuates the ultrasonic sound generator to generate a sound upon a first select incremental volume of liquid entering and a second select incremental volume leaving the detection portion of the conduit. An electronic control receives the air signal from the receiver and counts the air signals over a select time period to determine whether the number of air signals in the select time period exceeds a first select number and outputs an alarm signal if the select number is exceeded.

The apparatus and method of the present invention provides significantly improved accuracy over prior art one plunger, two valve pumps. By delaying the pump sequence with the plunger extended and the outlet valve open, ballooning of the pump chamber, inlet or outlet is allowed to dissipate thereby providing for more complete discharge of the pump chamber. The period of delay with the pump chamber contracted and the outlet valve open is calculated so as to maximize the time the chamber is contracted and the outlet valve is open during each pump cycle while avoiding interference with the pumping rate. Thus, pump accuracy is improved while the pumping rate is not affected. The air detect apparatus for an infusion pump of the present invention continuously monitors liquid as it is administered to a patient to prevent infusion of air to a patient and to verify any air being administered to the patient is not sufficient to degrade pump accuracy or harm the patient. By summing the air signals over a select time period and determining whether the sum exceeds a select number, the ultrasonic air detect apparatus minimizes false air-in-line signals. In addition, by making numerous air-in-line determinations during a select period of time as opposed to a larger snapshot of the liquid flowing through the conduit, the present invention can detect numerous smaller bubbles which might go undetected under prior art structures which, in combination, present a danger of degrading pump accuracy or creating an embolism.

BRIEF DESCRIPTION OF THE DRAWINGS

FIG. 38 is a table summarizing pump operation during the four fluid delivery modes;

DETAILED DESCRIPTION OF THE PREFERRED EMBODIMENT

Figure 1:
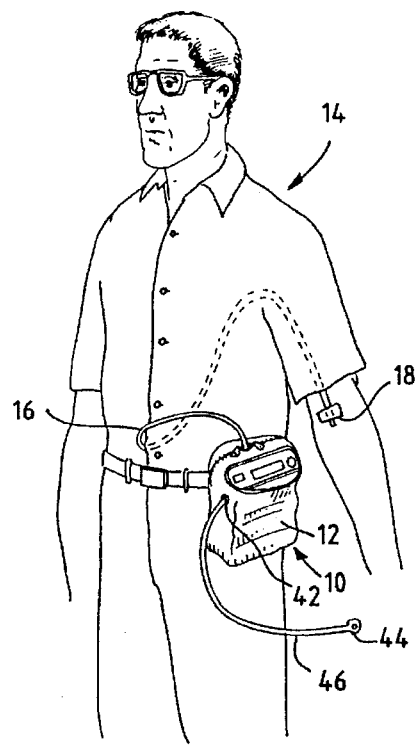
FIG. 1 is a perspective view of a patient wearing an ambulatory infusion pump of the present invention.

FIG. 1 illustrates an ambulatory infusion pump 10 contained within a soft pump case 12 mounted to an ambulatory patient 14. The ambulatory infusion pump 10 is designed to provide a wide variety of drug delivery profiles so that a wide variety of therapies can be administered by the ambulatory infusion pump. The compact size and light weight of the pump facilitate a patient wearing the pump so that a continuous supply of medication can be delivered to the patient while the patient can engage in normal everyday activities. A flexible IV tube 16, which typically is made of PVC, extends between the pump 10 and a needle/catheter 18 for intravenous infusion of medication from the pump to the ambulatory patient. The ambulatory infusion pump 10 is usable in other applications where the distal end of the IV tube is connected to some other apparatus disposed downstream of the pump 10.

A. Pump Housing

Figure 2:
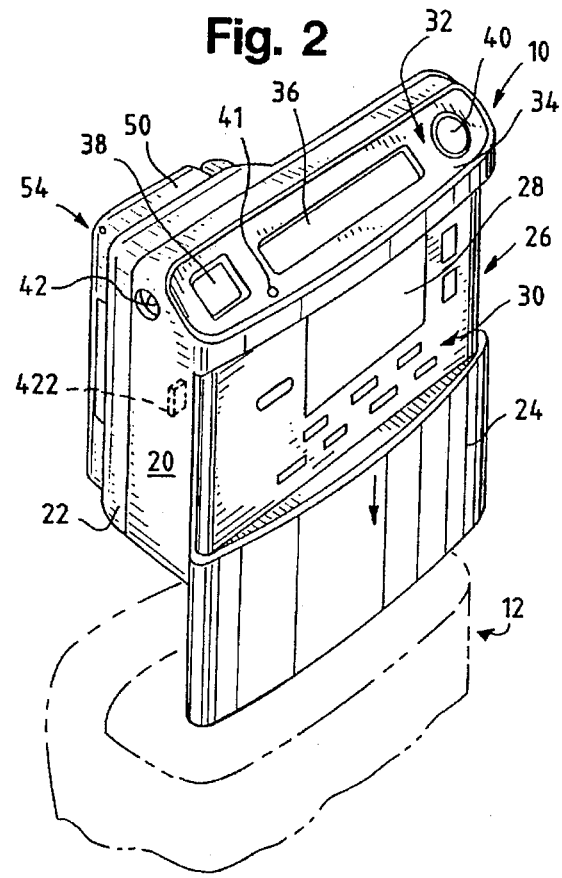
FIG. 2 is a perspective view of the ambulatory infusion pump with the front cover slid to an open position.
Figure 3:
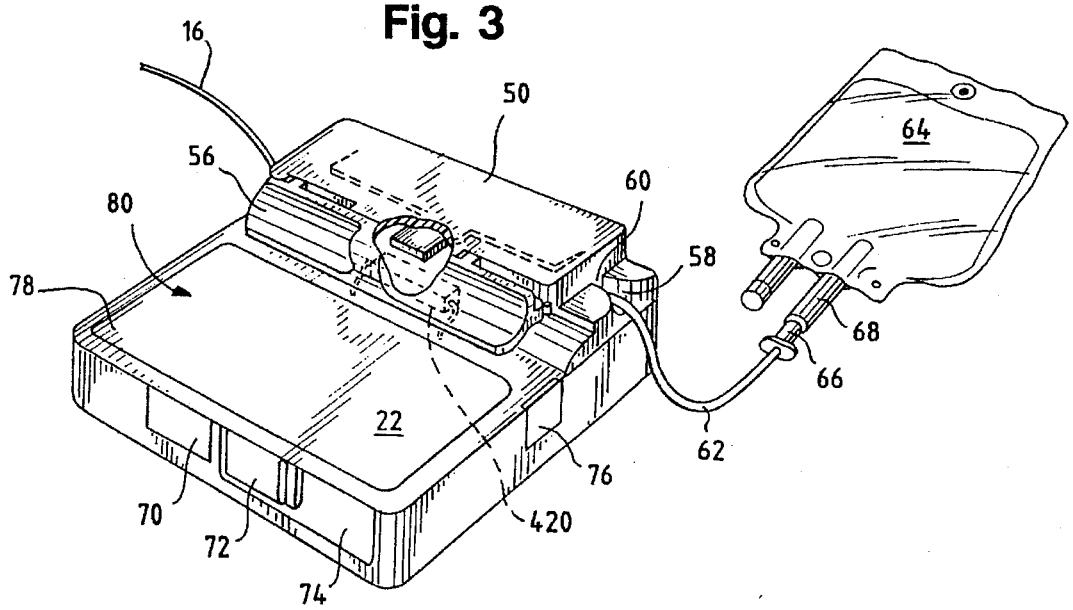
FIG. 3 is a perspective view of the back of the ambulatory infusion pump with a solution bag in fluid communication with a pump cassette loaded into the ambulatory infusion pump.

The pump housing is designed for ease of patient and clinician use as well as patient comfort when the ambulatory pump 10 is worn. FIGS. 2 and 3 illustrate the pump housing. The ambulatory infusion pump 10 includes a rigid housing front 20 and a rigid housing back 22 which are preferably made of a high density rigid polymer such as polycarbonate and are joined by a continuous tongue and groove interface around their peripheries. A front cover 24 is slidably mounted to the rigid front housing 20 to selectively cover and uncover a control panel 26 on the rigid housing front 20. The control panel 26 includes an LCD programmer display 28 and a keyboard 30. The front cover 24 therefore protects and conceals the control panel to prevent inadvertent actuation of the keyboard 30. Detents (not shown) may be provided on the front cover 24 to maintain the front cover in a position covering or not covering the control panel 26. The keyboard 30 are membrane switch panels. A user control panel 32 is located on a beveled front surface 34 of the rigid housing front 20. The user control panel 32 includes a patient display 36, a start/stop button 38 and a bolus dose control button 40. An LED 41 is provided on the user control panel 32 for providing a visual alarm or alert. Also on the rigid housing front 20 is a remote bolus switch contact 42 to which a remote bolus switch 44 can be coupled by means of electrical contact wire 46 (see FIG. 1). The pump is programmable so that a patient may use the bolus dose control button 40 or the remote bolus switch 44 to self-administer a bolus of medication, as for example in patient-controlled analgesic (PCA) therapies. Programming of the pump 10 will be discussed in greater detail below.

The rigid housing back 22 is best illustrated in FIG. 3. A cassette door 50 made of a rigid polymer such as glass-filled polycarbonate is pivotably attached to the rigid housing back 22 by a pair of hinges 52,54 (see FIGS. 4 and 5). A latch 56 is slidably mounted to the rigid housing back 22 to selectively capture and release the cassette door 50 in a manner which will be discussed in detail below. A channel 58 in the rigid housing back 22 cooperates with a hemispherical slot 60 in the cassette door 50 to define a passage for receiving the IV tubing 62 in fluid communication with a fluid supply such as a solution bag 64. As illustrated in FIG. 3, the flexible tubing 62 is brought into fluid communication with the solution bag 64 by means of a spike 66 received in the solution bag outlet 68.

As seen in FIG. 3, between the rigid housing front 20 and the rigid housing back 22 is an infrared or IR window 70 made of molded tinted plastic which allows transmission of an IR signal to and from the ambulatory infusion pump 10.

A sliding battery door 72 permits access to a cavity 74 which receives a 9 V battery (not shown) to provide electric power to the ambulatory infusion pump 10. An on/off switch 76 to power "on" or "off" the ambulatory infusion pump 10 is also provided. A rear panel 78 on the rigid housing back 22 bears an instruction label 80 consisting of an adhesive coated polyester. The polyester instruction label 80 also functions to cover mechanical access holes in the rigid housing back 22 so as to provide a moisture barrier.

Figures 4, 5:
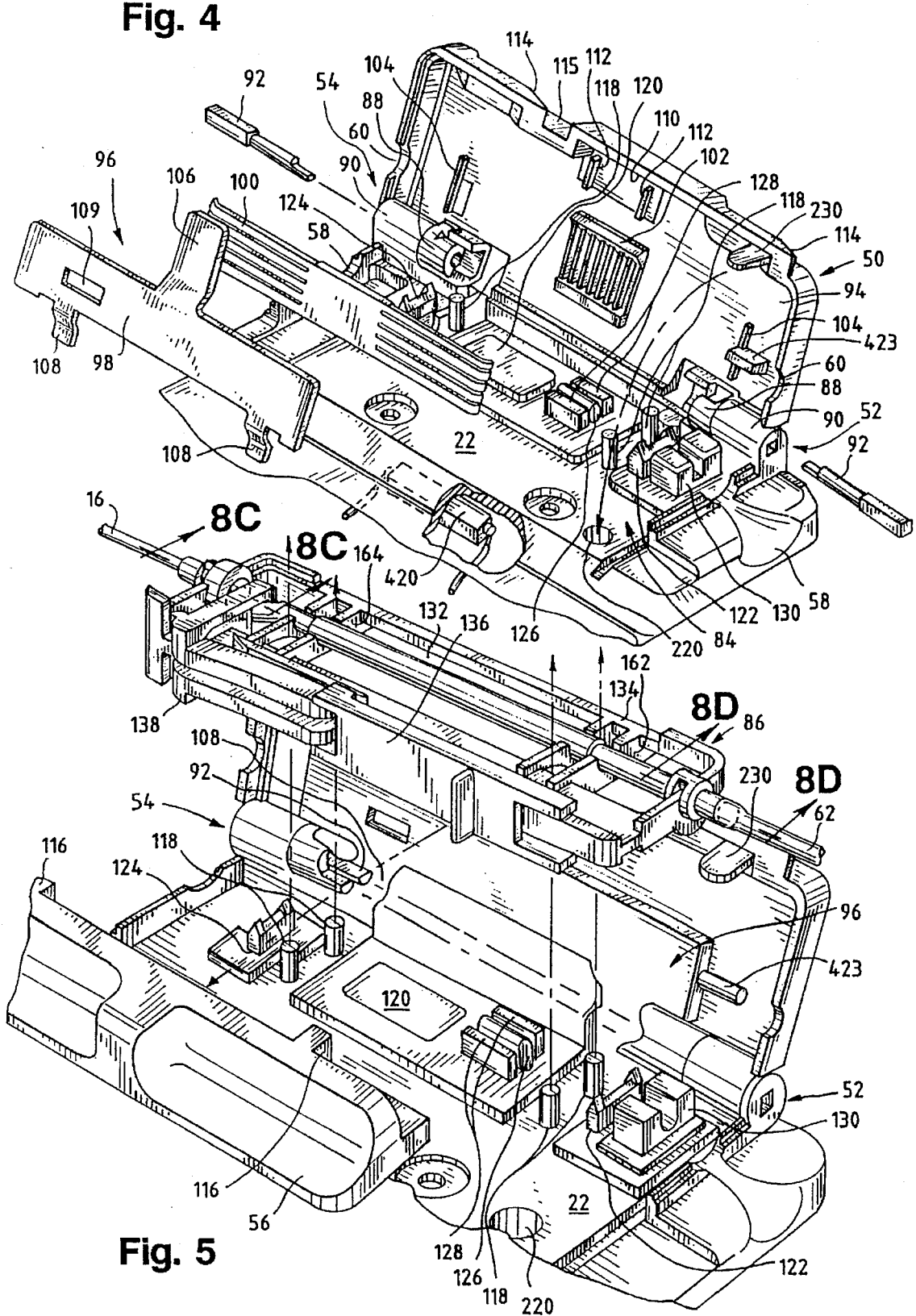
FIG. 4 is an exploded perspective view of the pump cassette receptacle of the ambulatory infusion pump.
FIG. 5 is a perspective view of the pump cassette receptacle and a pump cassette illustrating loading of the pump cassette into the pump cassette receptacle.

FIGS. 4 and 5 illustrates a portion of the rigid housing back 22 including the cassette door 50 pivoted open about the hinges 52,54 to reveal a pump cassette receptacle 84 for receiving a pump cassette 86 in a manner discussed below. As seen in FIG. 4, the cassette door 50 has a pair of hinge knuckles 88 laterally spaced from one another. The hinge knuckles 88 are received between a pair of hinge knuckles 90 on the rigid housing back 22. A pair of hinge pins 92 are received within lengthwise holes in the hinge knuckles 88,90 to pivotably secure the cassette door 50 to the rigid housing back 22.

The cassette door 50 defines an inner recess 94 which contains a floating platen assembly 96. The floating platen assembly 96 consists of a rigid metal platen 98 which is biased away from the cassette door 50 by a plurality of leaf springs 100 in lengthwise side-by-side relation. The leaf springs 100 are received between a lateral leaf spring bracket 102 and a pair of longitudinal leaf spring brackets 104 integrally formed with and extending from the door 50 which selectively restrain the leaf springs 100 from lateral or lengthwise movement relative to the cassette door 50. In the preferred embodiment, only four leaf springs are required for proper pump operation, although five are provided to provide a margin of safety in the event one of the springs fails.

The platen 98 has a tab 106, a pair of hinge hooks 108 and a lengthwise hole 109. The tab 106 is received within a cavity 110 in the inner recess 94 of the cassette door 50 and secured against lengthwise movement by a pair of posts 112. The hinge hooks 108 captively receive the hinge pins 92 in the manner best illustrated in FIG. 5 both to secure the platen 98 within the inner recess 94 and to confine the leaf springs 100 within the inner recess 94.

The cassette door 50 further includes at its front a pair of spaced lateral cam surfaces 114 each having a gap 115 at the bottom of the cam surface. A complementary pair of engagement pins 116 on the latch 56 are configured to engage the lateral cam surfaces 114 and drive the cassette door 50 toward the pump cassette receptacle 84 as the latch is moved from right to left, as viewed in FIGS. 6 and 7, and to hold the cassette door 50 shut.

Extending into the pump cassette receptacle 84 through the rigid housing back 22 are four registration pins 118, a plunger 120, an inlet valve pincher 122, an outlet valve pincher 124, a pressure transducer button wedge 126 having an arcuate leading edge 127 received between a pair of guide posts 128 and an ultrasonic air detector 130. The registration pins 118 are made of a rigid material such as aluminum or steel and the plunger 120, the inlet and outlet valve pinchers 122,124 and pressure transducer button wedge 126 are preferably made of self-lubricating polymer to minimize potential binding and to maximize cleanability. At opposite ends of the leading edge of the inlet and outlet pincher valves are a pair of stops 131 (see FIGS. 9–11A).

The registration pins 118 are configured to engage the platen 98 and drives it against the bias of the leaf springs 100 into the inner recess 94 so as to position the platen 98 a select distance from the plunger 120 for reasons which will be discussed in greater detail below.

B. Pump Cassette

As seen in FIGS. 5–8D the pump cassette 86 includes an elastomeric conduit or a pump chamber assembly 132, a rigid frame 134, a slider 136 and a pincher 138 which are snap fit together. The pump cassette 86 facilitates quick and easy positioning of the pump chamber assembly 132 relative to plunger 120 and inlet and outlet valve pinchers 122,124 as well as an anti-free flow structure.

Figure 8A:
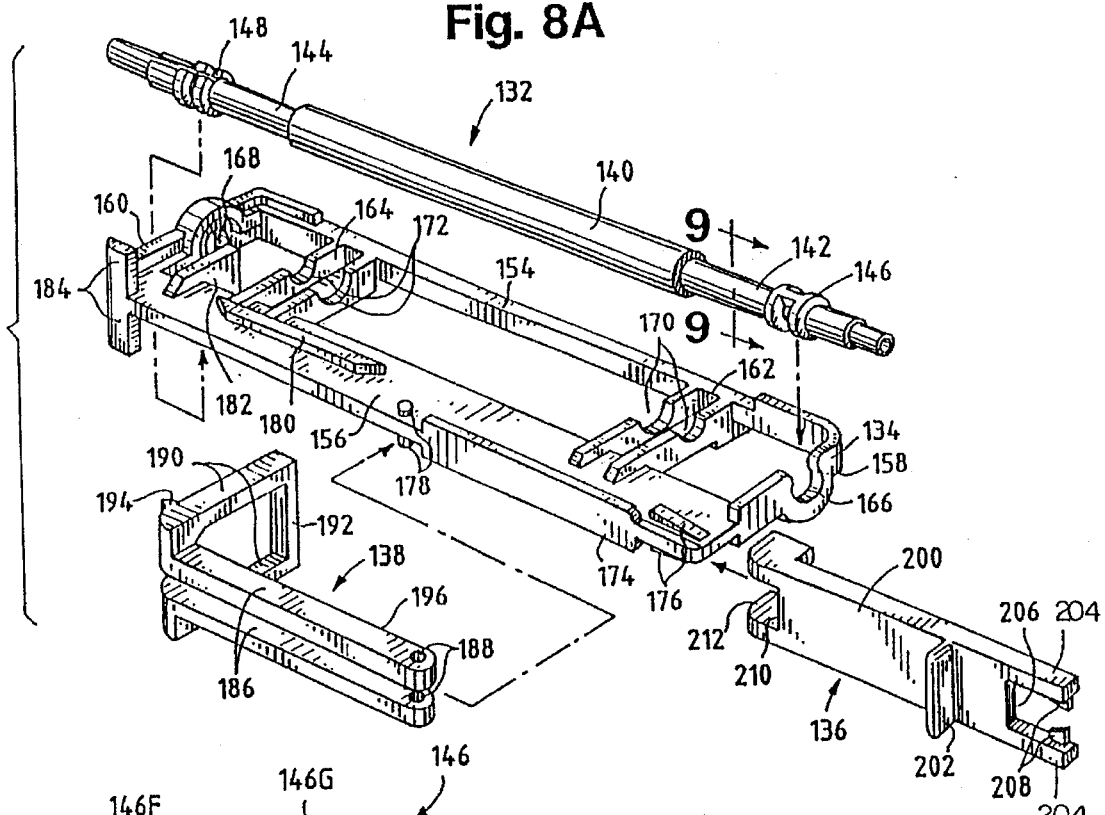
FIG. 8A is an exploded perspective view of the pump cassette.

Referring to FIG. 8A the elastomeric conduit or pump chamber assembly 132 consists of a pump chamber 140 made of polyurethane tubing, an inlet valve tube or adaptor 142 and an outlet valve tube or adaptor 144 both made of low durometer polyvinylchloride (PVC), and identical inlet and outlet clips 146,148. Polyurethane was selected for the pump chamber because of its ability to rebound and its stiffness. Low durometer PVC was selected for the inlet and outlet valve tubes because it requires relatively little energy to compress so as to completely occlude the inlet and outlet valve tubes. These material properties combine to optimize the pump chamber assembly 132 operation and to minimize battery power required to pump fluid through the pump chamber assembly 132.

The polyurethane pump chamber 140 exhibits greater rebound than PVC tubing typically used in ambulatory infusion pumps. The ability to rebound is particularly important with respect to the pump chamber because the pumping mechanism relies upon the resilience of the pump chamber material to return the pump chamber to an uncompressed state, thereby creating a negative pressure for refill of the pump chamber. The refill cycle is the limiting factor in the pumping sequence for volume output. If the material does not return to its natural state quickly enough, then the pump chamber will be underfilled, causing a decrease in volumetric output which degrades pump accuracy. As a result, the pump chamber 140 resists "ballooning" with an increased back pressure which could affect output volumes and thus the accuracy of the pump. "Ballooning" refers to a condition where extension of the plunger into the pump chamber causes the non-compressed portion of the pump chamber to elastically expand, thereby resulting in a volume of liquid discharged from the pump chamber which is less than the volume of liquid displaced by the plunger. To compensate for the stiffer material and the increased energy required to compress the stiff pump chamber, wall thickness of the tubing has been minimized. In the illustrated embodiment, the polyurethane pump chamber 140 has a durometer of 80 Shore A, an inner diameter of 0.157 inches and an outer diameter of 0.193 inches. Polyurethane has the additional advantage of being readily solvent bonded to a variety of materials, including PVC.

The rebound of an elastomer is measured by its tan $\Delta$, which is defined as the viscous response divided by the elastic response of the material at a select temperature. The smaller the tan $\Delta$ the greater the rebound propensity. A desirable material for a pump chamber has a tan $\Delta$ which remains relatively low through the range of operating temperatures. For the present invention, the range of operating temperatures is between approximately 32°–110° F. (0°–45° C.).

Figure 42:
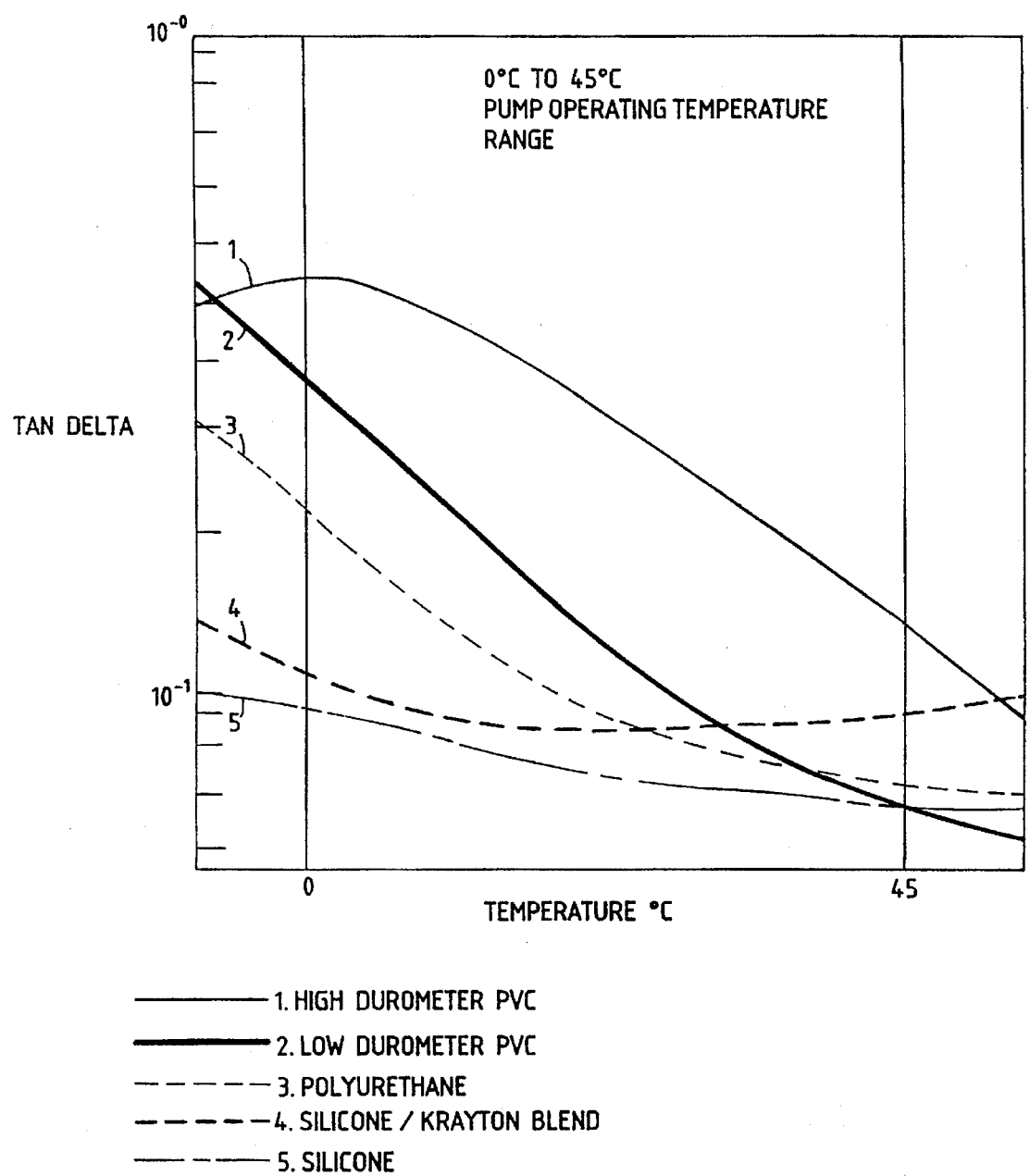
FIG. 42 is a graph of DMA tan Δ of a variety of pump tubing materials.

FIG. 42 is a graph of Dynamic Mechanical Analysis ("DMA") tan $\Delta$ versus temperature for a number of materials. PVC tubing is commonly used with peristaltic type pumps. Over the range of operating temperatures, DMA tan $\Delta$ of a low durometer PVC varies between about 0.4–0.07 and the DMA tan $\Delta$ of a high durometer PVC varies between about 0.4 to 0.2. As can be seen in FIG. 42, the DMA tan $\Delta$ of polyurethane ranges between about 0.20–0.08. Thus, polyurethane has a lower tan Δ than the tested PVC's over the range of operating temperatures.

In order to ensure a constant output volume, material stiffness should remain relatively constant over the range of operating temperatures. A constant stiffness provides a constant energy requirement for compressing the tubing over the range of operating temperatures and also ensures that the stiffness required to resist "ballooning" over the range of operating temperatures is maintained.

Figure 43:
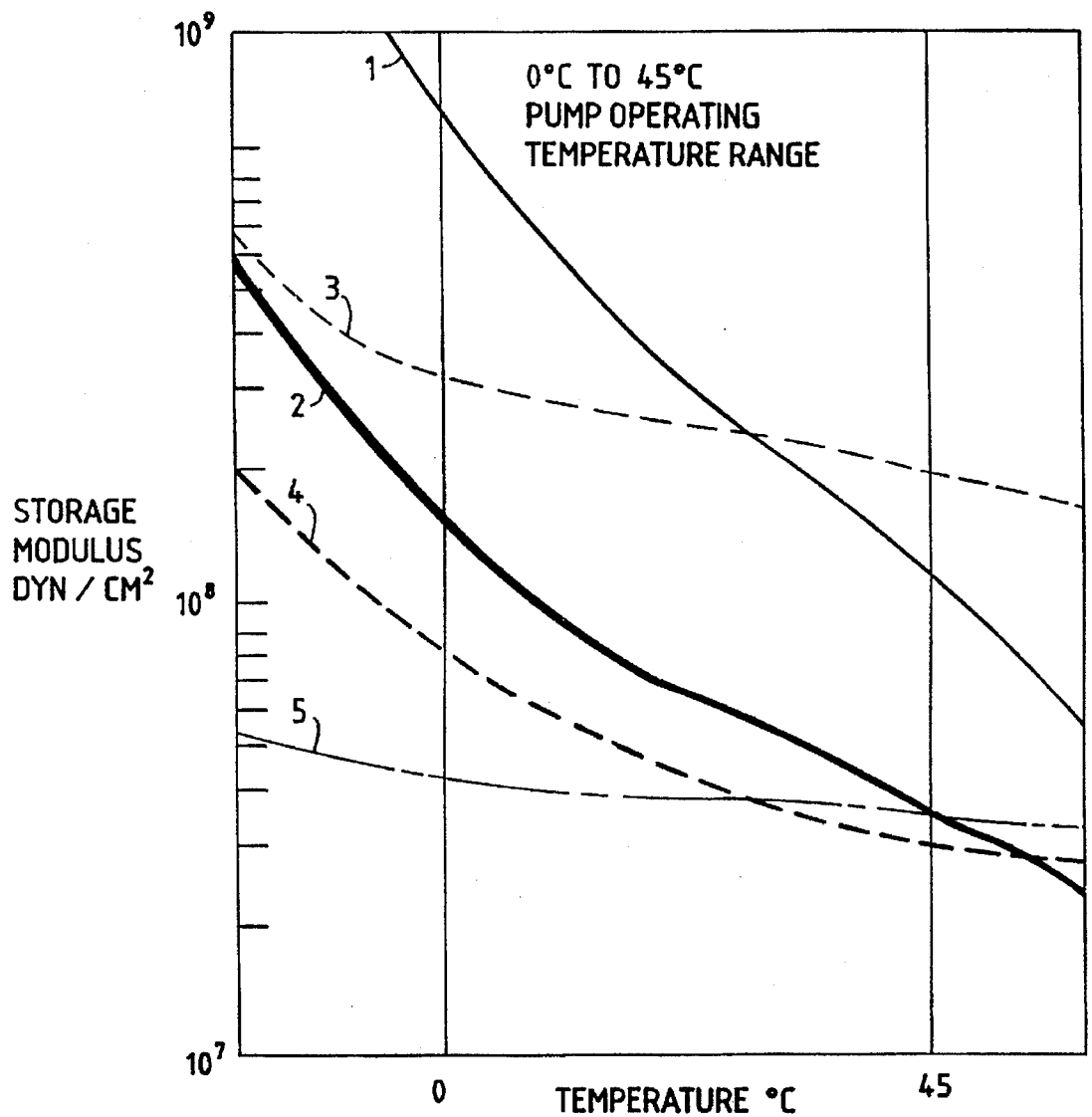
FIG. 43 is a graph of DMA stiffness of a variety of pump tubing materials.

As appreciated by those skilled in the art, "stiffness" is a function of storage modulus and tube geometry. FIG. 43 is a graph of DMA storage modulus of pump tubing versus temperature for five materials. As seen in FIG. 43, polyurethane has a relatively constant storage modulus of $10^8$ dyne/cm$^2$ over the range of operating temperatures, meaning it will have a relatively constant stiffness.

It can be observed from the tables that silicone has the desirable features of a relatively constant storage modulus or stiffness and a relatively low tan Δ over the range of operating temperatures. However, silicone is extremely difficult to solvent bond to other materials, and therefore is not suitable for use as a pump chamber with the present invention which requires a bond between the pump chamber 140 and the PVC inlet and outlet valve tubes 142, 144, so as to provide pump chamber and valve tube materials which optimize pump performance.

The inlet valve tube 142 and outlet valve tube 144 each have a lesser inner and outer diameter than the pump chamber 140. As illustrated in FIG. 8A, the inlet valve tube 142 and outlet valve tube 144 are telescopically received within the opposite ends of the inner diameter of the pump chamber 140 and are solvent bonded thereto. The inlet and outlet valve tubes 142,144 are preferably made of a PVC having a durometer between 30 and 60 shore A, with a durometer of 50 shore A being preferred. Relatively thick walls and a lower durometer are preferred to lessen the energy required to pinch off the lumens of the inlet and outlet valve tubes 142,144. In the illustrated embodiment, the inlet and outlet valve tubes 142,144 have an outer diameter of about 0.163 inches and an inner diameter of about 0.083 inches.

Other elastomers which are chemically inert with respect to fluids to be delivered by the pump and which have similar physical characteristics to the polyurethane pump chamber 140 and the low durometer PVC inlet and outlet valve tubes may be suitable substitutes for these materials, and are considered to be within the scope of the invention.

Figure 9:
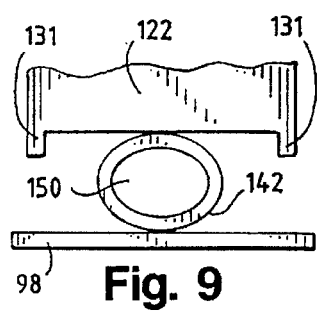
FIG. 9 is a sectional view of the inlet valve tube taken along line 9—9 of FIG. 8.
Figure 10:
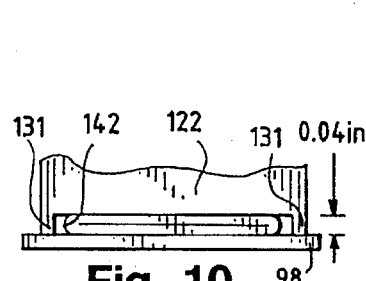
FIG. 10 is the inlet valve tube of FIG. 9 in a compressed state.
Figure 11B:
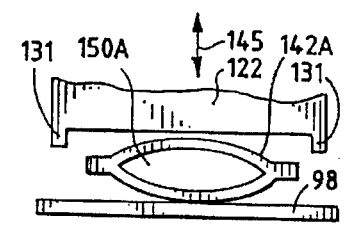
FIG. 11B is a section view of the alternative embodiment of the inlet valve tube taken along line 11B—11B of FIG. 11A including the platen and inlet pincher valve.

FIG. 9 illustrates a cross-section of the inlet valve tube 142 sandwiched between the inlet valve pincher 122 and the platen 98. The outlet valve tube 144 is identical and will not be separately discussed. During operation of the pump, the inlet valve tube 142 is repeatedly compressed to completely occlude the lumen 150, as illustrated in FIG. 10, and released to return to the partially deformed configuration shown in FIG. 9. Low durometer material is chosen for the inlet and outlet valve tubes to minimize the amount of energy required to fully close the lumen 150.

Figure 11A:
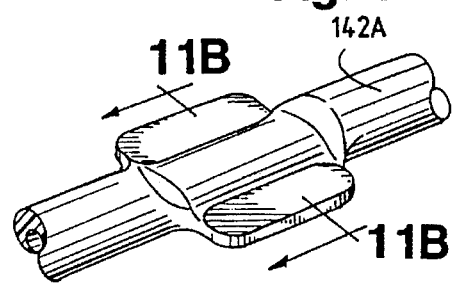
FIG. 11A is a perspective view of an alternative embodiment of the inlet valve tube.

FIG. 11A illustrates an alternative embodiment of the inlet valve tube 142A with a deformed portion 143 intended to lie between the inlet pincher valve 122 and the platen 98. The deformed portion 143 has a football-shaped cross-section 150A, as best viewed in FIG. 11B. This shape removes the vertical wall of the tubing 142A which must be crushed during the closure of the tubing. The tubing 142A is mounted within the frame 134 with the minor axis aligned parallel to the directions of movement illustrated by arrow 145 between the valve pincher 122 and the platen 98. Thus, the inlet valve tube embodiment 142A illustrated in FIGS. 11A and 11B further minimizes the energy required to occlude the lumen 150A. The inlet valve tube 142 or 142A is extruded or molded using conventional techniques. For example, standard tubing can be deformed by any known process such as RF welding, ultrasonic or pressure forming. The outlet valve tube 144 may be identical to the alternate embodiment of the inlet valve tube 142A and will not be separately described.

Figure 7:
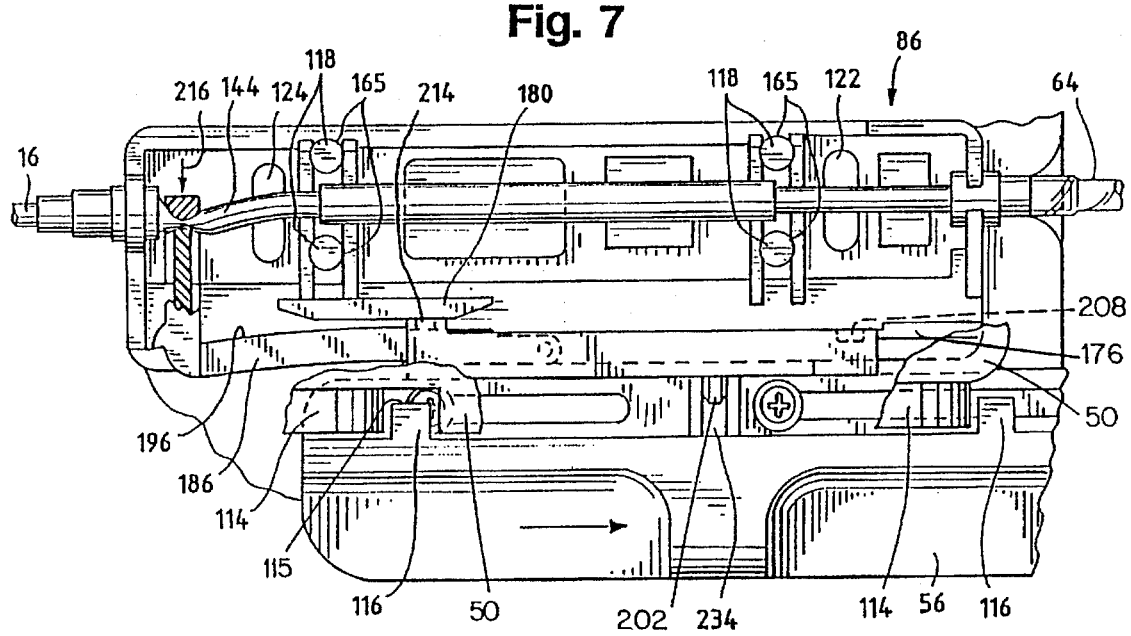
FIG. 7 differs from FIG. 6 only in that the latch is in an "open" position.
Figure 8B:
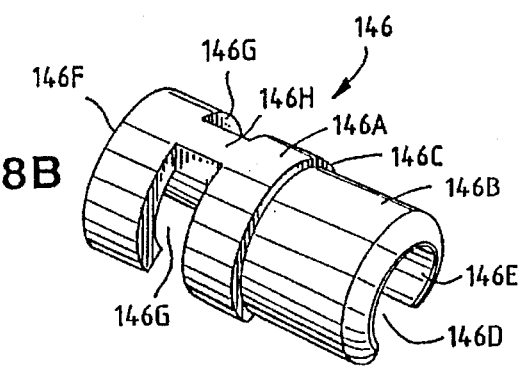
FIG. 8B is a perspective view of a clip for attaching the pump chamber assembly to the rigid frame.

An inlet clip 146 (which is identical to the outlet clip 148 which will not be separately described) is illustrated in detail in FIG. 8B. The inlet clip 146 includes a greater diameter cylindrical portion 146A and a coaxial lesser diameter cylindrical portion 146B with an arcuate step 146C therebetween. The inlet clip further includes a lengthwise opening 146D and open ends 146E and 146F. Lastly, the inlet clip 146 includes a pair of arcuate gaps 146G in the greater diameter portion separated by a land portion 146H. The arcuate gaps 146G of the greater diameter cylindrical portion are received in the arcuate channels 166,168 of the rigid frame 134 to secure the pump chamber assembly 132 to the rigid frame 134 (see FIGS. 6 and 7). The lesser diameter cylindrical portion 146B provides a support to the inlet or outlet valve tubes 142,144 to prevent kinking thereof, as will be discussed below with reference to FIGS. 8C and 8D.

Figure 8C:
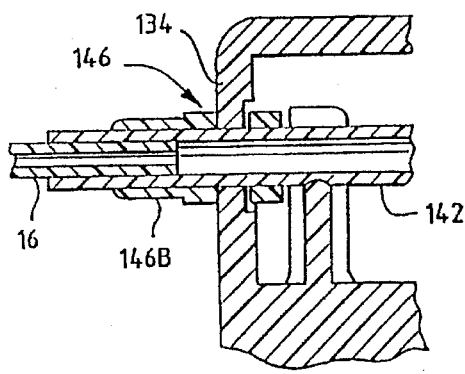
FIG. 8C is a section view of the pump chamber assembly and clip taken along line 8C—8C of FIG. 5.
Figure 8D:
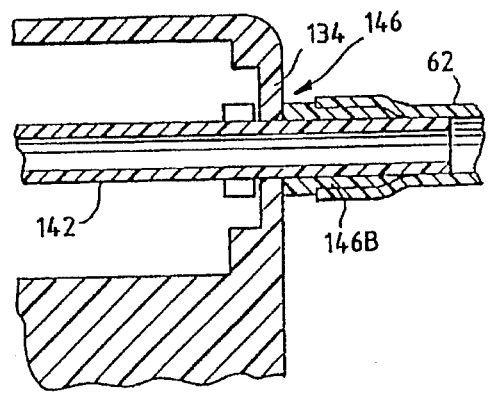
FIG. 8D is a section view of the pump chamber assembly and clip taken along line 8D—8D of FIG. 5.

FIG. 8D illustrates bonding of a large bore tube 62 to the clip 146. The large bore tube 62 is axially slid over the valve tube 142 and the lesser diameter cylindrical portion 146B and solvent bonded to the lesser diameter cylindrical portion 146B. In addition, the inlet valve tube 142 is solvent bonded to the interior of the inlet clip 146. Solvent bonding of the large bore tubing 62 to the lesser diameter cylindrical portion 146 not only provides strain relief in the event of axial or radial loads on the large bore tube 62, it also prevents kinking of the low durometer inlet valve tube 142 so as to decrease the risk of inadvertent occlusion of the inlet valve tube 142 lumen. In addition, engagement of the large bore diameter tube with the lesser diameter cylindrical portion in the manner described above provides a "Chinese finger trap" effect which helps to oppose axial removal of the large bore tube 62 from the clip 146.

FIG. 8C illustrates connection of a small bore tube 16 to inlet valve tube 142. As illustrated in FIG. 8C, the small bore tube 16 is telescopingly received in the inlet valve tube 142 so as to extend into the inlet tube lumen at least as far as the small diameter cylindrical portion 146B of the clip 146. In this manner, a strong solvent bond between the tubes 16,142 is assured. In addition, insertion of the small bore tube 16 this amount assures the inlet valve tube 142 will not be subject to kinking if a tangential load is applied.

Referring to FIG. 8A, the rigid frame 134 is molded from a thermoplastic resin, preferably ABS. The frame 134 includes a first longitudinal member 154, a second longitudinal member 156, an inlet end wall 158 and an outlet end wall 160 integrally joined in a rectangular configuration. Integral first and second support webs 162,164 having alignment holes 165 (see FIGS. 6 and 7) extend between the first and second longitudinal members to improve the rigidity of the rigid frame 134. The inlet and outlet end walls 158,160 each define arcuate channels 166,168, respectively, which open in opposite directions. As illustrated in FIGS. 8A, 8C and 8D, the clips 146,148 are received within the arcuate slot 166,168 to secure the pump chamber assembly 132 to the rigid frame 134. Guide channels 170,172 are defined in the support webs 162,164, respectively, to further support the pump chamber assembly 132 within the rigid frame 134.

An integral guide rail 174 extends longitudinally along an outer edge of the second longitudinal member 156. Integrally formed on the second longitudinal member 156 proximate the inlet end wall 158 are a pair of ramped bumpers 176 extending in opposite directions from both sides of the second longitudinal member. A pair of integrally formed pivot pins 178 extend in opposite directions at approximately the center of the second longitudinal member 156. An integral pair of ramped cam rails 180 extend longitudinally from the second longitudinal member 156 proximate an inner edge and the inlet end wall 158 of the second longitudinal member 156. Proximate the outlet end wall 160 an integral anvil 182 extends from the second longitudinal member 156 toward the first longitudinal member 154. Finally, a pair of integral stops 184 extend in opposite directions transverse of the second longitudinal member adjacent to the outlet end wall 160.

The pincher 138 includes a pair of parallel spaced legs 186 each having a pivot hole 188 at one end and a pair of transverse legs 190 joined by a bridge 192 at their other end. A pair of stops 194 (one shown in FIG. 8) extend lengthwise from the pincher 138 at the base of each of the legs 190. Each leg 186 includes a cam surface 196.

The slider 136 has a generally rectangular body 200 having a transverse outwardly extending gripper bar 202 thereon. A pair of legs 204 extend lengthwise from a first end 206 of the rectangular body 200. At a distal end of each of the legs 204 is a ramped stop 208 which extends inwardly toward the other leg. At the second end 210 of the rectangular body 200 are a pair of lengthwise and inwardly extending legs 212 each having a camming pin 214 (see FIGS. 6 and 7) which extends inward toward the other of the inwardly extending legs 212.

Figure 12:
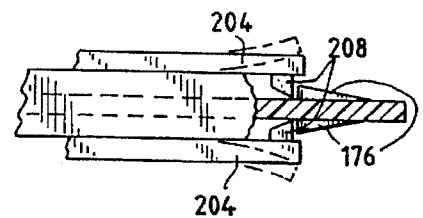
FIG. 12 is a sectional view of the slider stop of the pump cassette.

Assembly of the pump cassette (86) is best understood with reference to FIG. 8A. The pump cassette 86 is assembled by first aligning the pump chamber assembly 132 with the arcuate slots 166,168 of the end walls 158,160 and the guide channels 170,172 of the support webs 162,164. The inlet clip 146 is then force fit into the open end of the arcuate slot 166 of the inlet end wall 158 and the outlet clip 148 is tucked under the outlet wall 160 and force fit within the arcuate slot 168 of the end wall 160, and both the inlet and outlet clips 146,148 are solvent bonded in place. With the pump chamber assembly 132 so engaged to the rigid frame 134, any longitudinal strain on the pump chamber assembly 132 is borne by the clips 146,148 and transferred to the rigid frame 134, thus protecting the pump chamber assembly 132 from such strains. The pincher 138 is then attached to the frame 134 by feeding the outlet valve tube 144 between the legs 186 so that the outlet valve tube 144 rests between the transverse legs 190 and the bridge 192. The holes 188 are then positioned to receive the pivot pins 178 on the second longitudinal member 156. In this manner, the pincher 138 is allowed to pivot relative to the rigid frame 134. Finally, the slider 136 is fed onto the guide rail 174 as illustrated in FIG. 8A. More particularly, the second end 210 lies over the guide rail 174 with the camming pins 214 being received between the ramped cam rails 180 and the cam surface 196 of the legs 186 of the pincher 138. With reference to FIG. 12, as the slider 136 is further slid onto the guide rail 174, the ramped stops 208 engage the ramped bumpers 176, deflecting the legs 204 outwardly with respect to each other until the ramp stops 208 reach the end of the ramped bumpers 176, at which point the legs 204 snap inwardly with respect to each other, securing the slider 136 to the guide rail 174.

C. Anti-Free Flow

The pump cassette 86, the cooperation between the pump cassette 86, the cassette receiving chamber 84, the door 50, the latch 56 and the inlet and outlet pincher valves 122,124 combine to prevent inadvertent free flow during loading and unloading of the pump cassette 86.

Figure 6:
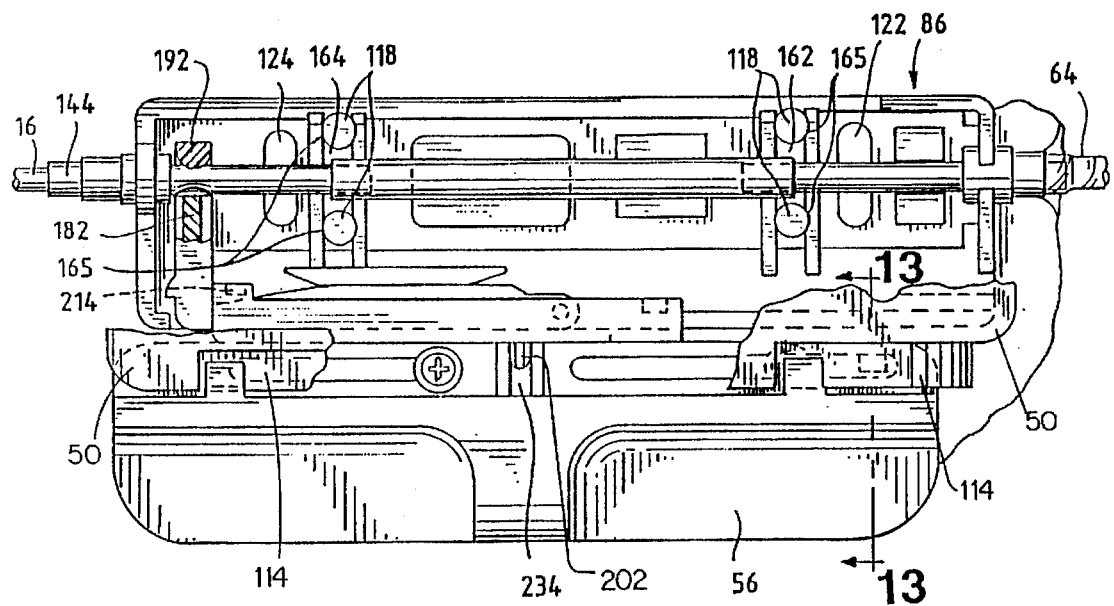
FIG. 6 is a partial plan view of the pump cassette received in the pump cassette receptacle of the present invention with a latch in a "closed" position and a cassette receptacle cover cut-away except by the latch.

With the pump chamber/valve assembly assembled as discussed above, the slider 136 is free to slide back and forth on the guide rail 174 between an open position where the end of the longitudinally and inwardly extending legs 212 abut the base of the transverse legs 190 of the pincher 138 (see FIG. 6) and a closed position where the ramped stops 208 abut the ramped bumpers 176 (see FIG. 7). FIG. 6 illustrates the pump cassette 86 with the slider 136 in the "open" position and FIG. 7 illustrates the pump cassette 86 with the slider 136 in the "closed" position. In both FIGS. 6 and 7 the cassette cover (50) is shown cut-away except in the vicinity of the latch 56 for clarity. With the slider 136 in the open position, the camming pin 214 is out of engagement with the cam surface 196 of the pincher 138 and the ramped cam rails 180 of the frame 134. The resilient properties of the outlet valve tube 144 are thus able to bias the pincher bridge 192 away from the anvil 182 to open the lumen of the outlet valve tube 144 so as to permit flow of fluid through the pump chamber assembly 132. As the slider 136 is moved from left to right toward the closed position as viewed in FIGS. 6 and 7, the camming pin 214 engages the camming surface 196 of the pincher legs 186 and then further engages the ramped cam rail 180 causing the pincher 138 to pivot downward as viewed in FIG. 7 and illustrated by the arrow 216 so as to pinch the outlet valve 144 and occlude its lumen 150, preventing flow of fluid through the pump chamber/valve assembly.

Figure 13:
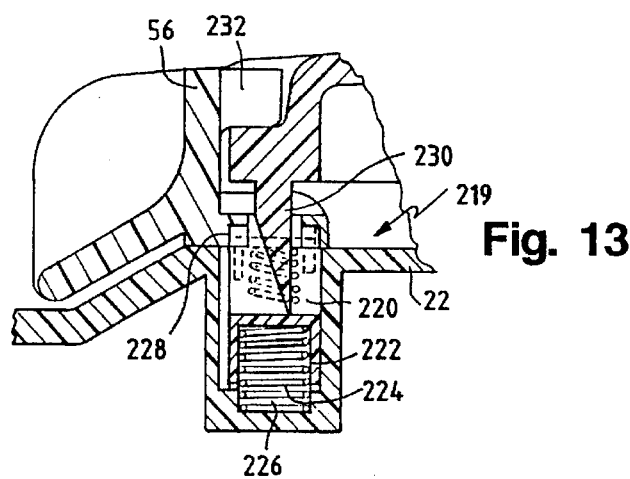
FIG. 13 is a sectional view of a latch detent of the present invention taken along line 13—13 of FIG. 6.
Figure 14:
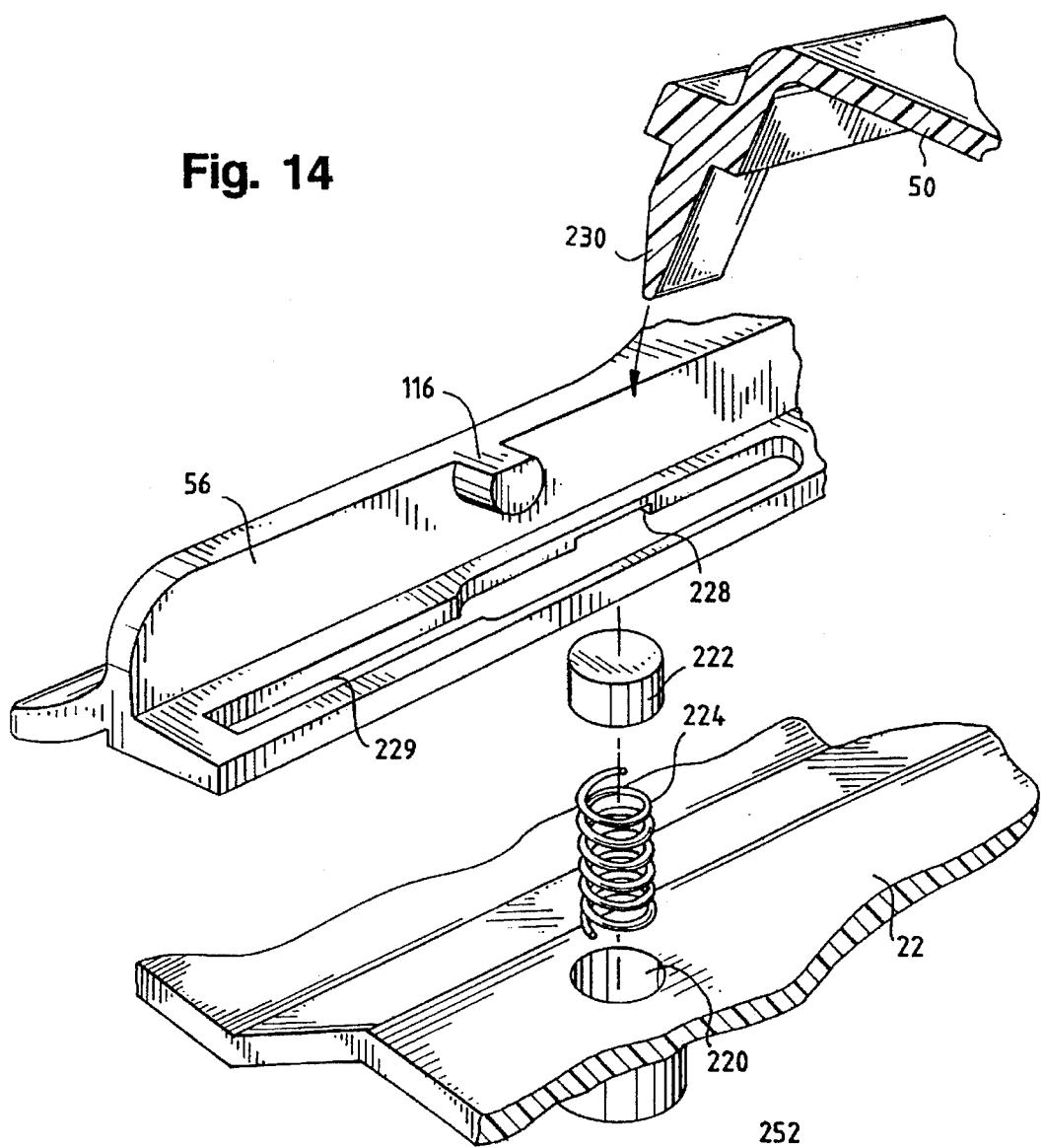
FIG. 14 is an exploded sectional perspective view illustrating interaction of the sliding latch, latch detent and spike.

Referring to FIGS. 13 and 14, the ambulatory infusion pump 10 includes a detent assembly 219 for user convenience to position and maintain the latch in an "open" position until the cassette door 50 is closed. As seen in FIGS. 4, 5 and 14, within the pump cassette receptacle 84 a cylindrical hole 220 extends into the rigid housing back 22. As best seen with reference to FIG. 13, a latch detent piston 222 resides in the cylindrical hole 220. The latch detent piston 222 is biased upward by a latch detent spring 224 affixed to the rigid housing back 22 within a reduced diameter portion 226 of the cylindrical hole 220. With the latch 56 slid to an open position, the latch detent piston 222 is received within a cavity 228 in the bottom of the latch 56 as illustrated by the phantom lines in FIG. 13. The cavity 228 of the latch 56 is formed at one end of an elongate slot 229 in the latch 56 (See FIG. 14). With the latch detent piston 222 received in the cavity 228, the latch 56 cannot slide to the left so as to fasten the cassette door 50 closed. A spike 230 extends normally and inwardly from the cassette door 50. As illustrated in FIGS. 4 and 14, with the cassette door 50 closed, the spike 230 is received within the cylindrical hole 220. Referring to FIG. 13, the tip of the spike 230 forces the latch detent piston 222 into the cylindrical hole 220 and out of engagement with the cavity 228 in the bottom of the latch 56, allowing the latch 56 to be slid to the left, as illustrated in FIG. 6, with spike 230 received in the slot 229. In this manner the engagement pins 116 come into sliding engagement with the lateral cam surfaces 114 of the cassette door 50 so as to bias the cassette door 50 toward the pump cassette receptacle 84 and to secure the cassette door 50 closed.

Loading of the pump cassette 86 into the pump chamber receptacle 84 is best illustrated with reference to FIGS. 5–8A. To load the pump cassette 86 into the pump cassette receptacle 84, the latch 56 is slid to the right as viewed in FIGS. 6 and 7 (and to the left as viewed in FIG. 14) sufficiently for the latch detent piston 222 to be received within the cavity 228 of the latch 56. This position is illustrated in FIG. 7 and in phantom lines in FIG. 13. As seen in FIG. 7, in this position the lateral cam surfaces 114 of the cassette door 50 clear the engagement pins 116 so that the cassette door 50 may be opened or closed. In addition, in order to insert the pump cassette 86 into the pump cassette receptacle 84, the slider 136 must be fully slid to the right (as seen in FIG. 7) and in the closed position with the ramped stops 208 abutting the ramped bumpers 176. Only with the slider so positioned can the gripper bar 202 be received within the slot 234 of the latch 56. The pump cassette 86 is received within the pump cassette receptacle 84 by aligning the gripper bar 202 with the slot 234 of the latch 56 and by aligning the registration pins 118 with the slots 165 of the support webs 162,164. Alignment of the registration pins 118 with the slots 165 has the desirable effect of precisely positioning the pump chamber/valve assembly with respect to the inlet valve pincher 122, the outlet valve pincher 124, the plunger 120, the pressure transducer button wedge 126 and the ultrasonic air detect 130 to ensure proper conveyance during pumping of fluid through the pump chamber/valve assembly and error detection.

With the pump cassette 86 so loaded, the cassette door 50 can be pivoted downward with the engagement pins 116 received within the gaps 115 at the distal edge of the cassette door 50 proximate the bottom of the lateral cam surfaces 114. At the same time, the spike 230 is received within the cylindrical hole 220 forcing the latch detent piston 222 downward and out of contact with the cavity 228 of the latch 56. With the lid so closed, the latch 56 can then be slid to the left, or toward the "locked" position illustrated in FIG. 6. As the engagement pins 116 ride up the lateral cam surfaces 114 the platen 98 is moved close enough to the inlet and outlet valve pinchers 122,124 to fully occlude the inlet and outlet valve tubes 142,144. Only after the inlet and outlet valve tubes 142,144 are occluded is slider 136 moved sufficiently to reach the "open" position illustrated in FIG. 6 wherein the pincher is in a non-occluding position. As the latch 56 is then moved toward the right as illustrated in FIG. 7, the slider 136 causes the pincher 186 to occlude the outlet valve tube 144 before the inlet or outlet valve pinchers 122,124 cease occluding the inlet and outlet valve tubes. In this manner, free-flow through the cassette is prevented during loading and unloading of the cassette.

As the cassette door 50 is closed, the platen 98 is forced into the inner recess 94 of the cassette door 50 by the registration pins 118. The platen is thereby spaced from the piston 120 so the space between the piston 120 surface and the platen varies between precise select distances with the piston fully extended and the piston fully withdrawn to ensure a uniform discharge and full volume of the pump chamber during a pumping cycle. The floating platen and registration pins cooperate to eliminate "tolerance stacking" between the platen 98 of the cassette door 50 and the pump driving mechanism 250.

The cassette 86 can be inserted into the pump cassette receptacle 84 and the cassette door 50 subsequently closed only with the slider 136 initially in the "closed" position and the outlet valve tube 144 pinched shut, thereby preventing inadvertent free flow of fluid to a patient during loading of the cassette 86. If the slider 136 is not in the closed position upon loading the cassette 86, the cassette door 50 will be prevented from closing because the engagement pins 116 will strike the lateral cam surfaces 114 of the cassette door 50. This feature assures that at least one of the inlet or outlet pincher valve pinchers 122,124 will be occluding the lumen of the inlet or outlet valve tubes 142,144 when the door 50 is closed and the latch 56 is moved from the open to the closed position, again preventing inadvertent free flow of fluids to a patient.

D. Pumping Mechanism

Figure 15:
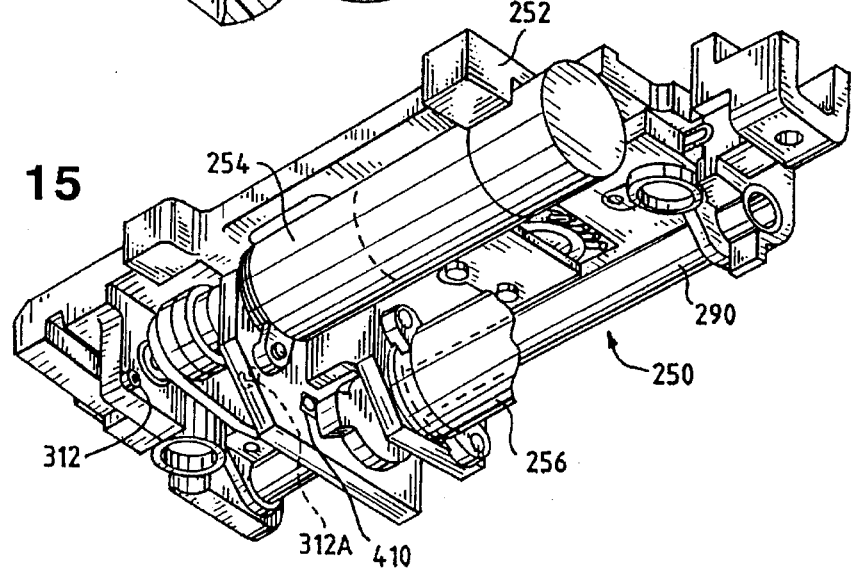
FIG. 15 is a perspective view of a pump driving mechanism of the present invention with a portion of a plunger motor removed for clarity.
Figure 16:
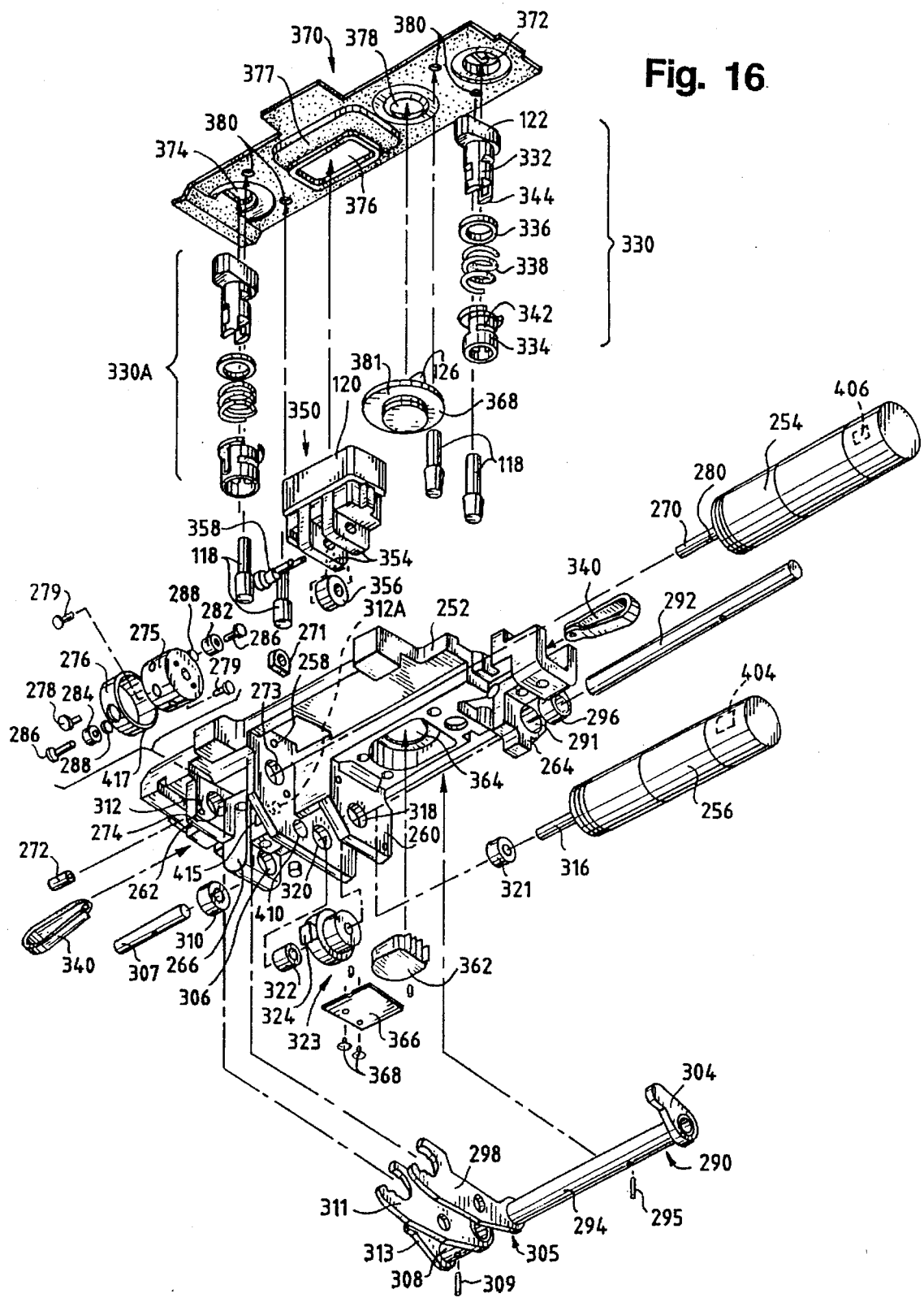
FIG. 16 is an exploded perspective view of the pump driving mechanism.

The ambulatory infusion pump includes a pump driving mechanism 250 generally illustrated in FIGS. 15 and 16 which acts on the pump chamber assembly 132 to propel fluid therethrough. The pump driving mechanism 250 is generally illustrated in FIGS. 15 and 16 and includes an assembly frame 252 to which the valve motor 254 and the plunger motor 256 are attached. The assembly frame 252 includes a central boss 258, a plunger motor support boss 260, a valve drive shaft support boss 262, an inlet valve support boss 264, an outlet valve support boss 266, and an intermediate valve support boss 268.

The valve motor 254 is a DC electric motor secured to the central boss 258 with the valve drive shaft 270 received in bushings 271,272 in axially aligned bores 273,274 in the central boss 258 and the valve drive support boss 262. A crank carrier 275 rides on the valve drive shaft 270 between the central boss 258 and the valve drive support boss 262 and a flag ring 276 having a knurled finish surrounds the outer periphery of the crank carrier 275. A set screw 278 secures the flag ring 276 to the crank carrier 275. A pair of 90° off-set screws 279 secure the valve drive shaft 270 and the tip of the set screws 279 engage corresponding 90° off-set flats 280 on the valve drive shaft 270 to prevent rotation between the drive shaft 270 and the crank carrier 275. An inlet valve bearing 282 and an outlet valve bearing 284 are attached to the crank carrier 275 by a pair of press pins 286 and are spaced from the crank carrier 275 by washers 288. In this manner the bearings 282,284 may spin freely about the press pins 286.

An inlet rocker arm 290 is mounted between an orifice 291 in the inlet valve support boss 264 and an orifice (not shown) in the intermediate valve support boss 268 by an inlet valve shaft 292 received within an inlet valve shaft envelope 294 of the inlet rocker arm 290 and is secured thereto against relative motion by the pin 295. Bushings 296,297 in the orifices 291,293 provide for smooth rotation of the shaft 292. An inlet valve cam 298 extends transversely from a front end of the inlet valve shaft envelope 294 with its distal end received around the bearing 282. A valve actuator 304 extends transversely from a second end of the inlet valve shaft envelope 294. An outlet valve rocker arm 305 is mounted between an orifice 306 in the outlet valve support boss 266 and an orifice in the intermediate valve support boss 268 about an outlet valve shaft 307 received in the outlet valve shaft envelope 308 and the outlet valve envelope 308 is secured against rotation relative to the outlet valve shaft 307 by the pin 309. A bushing 310 in the outlet valve support boss orifice and a bushing (not shown) in the intermediate support boss orifice provide for smooth rotation of the shaft 307. An outlet valve cam 311 at a first end of the outlet valve envelope 306 receives the bearing 284 at its distal end. At the second end of the outlet valve envelope 306 is an outlet valve actuator 313.

Figure 17:
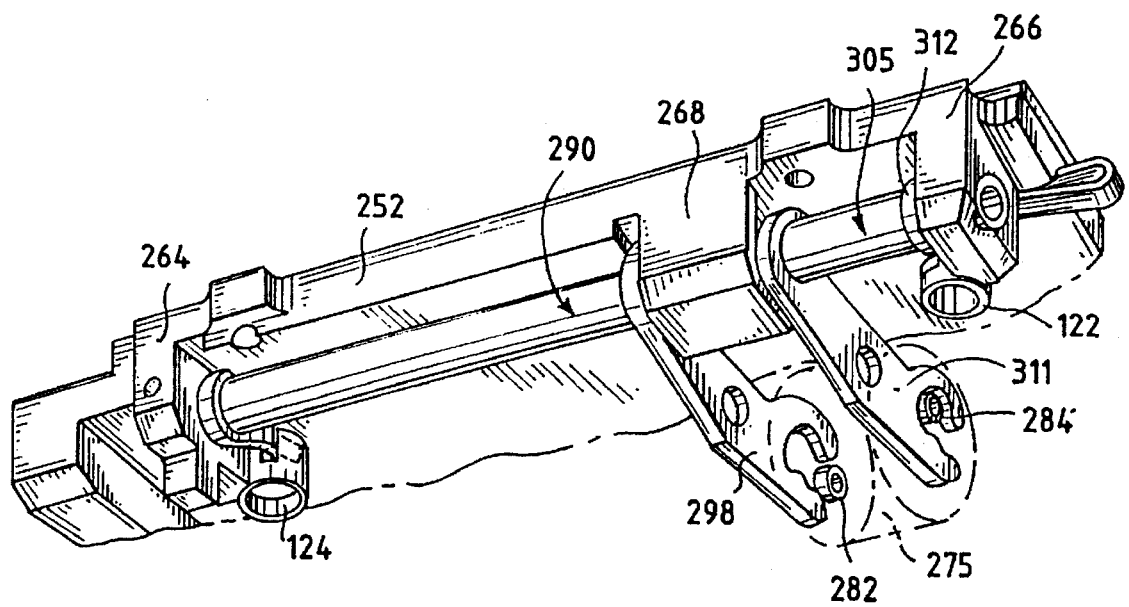
FIG. 17 is a perspective view of the inlet and outlet rocker arms of the pump driving mechanism.

FIG. 17 illustrates the crank carrier 275, the valve motor shaft 270, the inlet rocker arm 290 and the outlet rocker arm 305 in a "neutral" position with the inlet valve pincher 122 and outlet valve pincher 124 biased closed. As seen in FIG. 17, the inlet valve bearing 282 is located on an opposite end of the crank carrier 275 from the outlet valve bearing 284, and the inlet valve bearing and the outlet valve bearing are located on radii extending 180° from each other.

Figure 18A:
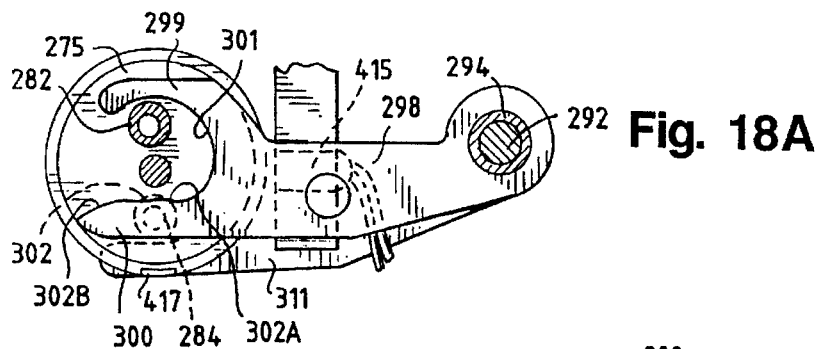
FIG. 18A–18D are left side views with respect to FIG. 17 of the inlet valve cam and the outlet valve cam in engagement with the crank carrier connected to the valve motor shaft.

FIG. 18A is taken from the perspective of the left-hand side of the inlet valve cam 298 as viewed in FIG. 17. The inlet valve cam 298 includes a first leg 299 and a second leg 300 defining an arcuate surface 301 therebetween. The outlet valve cam 311 is configured identical to the inlet valve cam 298, which simplifies manufacture of the pumping mechanism. The arcuate surface 301 forms a dual cam 302 having a first cam surface 302A and a second cam surface 302B proximate the distal end of the first leg 300. The dual cam surface 302 is configured so that as the crank carrier 275 is rotated clockwise from the valve neutral position from the perspective of FIG. 18A, the first cam surface 302A is engaged by the outlet valve bearing 284 causing the outlet valve cam 311 to lift the outlet pincher valve 124. The arcuate surface 301 proximate the first leg 299 is configured so that the inlet valve bearing 282 kisses the arcuate surface 301 without causing movement of the inlet valve cam 298. In a like manner, when the crank carrier 275 is rotated clockwise from the valve neutral position from the perspective of FIG. 18A, the second cam surface 302B is engaged by the inlet valve bearing 282, causing the inlet valve cam 298 to lift the inlet pincher valve 122.

Referring to FIGS. 15 and 16, the plunger motor 256 is a DC electric motor attached to the plunger motor support boss 260 with the plunger drive shaft 316 received within the axially aligned holes 318,320 in the plunger motor support boss 260 and the central boss 158, respectively. Bushings 321,322 facilitate rotation of the plunger drive shaft 316 within the holes 318,320. Mounted about the plunger drive sham 316 is a plunger cam 323 nested between the central boss 258 and the plunger motor support boss 260 and held in place by a pair of 90° offset screws and corresponding flats (not shown. The plunger cam 323 has a flag or mechanical stop 324 integrally formed between a least diameter portion 325 and a greatest diameter portion 326 of the plunger cam surface. Beginning at a "home" position with the plunger fully retracted, the DC electric plunger motor 256 oscillates approximately 194° in a first direction, thereby engaging the greatest diameter portion 326 of the plunger cam 322 with the plunger 120 to extend the plunger 120 so as to compress the pump chamber 140. The plunger motor can reverse direction and rotate the plunger cam 323 up to 200° in a second direction opposite the first direction until the flag 324 couples the optosensor 410, thereby returning the plunger to the "home position" by engaging the least diameter portion 325 of the plunger cam 323 with the plunger 120, allowing the pump chamber 140 tubing to bias the plunger 120 to its fully retracted position. Runaway is prevented by the mechanical stop 324 of the plunger cam 323 abutting the assembly frame 252 to mechanically stop rotation of oscillating plunger motor 256 in the event of a system failure.

The ambulatory infusion pump 10 uses a separate valve motor 254 and plunger motor 256 to allow for the independent control and timing of the valves and the plunger. In addition to making the fail-safe reciprocating action discussed above possible, the use of two motors allows each motor to be optimized for its own selected task. In this manner, the motors are more energy efficient than attempting to use one motor for both plunger and valve actuation. The use of two motors also allows independent control of the plunger and valves, a feature which is used to perform a number of self-test and self-compensating functions and to facilitate delivery of fluid at different rates through different pump modes employing a number of distinct plunger and valve actuation sequences, all of which will be discussed in greater detail below.

As seen in FIG. 16, inlet and outlet valve assemblies 330, 330A include a valve pincher mount 332 received within a valve guide 334 with a valve washer 336 and a compression spring 338 axially nested therebetween. The valve guide 334, in turn, is attached to the assembly frame 252 where indicated in FIG. 16. The compression spring 338 biases the mount valve pincher 332 away from the assembly frame 252 to an extended position for occluding the inlet or outlet valve tubes 142,144. In addition, a C-spring or leaf spring 340 is received in a slot 342 of the inlet valve guide 334 and acts on the proximal end 344 of the valve pincher mount 332 to further bias the valve pincher 332 away from the assembly frame 252 to an occluding position. The leading edge of each of the inlet and outlet valve pinchers 122,124 has a small radius of 0.03 inches. This small radius minimizes the energy necessary to occlude the inlet and outlet valve tubes 142,144 while minimizing kinking of the tubing during occlusion. In addition, as most clearly seen in FIG. 10, the stops 131 at opposite ends of the leading edge of the inlet valve pincher 122 (and, though not separately illustrated, on the outlet pincher 124), maintain a 0.04 inch gap between the pincher valve and the platen which further minimizes tube kinking while the tubes are occluded. Either of the compression spring 338 or the C-spring 340 provides sufficient bias to the valve pinchers 122,124 to occlude the inlet and outlet valves 142, 144, thus providing an added margin of safety. Furthermore, this spring bias ensures that if power to the pump is cut off, the valves will return to a neutral position occluding the inlet and outlet valves 142,144 or, if either valve is in the over center position when the power is cut-off, the valve will remain open and the other valve will be biased closed.

A plunger assembly 350 includes the plunger 120 having a back 352 with a pair of bosses 354 which receive a cam follower or ball bearing 356 therebetween, the cam follower 356 being maintained in place by an eccentric 358 for calibration of the plunger position. The plunger cam 323 acts on the cam follower 356 to drive the plunger upward as the plunger cam 323 rotates in a counter-clockwise direction with reference to FIG. 19.

A pressure transducer 362 is received in a stepped hole 364 in the assembly frame 252. A transducer backing plate 366 is fastened to the assembly frame 252 by screws 368 to maintain the pressure transducer 362 in a fixed position. A transducer button 368 is also received within the stepped hole 364 and extends outwardly from the assembly frame 252 opposite of the pressure transducer 362 so that the transducer button wedge 126 can extend between the guide posts 128 into the pump cassette receptacle 84.

A gasket 370 made of a molded silicone rubber has an inlet valve pincher orifice 372, an outlet valve pincher orifice 374, a plunger orifice 376 surrounded by a raised collar 377, a transducer button orifice 378, and four registration pin orifices 380. The transducer button 368 is inserted through the pressure transducer orifice 378 so that the flange 381 is on the frame side of the gasket. The plunger 120 is inserted into the plunger orifice 376 such that the gasket sits in a slot in the frame 252 around the plunger 120. The registration pins 118 are fixedly attached to the bottom of the assembly frame 252 and are received within the registration pin orifices 380 of the gasket 370. The gasket 370 is then stretched so that the inlet and outlet valve pinchers 122,124 are received within the inlet and outlet pincher orifices 372,374 and the gasket is press fit against the frame. The gasket 370 functions as a face seal between the inner surface of the rigid housing back 22 and each component. The raised collar 377 functions to resiliently bias the plunger 120 toward the frame 252 to maintain the cam follower 356 in contact with the plunger cam 323 even if the door 50 is open or no cassette 86 is in the cassette receptacle 84.

FIGS. 18A–D illustrate actuation of the inlet and outlet valve pinchers 122,124 by the valve motor 254. As the crank carrier 275 is rotated counterclockwise with respect to FIG. 18A, the inlet valve bearing 282 engages the second cam surface 302B, actuating the inlet valve 298 against the action of the spring 338 and C-spring 340 so as to open the inlet valve tube 142. Although not illustrated, with the valve carrier so rotated, the outlet valve bushing 284 kisses the arcuate surface 301 proximate the first leg 299 of the outlet valve cam 310, thereby exerting no force on the outlet valve cam 311. As the outlet valve bearing 284 disengages the first cam surface 302A, the outlet valve cam 311 is biased upwards by the force of the springs 338 and 340. However, should the outlet valve become stuck in an open position contrary to the bias of the springs 338 or 340, the outlet valve bushing 284 will forcibly contact the arcuate surface 301. This may have the effect of dislodging the outlet pincher valve 124 from the non-occluding position or, more likely, it will result in an increased draw of energy on the valve motor, thereby triggering an alarm (see Section F below).

Figure 18B:
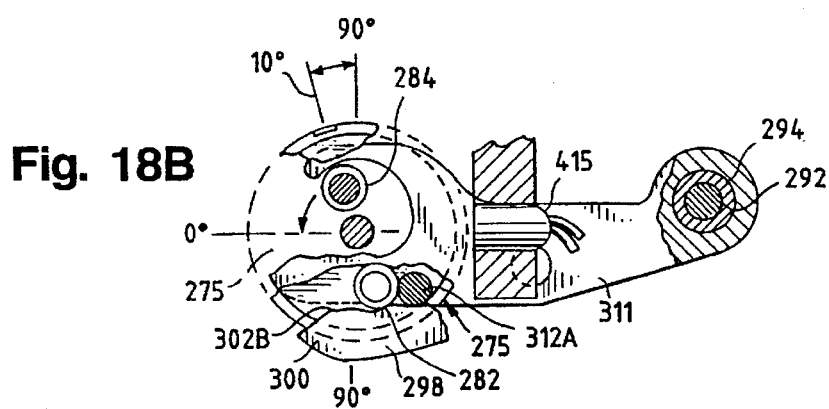
Figure 18C:
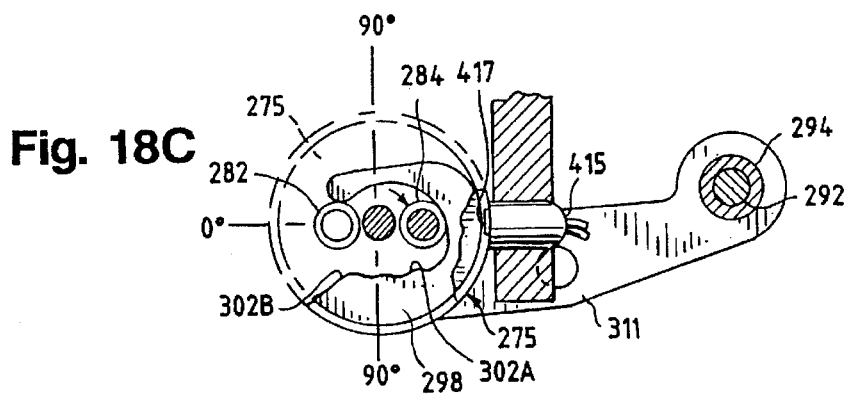
Figure 18D:
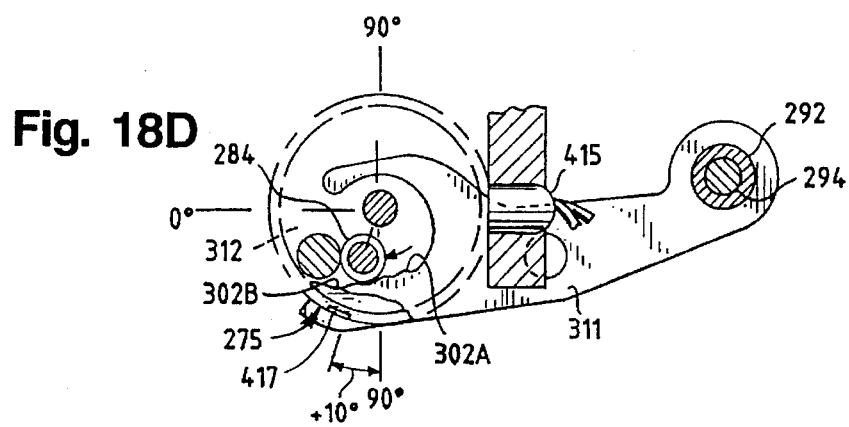

FIGS. 18B–D serve to illustrate an over center feature of the valve driving mechanism. FIG. 18C illustrates the inlet valve cam 298 in the valve neutral position. FIG. 18D illustrates that the crank carrier is rotated clockwise from the valve neutral position of FIG. 18C. The inlet valve bearing 282 kisses the arcuate surface 301 proximate the first leg 299 of the inlet valve cam 298. Concurrently, the outlet valve bushing 284 engages the first cam surface 302A, thereby actuating the outlet valve cam 311 and fully opening the outlet pincher valve 124 after 90° of rotation. The crank carrier 275 is rotatable approximately an additional 10° clockwise to an over center position illustrated in FIG. 284D, whereupon the outlet valve bushing 284 engages the stop 312. At the over center position, the outlet valve cam 311 is "locked" in position against the bias of the springs 338 and 340. The valve motor rotates the crank carrier 275 counterclockwise back to the valve neutral position illustrated in FIG. 18C. Further rotation of the crank carrier 275 90° counterclockwise will cause the inlet valve bearing 282 to engage the second cam surface 302B, actuating the inlet valve cam. (See FIG. 18B) As with the outlet valve assembly, rotation an additional 10° will "lock" the inlet valve cam 298 in an over center position. Accordingly, if power to the valve motor is cut off, three valve positions are possible: 1) crank carrier halted over center with the outlet valve open and the inlet valve closed; 2) crank carrier halted in the valve neutral position with both valves closed; or 3) the valve carrier halted in an over center position with the inlet valve opened and the outlet valve closed. Thus, at least one valve is always closed, preventing unintentional free flow. It should be noted that at high pump rates, the valve motor does not pause with the crank carrier in the valve neutral position.

E. Position Sensor/Magnetic Detent

As will be discussed below with reference to FIG. 32, the pump 10 includes an electronic control 385 which actuates the pumping assembly 250 and receives signals from a variety of sensors to monitor pump performance.

Figure 20:
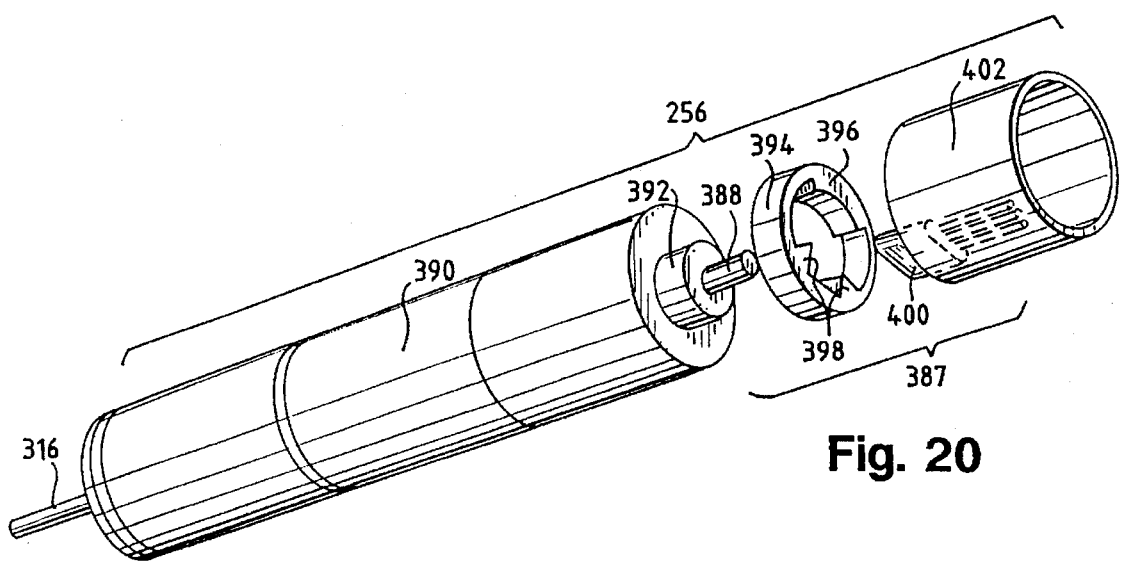
FIG. 20 is an exploded perspective view of a position encoder/magnetic detent of the plunger motor.

The plunger motor 256 is shown in an exploded perspective view in FIG. 20 to illustrate a Hall sensor/magnetic detent assembly 387 for permitting precise monitoring of the plunger position and for maintaining the plunger in a precise position when the plunger motor is not energized. A motor drive shaft 388 extends opposite the plunger drive shaft 316 from the body 390 of the plunger motor 256. Fixed to the motor drive shaft 388 for rotation with the motor drive shaft is a rotary cylindrical Neodymium-Yag magnet 392. Radially spaced about the periphery of the rotary magnet 392 is a ferromagnetic collar 394, the ferromagnetic collar being made of soft iron in the present embodiment. Integrally formed in an inner surface of the ferromagnetic collar 394 is an inwardly extending flux collector 396. Located on the ferromagnetic collar 394 opposite the flux collector 396 are a pair of spaced bosses 398 extending inwardly from an inner surface of the ferromagnetic collar, the bosses being spaced to receive a Hall sensor 400 therebetween. A shell 402 is provided for encasing the Hall sensor/magnetic detent assembly 387. As generally understood by those skilled in the art, the Hall sensor 400 is used to sense the position of the motor drive shaft 388 so that the corresponding position of the plunger 120 can be precisely monitored. More particularly, the Hall sensor 400 sends a signal to the control 385, once each revolution of the shaft 388, so that the control 385 can track the precise location of the plunger 120.

The flux collector 396 cooperates with the magnet 392 to function as a magnetic detent. More particularly, when the motor 256 is deenergized, rotation of the motor shaft 388 will be resisted by attraction of the poles of the magnet 392 to the flux collector 396. This attraction or detent feature provides sufficient resistance to rotation of the shaft 388 that the plunger 120 can be maintained in a selected position notwithstanding the pump chamber 140 biasing the plunger 120 to retract. That is, the detent provides sufficient holding torque with the motor turned "off" during a sleep sequence to prevent back driving of the plunger. In this manner, the DC electric motor 256 functions like a stepper motor in that its shaft can be stopped at precise locations. However, the DC electric motor maintains the advantage of being significantly more energy efficient and lightweight than a stepper motor. In addition, when the shaft 388 is rotated at high speeds, the magnetic detent effect becomes "transparent" in the sense that vibration of the motor is minimized.

F. Other Sensors

As seen in FIG. 16, in addition to the Hall sensor/magnetic detent assembly 387, the plunger motor 256 includes a sensor 404 for monitoring motor current, the sensor 404 producing an electrical signal proportional to the motor current. The control 385 monitors the electrical signal to confirm proper operation of the motor. If an abnormal condition is present, the control 385 activates an alarm.

The valve motor 254 also includes a Hall sensor 406 for producing an electric signal with each revolution of the valve motor drive shaft which is similar to the Hall sensor/magnetic detent 287 of the plunger motor, only lacking the flux collector 297 and therefore the magnetic detent feature of the Hall sensor/magnetic detent 387 of the plunger motor 256. In addition, a valve motor sensor 408 produces an electrical signal proportional to the current drawn by the valve motor 254, which is monitored by the control 385 as discussed above with respect to the plunger motor 256.

Figure 19:
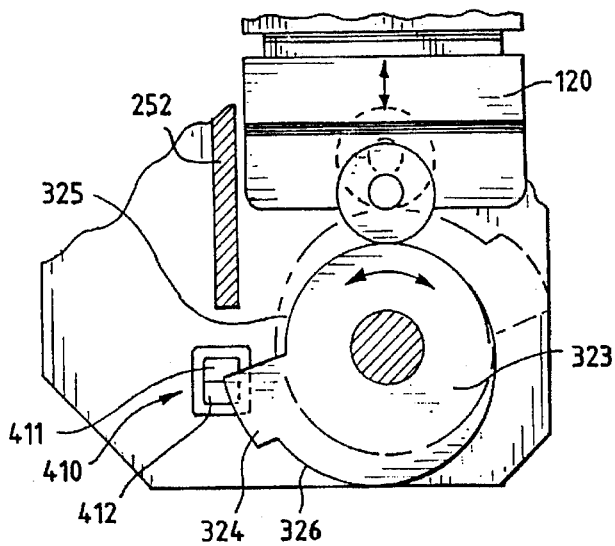
FIG. 19 is a right side view with respect to FIG. 16 of the plunger cam and plunger.

Optical position sensors are also included as part of the plunger and valve drive for the purpose of monitoring the position of the plunger 120 and the inlet 122 and outlet 124 valves. A plunger optical sensor 410 (see FIGS. 15, 16 and 19) includes a light emitting diode 411 and a photodetector 412 (FIG. 19). With the plunger cam rotated to its "home" position as illustrated in FIG. 19, the plunger cam flag 324 causes a coupling between the light emitting diode 411 and the photodetector 412 which in turn causes the cam position sensor 410 to send an electric signal to the control 385 indicating that the plunger cam 323 is in its "home" position, corresponding to the plunger 120 being in a "retracted" position. As the plunger cam 323 actuates the plunger 120 out of the home position illustrated in FIG. 19, the light emitting diode 411 and photodetector 412 are uncoupled and the LED and photodetector can be turned off to save power. If turned off, the LED and photodetector are repowered when the control 385 determines, by virtue of signals received from the Hall sensor 400, that the plunger cam has returned to the home position.

A valve optical sensor 415 is located where indicated in FIGS. 16 and 18A–D. The flag ring 276 has a black anodized outer surface with a non-coated reflective window 417. The valve optical sensor includes an LED and a photodetector, not separately shown. When the reflective window 417 aligns with the optical sensor, the LED and the photodetector are "coupled", causing generation of an electric signal which is sent to the control 385. The reflective window 417 aligned with the valve optical sensor 415 corresponds to a "neutral" position of the valve motor crank 270, meaning that both valves are closed. When the reflective window is rotated out of alignment with the valve optical sensor, the LED and photodetector are uncoupled and the valve optical sensor is turned off to conserve power. The position of the window 417 is adjusted during calibration of the pump to precisely correspond to the neutral position by loosening of the set screw 278 and rotation of the flag ring 276 relative to the crank carrier 275.

The plunger optical sensor 410 and the valve optical sensor 415 are used in conjunction with the plunger motor Hall sensor 400 and the valve motor Hall sensor 406 to precisely monitor the location of the plunger and the inlet and outlet valves relative to their home and neutral positions, respectively. More particularly, the optical sensors are used by the control 385 to define the home and neutral position of the plunger and valve. The Hall sensor provides a much freer resolution for locating the plunger and valve relative to the home and neutral positions. For example, with respect to the plunger, twenty-five revolutions of the motor are required to fully extend the plunger from its home position. Each revolution of the motor results in one signal from the plunger motor Hall sensor 400, therefore counting of the signals from the Hall sensor by the control 385 permits precise location of the plunger. Thus, the plunger and valve optical sensors 410,415 are used by the control 385 to verify the accuracy of the position determined based upon the Hall sensors, to calibrate position of the plunger and valves, by being turned on and off by the control 385, to conserve energy.

Figure 21:
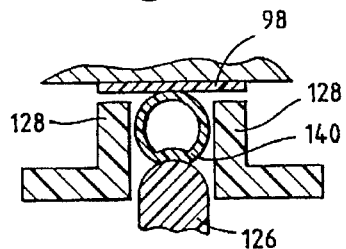
FIG. 21 is a sectional view of the transducer button wedge bearing upon the pump chamber.

The pressure transducer 362 is operatively linked to the pump chamber 140 by the button wedge 126, as best seen in FIGS. 4 and 16. The pump chamber 140 is received between the guide posts 128 which ensures that the arcuate leading edge 127 of the button wedge 126 compresses the pump chamber against the platen 98 in the manner illustrated in FIG. 21. Pressure fluctuations within the pump chamber result in a change in force applied to the button wedge 126 which is detected by the transducer 362. The transducer 362 produces an electric signal representative of the pressure in the pump chamber 140 which is transmitted to the control 385. The control 385 monitors pressure in the pump chamber to check for insufficient pump chamber refill, valve leakage or downstream occlusion, as will be discussed in greater detail in Section N2 below.

A cassette door sensor 420 is illustrated in FIG. 3. It is a magnetic proximity sensor which monitors when the cassette door 50 is properly engaged to the rigid housing back 22. More particularly, the door sensor 420 sends an electric signal to the control 385 when latch 56 is a "closed" position. When such a signal is received, the control 385 permits pump operation.

A front cover sensor 422 (see FIG. 2) is a magnetic proximity sensor which detects when the front cover 24 is slid down to uncover the programmer display 28 and keyboard 30. When the control panel 26 is opened a sufficient distance, the front cover sensor will send an electric signal to control 385, causing the control 385 to energize a programming display 228. When the front cover 24 is closed and the electric signal is no longer received, the control 385 deactivates the programmer display 28 to conserve power.

The ultrasonic air detector 130 (see FIG. 4) is provided for ensuring that excessive air is not delivered with the liquid medication to a patient. The ultrasonic air detector 130 includes a conventional piezoelectric ultrasonic transmitter 130A and receiver 130B spaced apart on both sides of the inlet valve tube 142 (see FIG. 44). The transmitter and receiver are spaced slightly less than the outer diameter of the inlet valve tube 142 to assure that the inlet valve tube 142 fits snugly therebetween. The finger 423 extends from the door 50 and received between the transmitter and receiver 130 to force the inlet valve tube 142 between the transmitter and receiver 130 upon closing the door 50 and to secure the inlet valve tube 142 therebetween. The transmitter 130A produces an ultrasonic signal that is transmitted through an inlet valve tube 142 to the receiver 130B. Liquid present in the inlet valve tube 142 between the transmitter and the receiver conveys the ultrasonic signal much more efficiently than does an air bubble. The receiver produces and transmits to the control 385 an "air" signal if the sonic signal it receives is indicative that a volume of air in excess of a select amount is present in the inlet valve tube 142 between the transmitter and the receiver. During refill of the pump chamber, an ultrasonic signal is produced once each motor revolution. Only if the signal received by the control 385 indicates that an unacceptable level of air is present for a select number of refill revolutions will an alarm indicating air in the pump chamber be triggered. The air detect routine of the control 385 is discussed in further detail in Sec. N2. Details of the circuitry, structure and operation of prior art ultrasonic air detectors can be found in Fellingham et al., U.S. Pat. No. 5,191,795; Pastrone et al., U.S. Pat. No. 4,821,558; and Pastrone et al., U.S. Pat. No. 4,944,191, the disclosures of which are incorporated by reference herein.

G. Soft Pump Case

Figure 22:
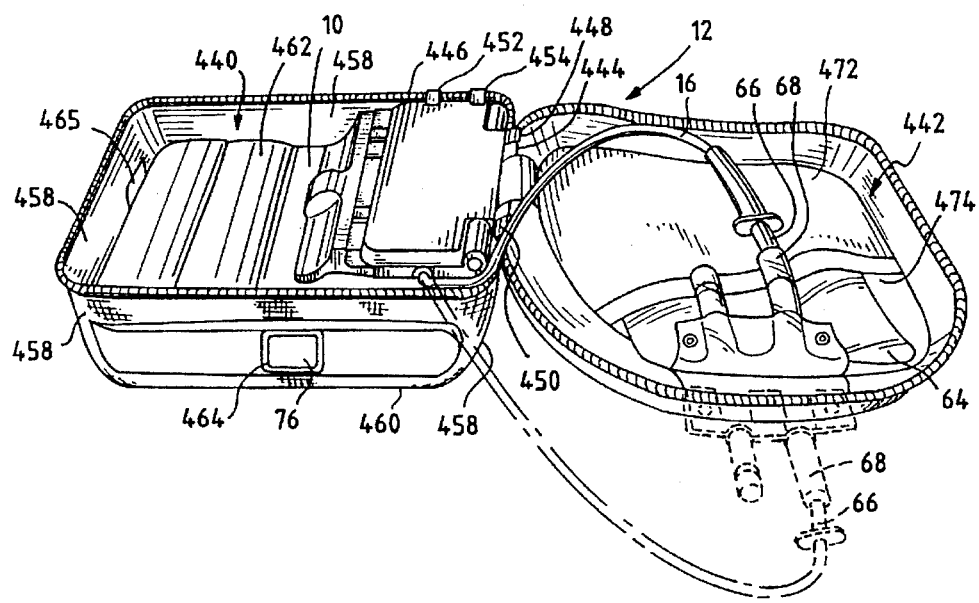
FIG. 22 is a perspective view of the ambulatory infusion pump received in a soft pump case with the case open.
Figure 23:
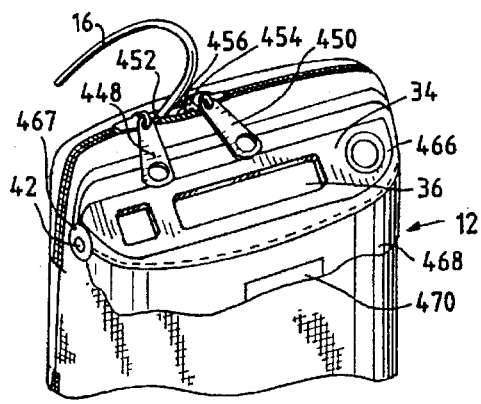
FIG. 23 is a perspective view of the ambulatory infusion pump mounted in the soft pump case with the patient display exposed.
Figure 24:
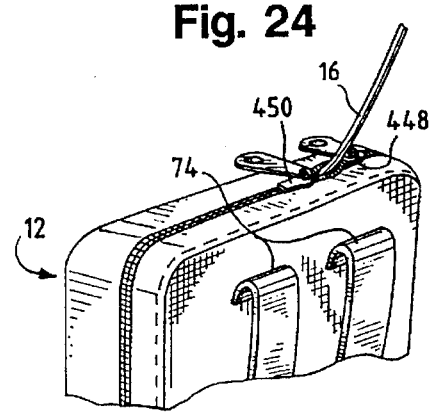
FIG. 24 is a perspective view of the rear of the soft pump case.

The soft pump case 12 is shown in detail in FIGS. 22–24. The soft pump case 12 is made of fabric such as a waterproof nylon and includes a pump receiving chamber 440 and a solution bag receiving chamber 442 joined by an integral hinge 444. The pump receiving chamber 440 and the solution bag receiving chamber 442 are joinable in an abutting and overlying relationship by a zipper 446. The zipper 446 includes a first slider 448 and a second slider 450 and first and second stops 452,454. As illustrated in FIG. 23, with the first and second sliders 448,450 positioned with the zipper teeth engaged, they come into abutment with the first and second stops 452,454 to define a gap 456 through which the IV tube 16 can extend from the soft pump case 12. The second slider 450 causes approximately three-quarters of the zipper teeth to become engaged and disengaged and the first slider 448 causes less than a quarter of the zipper teeth to become engaged and disengaged.

The pump receiving chamber 440 includes four side walls 458 and a bottom wall 460 with the zipper teeth at the distal end of the side walls 458. An elastic retention strap 462 extends across the bottom wall 460 for securing the ambulatory infusion pump 10 within the pump receiving chamber 440. Alternatively, a hook and loop strap could replace the elastic retention strap 462. A variety of holes are provided in the side walls 458 of the pump receiving chamber to allow for access to the pump controls. For example, the hole 464 provides access to the on/off switch 76, a hole 465 provides access to the IR window 70 and a grommet 467 provides access to the remote bolus switch contact 42 (see FIG. 23). A clear plastic membrane preferably covers the hole 464 to protect the ambulatory infusion pump 10 from dirt and moisture. FIG. 23 illustrates a panel 466 which provides for access to the user control panel 32. In one embodiment, the panel 466 is covered with a clear plastic membrane to allow for observation of the patient display 36 as well as access to the control buttons on the beveled front surface 34 of the pump 10. A cover 468 can selectively cover or expose the panel 466 and is preferably secured to the exterior of the pump receiving chamber 440 by a hook and loop connector 470 such as Velcro®.

The solution bag chamber 442 includes a partition 472 defining a pocket 474 for receiving the solution bag 64. A pair of straps 74 are on the exterior of the solution bag chamber 442 for fastening the soft pump case to an upright support such as a patient's belt (see FIG. 1).

As illustrated in FIG. 22, with the solution bag 64 received in the pocket 474, the solution bag outlet orifice 68, including the spike 66, can be folded over the solution bag 64 and the partition 472. The solution bag chamber 442 can then be folded over the pump receiving chamber 440 in a book-like fashion so that the first and second sliders 448,450 can engage the teeth of the zipper 446 to close the soft pump case 12. With the soft pump case so closed, the ambulatory infusion pump 10 can be attached to a patient by the belt loops 74 (see FIG. 24) for convenient travel with the patient. The solution bag is located between the rigid front and back housings 20,22 of the ambulatory infusion pump 10 and a patient's body, thereby protecting the solution bag 64 from damage. In addition, the fluid within the solution bag 64 is maintained at or near the patient's body temperature. This improves pump accuracy because changes in viscosity resulting from changes in liquid temperature are minimized. Furthermore, the solution bag provides padding between the patient and the pump, enhancing patient comfort.

H. Pump Displays and Delivery Profiles

Figure 25:
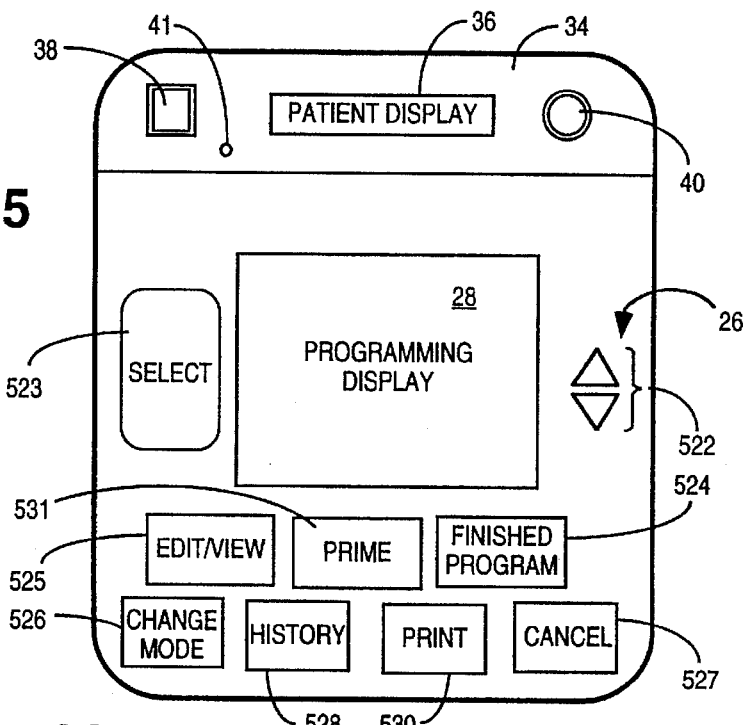
FIG. 25 is a plan view of the control panel and beveled front surface of the ambulatory infusion pump.
Figure 26:
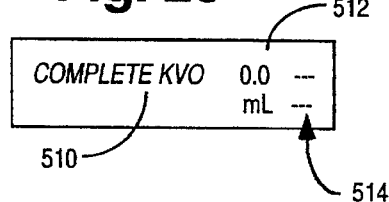
FIG. 26 is a plan view of the patient display.

The control panel 26 and beveled front surface 34 are shown in greater detail in FIG. 25. A sample patient display 36 is illustrated in FIG. 26. The patient display shows user information through fixed segments or icons 510. For example, in FIG. 26 the "COMPLETE KVO" icon means that the current infusion has ended and the pump is now running at the Keep Vein Open (KVO) rate. Volume remaining in a medication supply is shown at 512. Lines 514 are sequentially illuminated to provide a user immediate confirmation that the pump is pumping.

The programming display 28 is used for data entry and displaying status information to a clinician. The three major screens which the clinician will see are the select delivery mode (FIG. 27), set up (FIG. 28) and status (FIG. 29).

Figure 27:
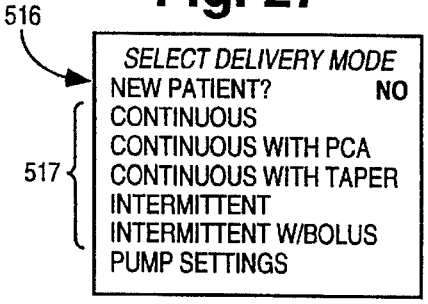
FIG. 27 is a plan view of the program main display with a "select delivery" mode screen.

A sample select delivery mode screen 516 is illustrated in FIG. 27. Each of the five delivery profiles 517, which are discussed in this section below, are listed: 1) continuous; 2) continuous with patient controlled analgesia (PCA); 3) continuous with taper; 4) intermittent; and 5) intermittent with bolus.

Figure 28:
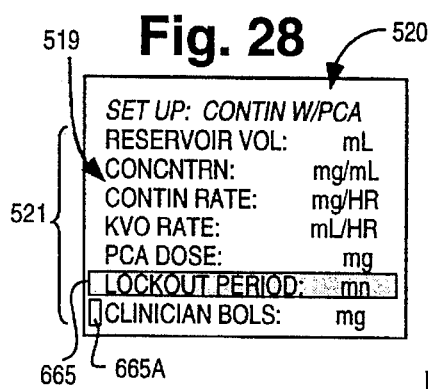
FIG. 28 is a plan view of the programming display with a sample "setup" screen.
Figure 29:
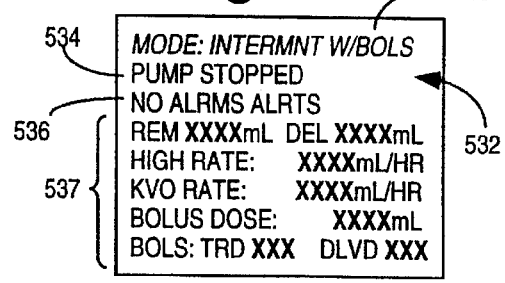
FIG. 29 is a plan view of the programming display with a sample "mode" screen.

A sample setup screen 519 is illustrated in FIG. 28. A distinct setup screen is displayed for each delivery profile 517. An icon 520 indicates the appropriate delivery profile. Here, the setup screen is for continuous infusion with a PCA. Using the keyboard 30, a clinician can enter values for each of the input options 521, as discussed in greater detail below.

For example, the reservoir volume, medication concentration, the rate at which the drug is to be infused based upon the concentration rate, the PCA dose, and the lockout period and an authorized clinician bolus can all be entered.

A sample programming display screen for the mode status 532 is illustrated in FIG. 29. An icon 533 illustrates the selected pumping mode. There the icon 533 stands for intermittent administration with bolus. Current pump operating status is shown at 534. The status of any alarms or alerts is shown at 536. The volume of solution remaining, volume of solution delivered, the dose rate, the keep vein open (KVO) rate, the bolus dose and the number of bolus doses tried and delivered are displayed at 537. It should be understood that the particular parameters displayed in the setup and status screen vary with the pump mode which is currently selected.

Figure 37A:
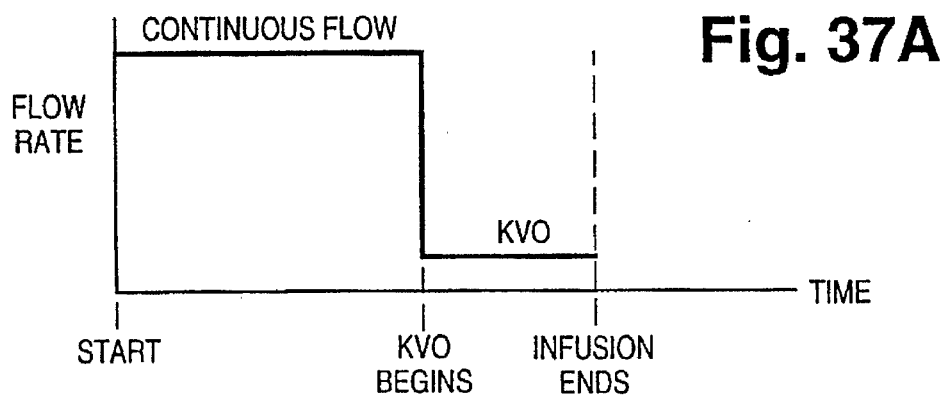
FIGS. 37A–E illustrate the five pump delivery profiles.

FIGS. 37A–E illustrate the five delivery profiles. Particularly, FIG. 37A illustrates the "continuous" flow profile. A continuous flow rate entered at the setup screen is administered for a time selected at the setup screen. Following the selected continuous flow, the pump delivers the KVO rate until the infusion ends.

Figure 37B:
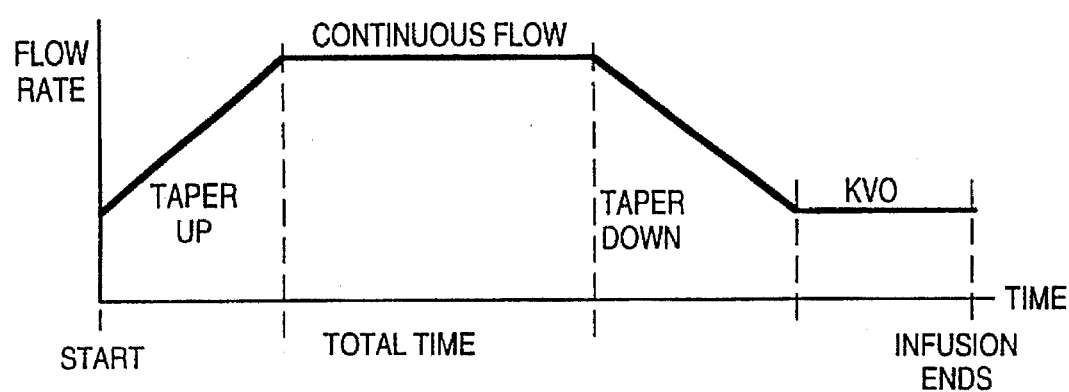

FIG. 37B illustrates the "continuous" flow with taper profile. The setup screen requires entry of the reservoir volume, total time of delivery, the taper up time, the taper down time, and the continuous rate of infusion. The monitor microprocessor calculates the taper up and taper down rates as follows. First, the continuous flow rate established between the taper up and taper down operations is calculated. The difference between the continuous flow rate and the KVO rate is divided by the number of minutes in the taper operation to obtain an mount that the rate will change each minute. For example, if the continuous flow rate is 140 ml/hr, the KVO rate is 20 ml/hr and the taper rate is sixty minutes, then the rate will change by 140–20/60 or two ml/hr for each minute. For taper up operation, the first minute the pump will deliver 22 ml/hr. At the end of the first minute, the pump will switch to a rate of 24 ml/hr., et cetera. This minute by minute rate stair step will continue until sixty minutes has elapsed and the continuous flow rate of 140 ml/hr. has been obtained. In a similar manner, the rate changes each minute to stair step down from the steady state flow rate to the KVO rate over the taper down time period. During each minute the rate is delivered in the manner normal for that rate within the pump. That is, one of flow modes 1–5, which corresponds to the required flow rate (see Section N below), is called by the main control routine.

Figure 37C:
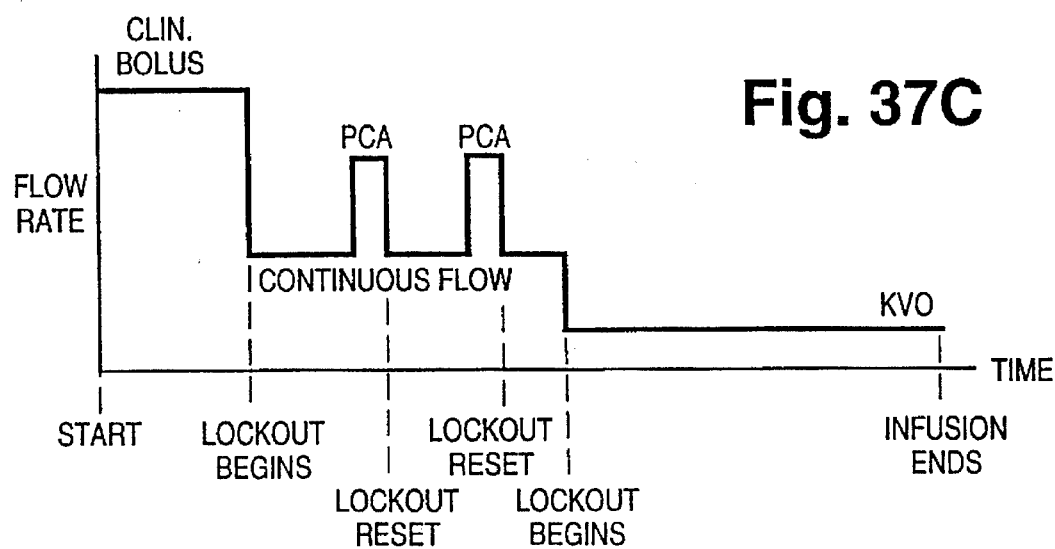

FIG. 37C illustrates the "continuous flow with PCA". At the setup screen, the user enters reservoir volume, concentration units, concentration rate, PCA dose, lockout period and clinician bolus. As seen in FIG. 37C, the clinician bolus is administered. Thereafter, a continuous flow is administered in accordance with the selected rate. During continuous flow, the patient may administer PCA dose through either the remote PCA button 44 or the PCA button 40 on the patient panel. Following administration of the PCA, the flow rate returns to the continuous flow rate and the lockout is reset. The patient is again prevented from administering PCA until the conclusion of the lockout period. The clinician bolus, continuous flow and PCA rates are delivered in accordance with the pump mode dictated by the required rate of flow. At the conclusion of the continuous flow period, delivery returns to the KVO rate.

Figure 37D:
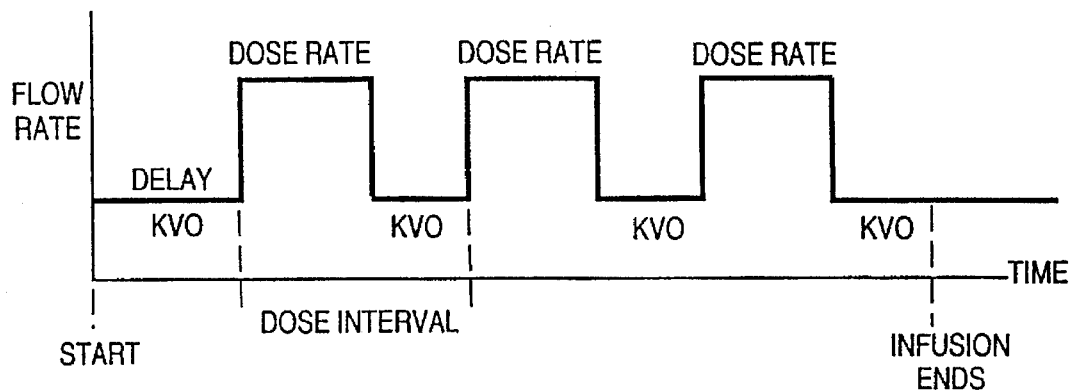

FIG. 37D illustrates the "intermittent delivery" profile. The setup screen requires entry of the reservoir volume, the dose rate, the time at dose rate, the KVO rate, the dose interval, the delay before start of the first dose administration and the start time. Between dose rates, the pump returns to the select KVO rate.

Figure 37E:
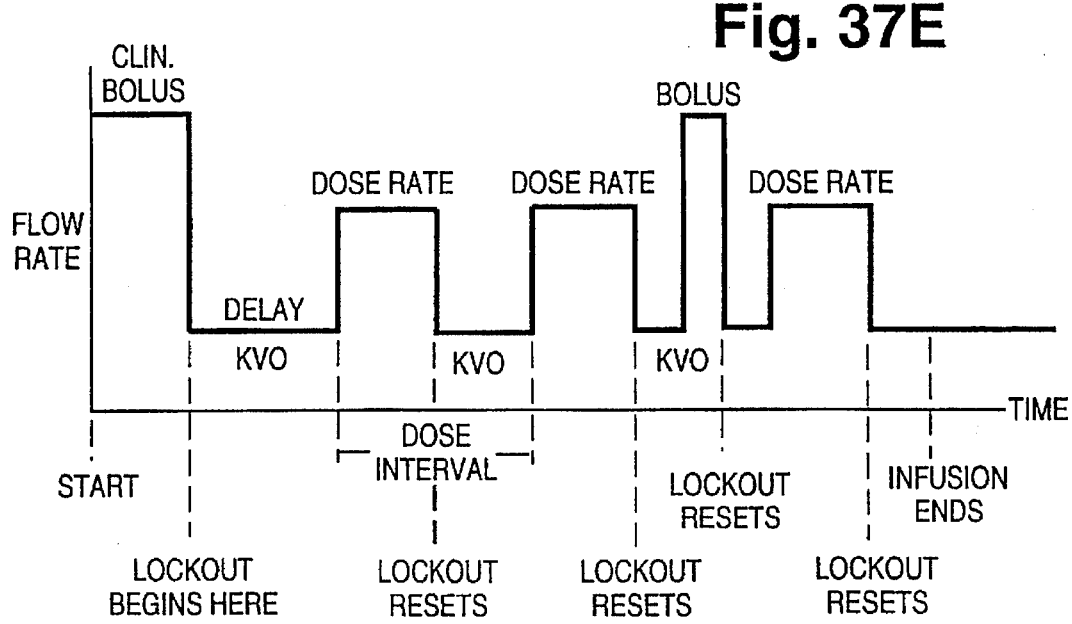

FIG. 37E illustrates the "intermittent with bolus" delivery profile. The intermittent with bolus delivery profile requires entry of the reservoir volume, the dose rate, the time at dose rate, the KVO rate, the dose interval, the allowed bolus dose, the lockout period, the delay period and, if desired, the clinician bolus. As illustrated in FIG. 37E, following the clinician bolus, the pump delivers at a KVO rate and a lockout period begins. At the conclusion of the lockout period, which can be of variable length, with a minimum value of 6 minutes, a bolus may be administered. The dose rate is administered after a set interval, following which the lockout period is again reset and a delivery is conducted at the KVO rate. Once the lockout period has again elapsed, a bolus dose may be again administered.

I. Programmer Controls

Figure 30:
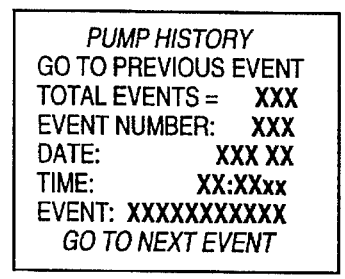
FIG. 30 is a plan view of the programming display with a sample "pump history" screen.

The keyboard 30 includes up/down buttons 522 which are used for scrolling between various delivery modes in the select delivery mode screen 516 illustrated in FIG. 27, scrolling between different input option 521 of a set-up screen 519 illustrated in FIG. 2 and for scrolling through values for each of the input option 521. A select key 523 allows selection of a delivery mode 517 scrolled to using the up and down keys 522, selection of an input option 521 for entry of a value or to deselect and enter a given value scrolled to using the up down keys 522 for a given input option 521. The finished program key 524 is used to enter a completed set-up screen 520 after entry of values for each selected input option. The edit/view key 525 allows a user to go from a mode status screen 532 of FIG. 29 to the setup screen 520 illustrated in FIG. 28. A Change Mode button 526 enables a user to go from the mode status screen 532 to the select delivery mode screen 516 of FIG. 27. The cancel key 527 cancels editing of a set-up screen 520 for a selected delivery mode and returns the programming display 28 to the last mode status screen. The history button 529 allows the clinician to view the history while the pump is in the standby state. A sample pump history screen 539 is contained in FIG. 30. The pump history displays such information as the total number of pumping events currently in the history log, an event number indicating what pump event is currently being viewed, date and time fields to indicate the date and time of the occurrence of the currently viewed event, and a description of the currently viewed event. The print button 530 can be actuated only when the pump is in the standby stage. The entire pump history can be printed by pressing the "print" button 530 once. Pushing the "print" button twice will cancel the print. The prime button 531 can be pressed following loading of the pump cassette into the pump for priming the pump. Pressing the prime button causes pumping of approximately 3.0 ml of fluid through the pump chamber.

J. Pumping Action

Operation of the plunger and valves to pump fluid through the pump chamber/valve assembly is best understood with reference to FIGS. 31 A–D. Each of FIGS. 31 A–D includes the pump platen 98; the pump/valve assembly 132, consisting of the pump chamber 140 and the inlet and outlet valve tubes 142,144; the inlet valve pincher 122; the outlet valve pincher 124; and the plunger 120. As discussed in Sections N2–6, combinations of movement of the plunger 120 and inlet and outlet valves 122,124, as illustrated in FIGS. 31A–D, provide a great degree of flexibility in delivery rates (0.1 ml/hr–390 ml/hr) and delivery profiles.

Figure 31A:
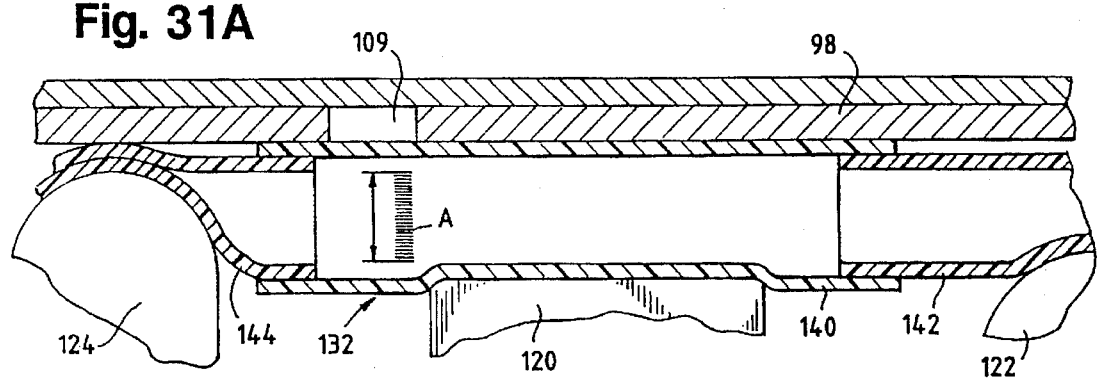
FIGS. 31A–D are sectional views illustrating the pumping action of the pump valves and plunger on the pump chamber/valve assembly.

FIG. 31A illustrates the pump chamber/valve assembly in a refill position with the outlet pincher valve 124 occluding the outlet valve to 144 and the inlet valve 122 open. The plunger 120 is in a fully retracted position, or position "–1". While fully retracted, the plunger 120 partially compresses the pump chamber 140. A scale "A" is included in FIG. 31A to represent 26 incremental advancements of the plunger 120, each advancement resulting from a revolution of the plunger motor 256.

Figure 31B:
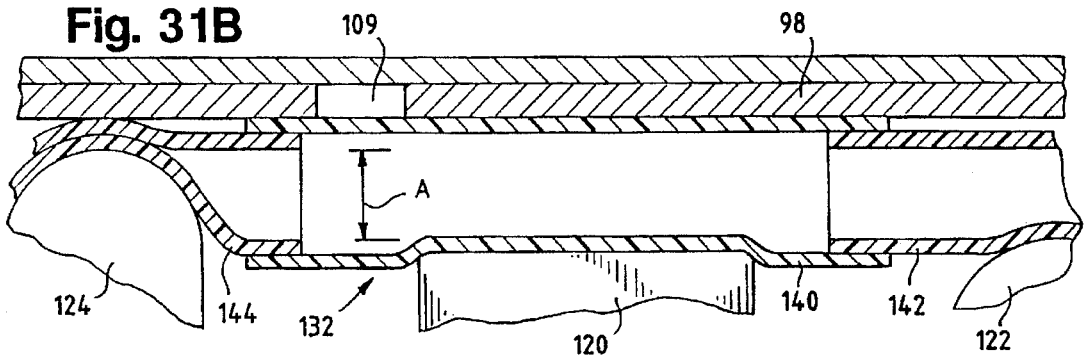

FIG. 31B illustrates the plunger advance one increment to position "0". Advancement of the plunger between the positions illustrated in FIG. 31A and FIG. 31B is known as a compensation step which is used to ensure that at position "0" the pump chamber is filled with a precise select amount of fluid.

Figure 31C:
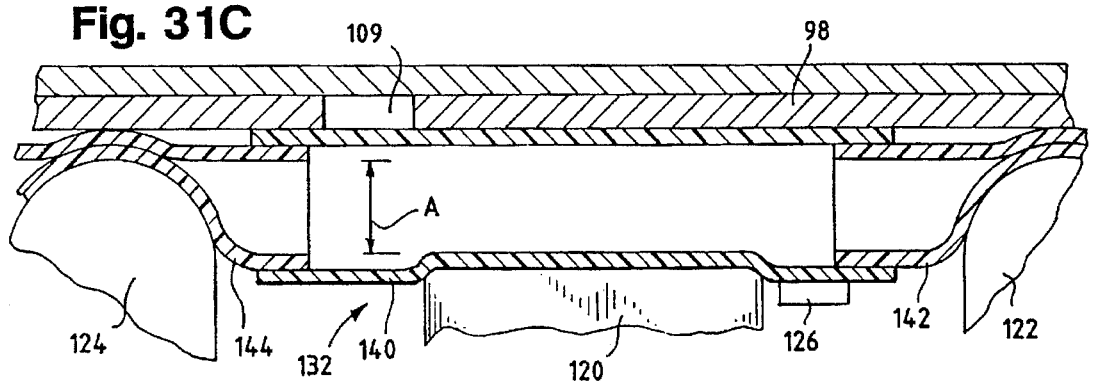

FIG. 31C illustrates a position of the valves and the plunger during a fill and valve leak test sequence. In this configuration, both the inlet and outlet pincher valves 122, 124 are extended to occlude the inlet and outlet valve tubes 142, 144 and the plunger 120 is advanced three motor revolutions so that pressure within the pump chamber can be measured by the transducer button wedge 126. The fill and valve leak test is described in greater detail in Section N.7.

Figure 31D:
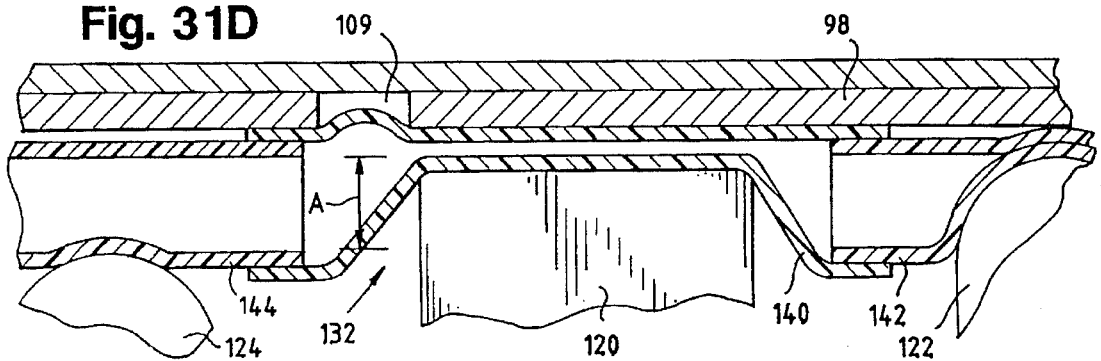

FIG. 31D illustrates the discharge of the pump chamber 140 with the outlet pincher valve 124 open and the inlet pincher valve 122 closed. In FIG. 31D the plunger 120 is illustrated at position "25", extended 25 increments or motor revolutions from the "0" or home position. With the plunger 120 fully extended, the pump chamber 140 is not fully compressed. As also viewed in FIG. 31D the pump chamber in FIG. 31D expands somewhat into the lengthwise hole 109 in the platen 98 so as to assure a more consistent pump discharge volume.

K. Pump Electronics

Figure 32:
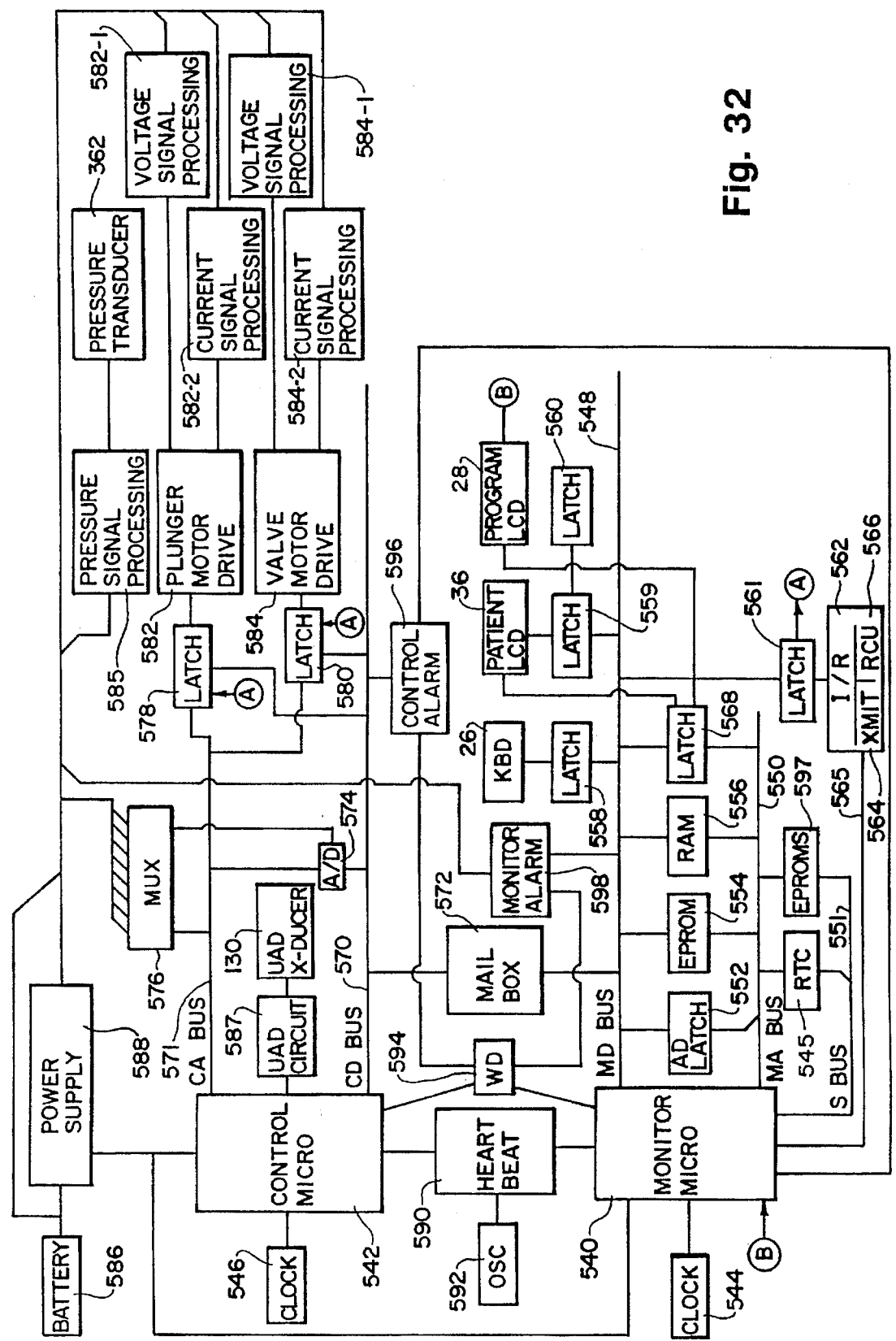
FIG. 32 is a block diagram of an electrical circuit for the ambulatory infusion pump.

With reference to FIG. 32, a block diagram illustrates an electrical circuit for the pump 10 of FIG. 1.

The pump incorporates a dual microprocessor design. The use of two microprocessors provides a great deal of design flexibility in structuring two different software packets to check and balance critical functions, and splits the work assignments on non-critical functions. The two processors have segmented functions, and different soil-ware, and are not running the same software in parallel. Their clocks are run at different frequencies to avoid errors related to single time base calculations. Critical functions, such as cam position timing signifying end of stroke, are predicted and checked by two different algorithms and software routines. The results must match, and serial communication must occur appropriately between the microprocessors to continue operation. Each microprocessor can stop the motors and sound an alarm if communications cease, are in error, or a fault condition is detected.

The two microprocessors comprise a monitor microprocessor 540 and a control microprocessor 542. Both microprocessors 540 and 542 may comprise, for example, type 87C528 single-chip eight bit microcontrollers. The monitor microprocessor 540 is connected to a clock circuit 544 operating at approximately 14.7 KHz. The control microprocessor 542 is connected to a clock circuit 546 operating at approximately 3.6 KHz.

The monitor microprocessor drives a monitor data bus 548, labeled "MD BUS", and a monitor address bus 550, labeled "MA BUS". An address decoder latch 552 connected to the MD BUS 548 develops additional addressing signals on the MA BUS 550. Memory circuits in the form of an EPROM 554 and RAM 556 are connected to both monitor buses 548 and 550.

A real time clock circuit 545 is connected to the MA BUS 550 and to the monitor microprocessor 540 via a serial bus 551 labeled S BUS and EEPROM circuits 597 are connected between the MA BUS 550 and the S BUS 551.

Four latch circuits 558, 559, 560 and 561 are connected to the MD BUS 548. The first latch circuit 558 may be a type 74HC541 latch circuit and is connected to the pump keyboard 26. The second latch circuit 559 may be a type 74H273 latch circuit connected to the patient LCD 36. The third latch circuit 560 may be a type 74HC541 latch circuit connected to the program LCD 28. The LCD 28 provides an LCD ready signal to the monitor microprocessor 540 via a node B. The fourth latch circuit 561 is connected to an infrared circuit 562. The infrared circuit 562 includes a transmit circuit 564 and receive circuit 566. The transmit circuit 564 includes an LED and conventional drive circuit for transmitting a carrier signal received on a line 565 from the monitor microprocessor 540 for remote communications. The receive circuit 566 receives infrared signals.

A further latch circuit 568 is connected to the MA BUS 550 for providing enable signals to the patient LCD 36 and program LCD 28.

The control microprocessor 542 drives a control data bus 570, labeled CD BUS, and a control address bus 571, labeled CA BUS. Communications between the control microprocessor 542 and monitor microprocessor 540 are implemented through a mailbox circuit 572 connected to the CD BUS 570 and MD BUS 548. The mailbox circuit 572 may comprise, for example, a type 74HC662 integrated circuit chip and associated logic circuits for implementing communication. Particularly, one of the microprocessors can send a message to the other microprocessor by sending the appropriate message to the mailbox circuit 572, where it will subsequently be read by the other of the microprocessors.

A conventional analog to digital (A/D) converter, such as a type MAX153 circuit, 574 is connected to the CD BUS 570 and CA BUS 571. The A/D converter 574 is connected to an analog multiplexer 576 such as a type 74HC4051 multiplexer circuit which is also connected to the CA BUS 571. The multiplexer 576 is connected to I/O devices as discussed below.

Additional latch circuits 578 and 580 are connected to the CD BUS 570 and CA BUS 571. The latch circuit 578 is connected to a plunger motor drive circuit 582. The latch circuit 580 is connected to the valve motor drive circuit 584. The latch circuits 578 and 580 may comprise, for example, type 74HC564 integrated circuits. The latch circuits 578 and 580 are also connected to the monitor latch circuit 561 for receiving an enable signal from the monitor microprocessor 540, as discussed below.

Each of the plunger motor drive circuit 582 and valve motor drive circuit 584 includes a conventional pulse width modulation (PWM) generator circuit for converting digital signals to a suitable pulse width modulated signal for driving the respective plunger motor 256 and valve motor 254, see FIG. 15. Particularly, the digital signal represents a duty cycle of motor input voltage on a zero to five volt scale. The operating frequency is approximately 68 KHz. Each PWM generator circuit in turn drives an H-bridge circuit for controlling voltage to the plunger motor 256 and valve motor 254. A voltage signal processing circuit 582-1 is connected to the plunger motor drive circuit 582 for detecting plunger motor voltage. A current signal processing circuit 582-2 is also connected to the plunger motor drive circuit 582 for detecting current drawn by the plunger motor 256. Similarly, a voltage signal processing circuit 584-1 is connected to the valve motor drive circuit 584 for detecting valve motor voltage. A current signal processing circuit 584-2 is also connected to the valve motor drive circuit 584 for detecting current drawn by the valve motor 254. The processing circuits 582-1, 582-2, 584-1 and 584-2 condition the detected signals which are input to the control microprocessor 542 via the multiplexer 576.

The pressure transducer 362, see FIG. 16, is connected via a pressure signal processing circuit 585 to the multiplexer 576 for providing input of sensed pressure. The ultrasonic air transducer 130 is connected via a processing circuit 587 to the control microprocessor 542.

Power for the pump 10 is provided by a 9 V battery 586 connected to a power supply circuit 588. The power supply circuit 558 includes suitable voltage regulator circuits for maintaining desired level of power to the control microprocessor 542 and monitor microprocessor 540 and other related circuits, as is well known. The battery 586 and power supply circuit 588 are also connected to the multiplexer 576 for feedback.

Because the pump 10 is powered solely by a battery 586, it is important that energy management schemes be used, as discussed above. In accordance with the invention, the microprocessors 540 and 542 include an idle mode and a power-down mode. In the idle mode, the processor puts itself to sleep while all of the on-chip peripherals stay active. Instruction to invoke the idle mode is the last instruction executed in the normal operating mode before the idle mode is activated. In the power-down mode, the oscillator is stopped and the instruction to invoke power-down is the last instruction executed. Each mode is terminated by an external interrupt received from a heartbeat circuit 590 connected to an oscillator 592. The processors 540 and 542 also wake themselves up from the idle mode by using internal timer interrupts. The heartbeat circuit 590 is configured to provide a pulse or heartbeat signal every 7.8125 msec. Upon receiving the heartbeat signal, each of the microprocessors 540 and 542 returns to the normal operating mode.

A watchdog circuit 594 is connected to each of the microprocessors 540 and 542. The watchdog circuit 594, as described below, operates with a sequence that verifies that the monitor microprocessor 540 produces a "monitor OK" pulse and subsequently the control microprocessor 542 produces a "control OK" pulse, then followed by a "monitor OK" pulse, etc., and that these pulses are at the correct time intervals.

The watchdog circuit 594 is also connected to each of a control alarm 596 and monitor alarm 598. The control alarm 596 is connected to the CD BUS 570. The monitor alarm 598 is connected to the MD BUS 548. The control alarm 596 provides a control alarm feedback signal to the monitor microprocessor 540. The monitor alarm 598 provides a monitor alarm feedback to the control microprocessor 542 via the multiplexer 576.

Figure 33:
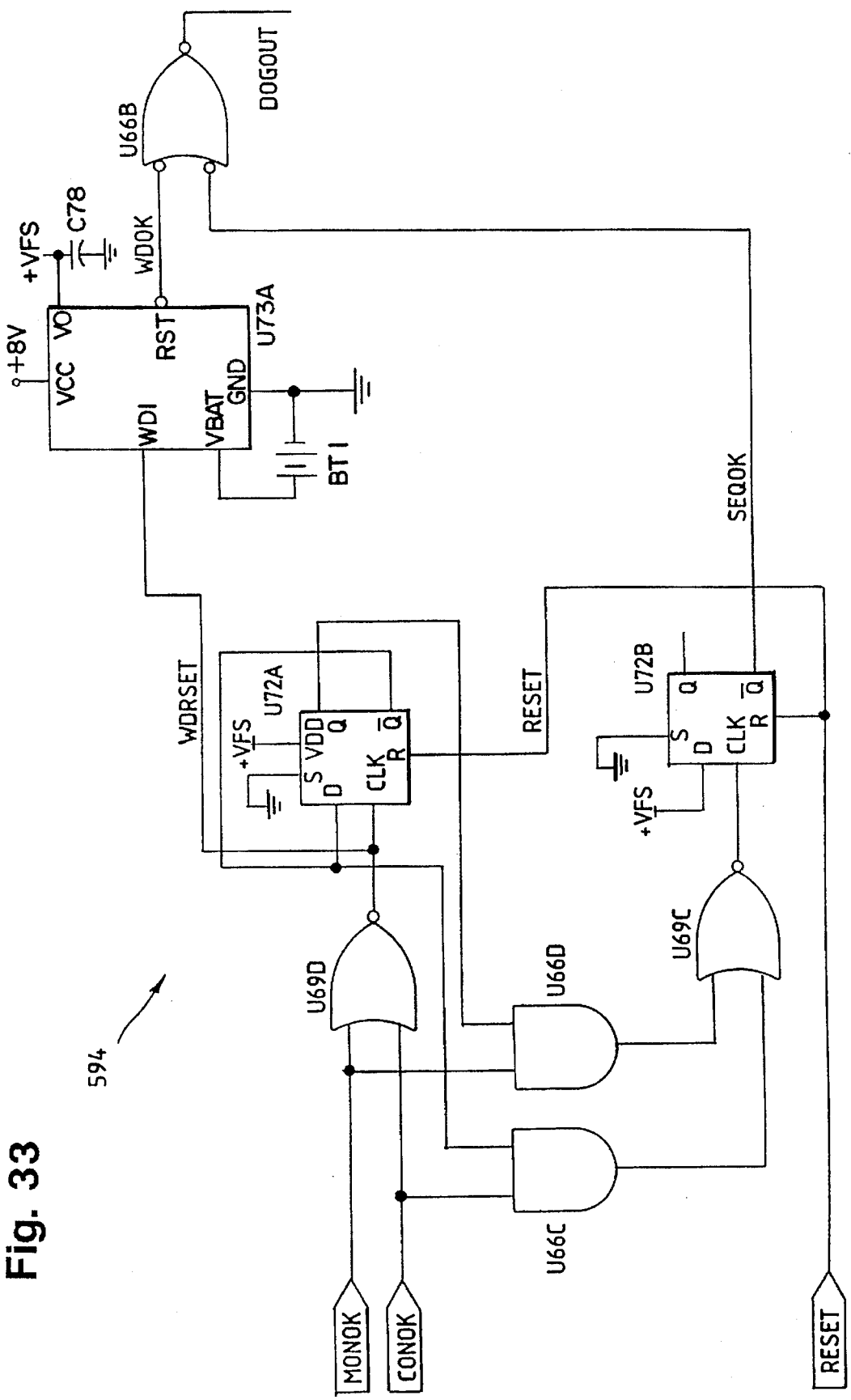
FIG. 33 is an electrical schematic for a watchdog circuit of the ambulatory infusion pump.

With reference to FIG. 33, an electrical schematic for the watchdog circuit 594 is illustrated. The watchdog circuit 594 receives a monitor watchdog reset, or OK signal, labeled MONOK from the monitor microprocessor 540, a control watchdog reset, or OK signal from the control microprocessor 542, labeled CONOK, and a reset signal from the power supply 588. Each of the CONOK and MONOK signals are connected to inputs of a negative OR NOR gate U69D. The MONOK signal is also supplied to one input of an AND gate U66D. The CONOK signal is also applied to one input of an AND gate U66C. The output of the NOR gate U69D is the clock input of a flipflop U72A. The inverted output of the flipflop U72A is fed back to its data input as well as the second input of the AND gate U66C. The non-inverted output of the flipflop U72A comprises the second input of the AND gate U66D. The output of the AND gates U66C and U66D comprise inputs to a NOR gate U69C, the output of which is connected to the clock input of a flipflop U72B. The data input of the flipflop U72B is connected to a plus voltage failsafe input. The inverted output of the flipflop U72B comprises a sequence OK signal coupled to an inverted input of an AND gate U66B.

The watchdog circuit 594 also includes a timer circuit U73A in the form of a monostable multivibrator, such as a type MAX 690A integrated circuit. The timer U73A, at a WDI input, receives a watchdog reset signal from the output of the NOR gate U69D. An inverted RST output of the timer U73A is coupled to the second inverted input of the AND gate U66B.

The watchdog circuit 594 operates as a state machine having three states—waiting for a MONOK signal, waiting for a CONOK signal and sequence violated. The circuit 594 alternates between the waiting states unless the alternating sequence is violated or unless the alternating sequence did not begin with the MONOK signal. In that case, the circuit enters the sequence violated state.

The operation of the watchdog circuit 594 is as follows. As long as the output of the AND gate U66B is high, then the microprocessors 540 and 542 are indicated to be operating properly. A watchdog trip occurs either if no OK signal is received within 3.2 seconds, or the OK signals are out of sequence. Particularly, the OK sequence must alternate between the MONOK and the CONOK signal.

At startup, the inverted output of each flipflop U72A and U72B is high due to reset. Similarly, the output of the timer circuit U73A is high, so that the output of the AND gate U66B is high. With the inverted output of the flipflop U72A high, the AND gate U66C is enabled. Because the non-inverted output of the flipflop U72A is low, the AND gate U66D is disabled. The first pulse received should be the MONOK signal from the monitor microprocessor 540. Assuming the pulse is received, the pulse is applied to the second AND gate U66D, which has been disabled. The output of the NOR gate U69D clocks the flipflop U72A so that the outputs alternate. This has the effect of enabling the AND gate U66D and disabling the AND gate U66C. Assuming the next pulse received is the CONOK pulse, then the pulse is applied to the NOR gate U69D, which again clocks the flipflop U72A and is also applied to the disabled AND gate U66C. If consecutive pulses are received from the same processor, then such occurrence will be detected by one of the AND gates U66C or U66D. For example, if the AND gate U66C is enabled, indicating that the last pulse received was the CONOK pulse, and another CONOK pulse is received, then the output of the AND gate U66C goes high, causing the NOR gate U69C to clock the flipflop U72B so that its inverted output goes low, causing the output of the AND gate U66B to go low to indicate a watchdog error condition. Similarly, if two consecutive MONOK pulses are received, then the output of the AND gate U66D goes high to clock the flipflop U72B through the NOR gate U69C.

The watchdog circuit 594 otherwise detects a failure if no pulse is received every 3.2 seconds. Particularly, when either the MONOK or CONOK signal pulses the NOR gate U69D, that pulse is used to reset the timer circuit U73A. If no pulse is received for 3.2 seconds from either the MONOK or CONOK inputs, then the timer U73D output to the AND gate U66B goes low, so that the DOGOUT output of the AND gate U66B goes low to indicate a watchdog failure. A watchdog failure results in a reset signal being sent to the microprocessors 540 and 542. Also, a watchdog failure disables the plunger motor drive 582 and the valve motor drive 584, via the respective latch circuits 578 and 580. Disabling the motors stops all pumping action, leaving one of the pump chambers tube ends pinched.

L. System Peripherals

Figure 39:
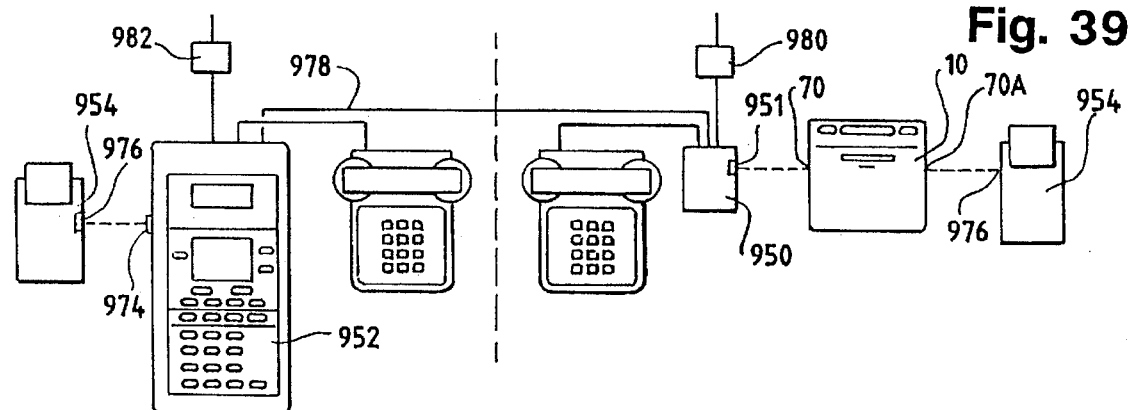
FIG. 39 is a schematic representation of the pump peripherals communicatingly associated.
Figure 40:
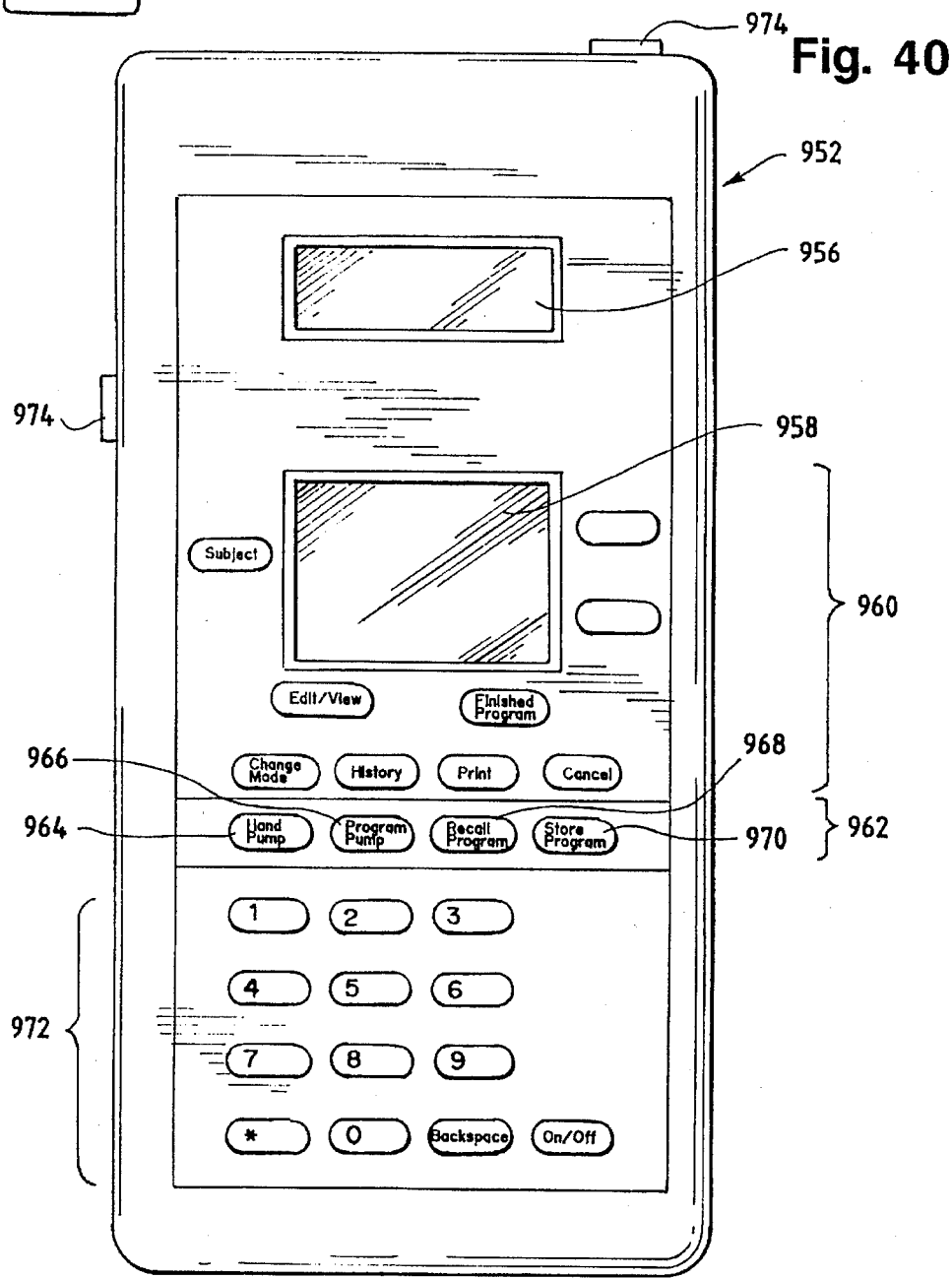
FIG. 40 is a plan view of the remote programmer unit.

The ambulatory infusion pump 10 is part of a system illustrated in FIG. 39 which includes, in addition to the soft pump case 12, the solution bag 64, the pump cassette 86 and the PCA switch 44, a remote communication interface unit 950, remote programmer 952 and a printer 954.

Figure 41:
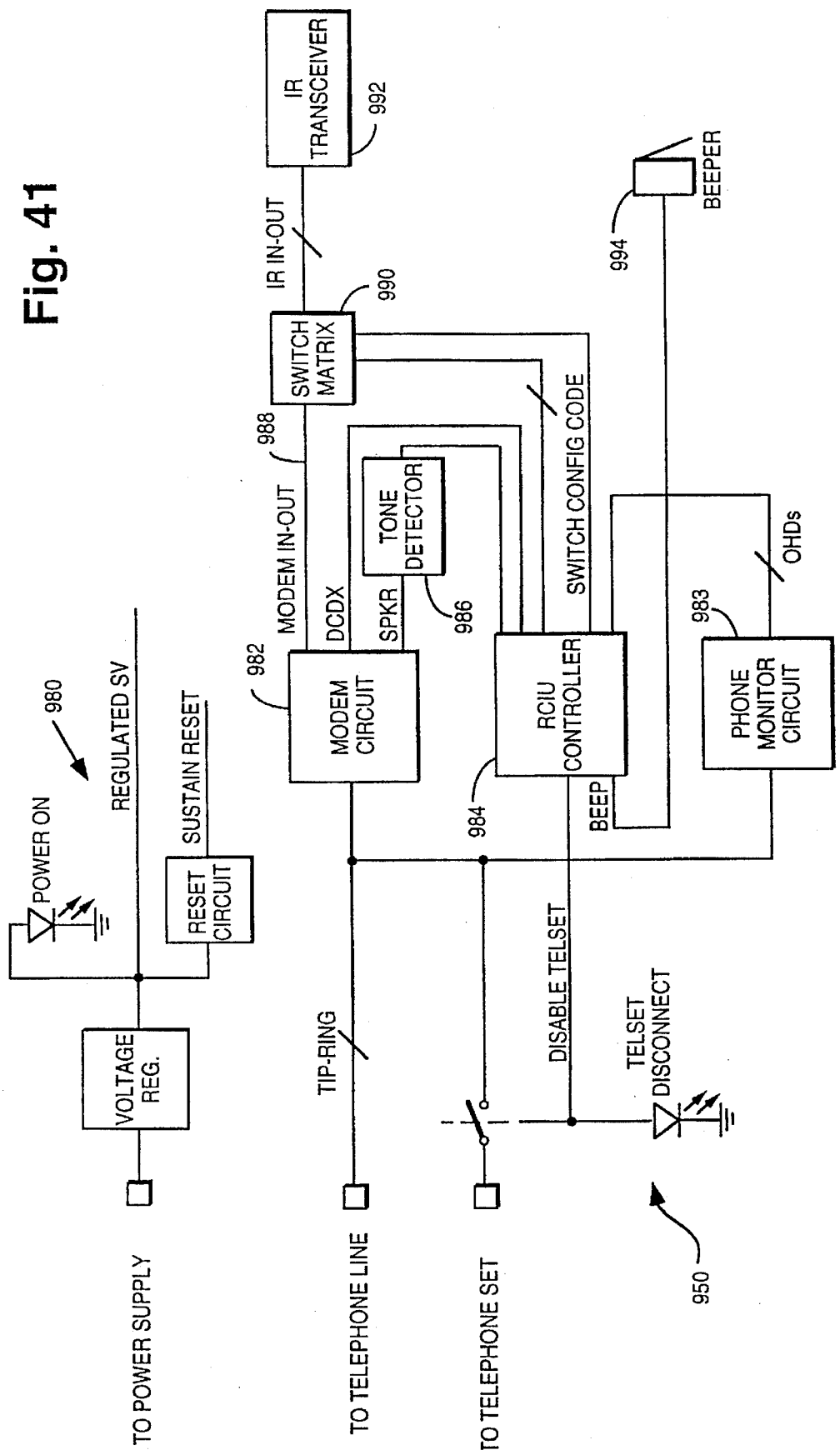
FIG. 41 is a block diagram of an electrical circuit for a remote communication interface unit for use with the ambulatory infusion pump.

The RCIU 950 consists of a telephone modem and an IR input/output 951. A block diagram of the RCIU is illustrated in FIG. 41. With reference to FIG. 41, a block diagram illustrates a circuit for the RCIU 950, see FIG. 39. The RCIU is a telephone to modulated infrared transceiver acting as an interface between a local pump 10 and remote programmer 952, as illustrated in FIG. 39. Particularly, the pump 10 is adapted to receive infrared signals for remote programming. When the remote programmer 952 is physically remote, it cannot directly transmit IR signals to the pump 10. In that instance, the programmer 952 transmits programming information over commercial phone lines to the RCIU 950, which converts the information to infrared signals to the pump 10, and vice versa.

The RCIU 950 includes a power supply circuit 980 for powering the various circuit components. A modem circuit 982 is connected to the telephone line, as is a phone monitor circuit 983. The modem circuit 982 is connected to a tone detector 986 which provides an answer tone detected signal to an RCIU controller 984. The modem circuit 982 has a data line 988 connected to a switch matrix 990. The switch matrix 990 is also connected to an IR transceiver circuit 992 and to the RCIU controller 984. The RCIU controller is also connected to a beeper 994.

The specific circuitry for the RCIU 950 is conventional in nature and therefore is not described in detail herein. Particularly, the RCIU controller acts as a conventional modem to initiate or receive "phone calls" to a remote programmer 952, see FIG. 39. Communication is established in a conventional manner. Once communication is established, then the RCIU controller 984 controls operation of the switch matrix 990 to receive data either over the phone line via the modem circuit 982 or via the IR transceiver circuit 992, converts the received data to the other format, i.e., IR to modem or vice versa, and then transmits the received data in the converted format via the opposite media from which it was received.

The remote programmer 952 includes a status LCD 956 and a program LCD 958. The program LCD 958 is identical to the program LCD 28 of the ambulatory infusion pump 10. The remote programmer also includes a keyboard 960 which is identical to the keyboard 30 of the ambulatory infusion pump 10. In addition, the remote programmer includes a number of numeric entry controls 962 which simplify programming via the remote programmer. An IR input/output device 964 is provided for communication with the IR window 70 of the ambulatory infusion pump 10 and the IR input/outputs of the RCIU 950.

Figure 34:
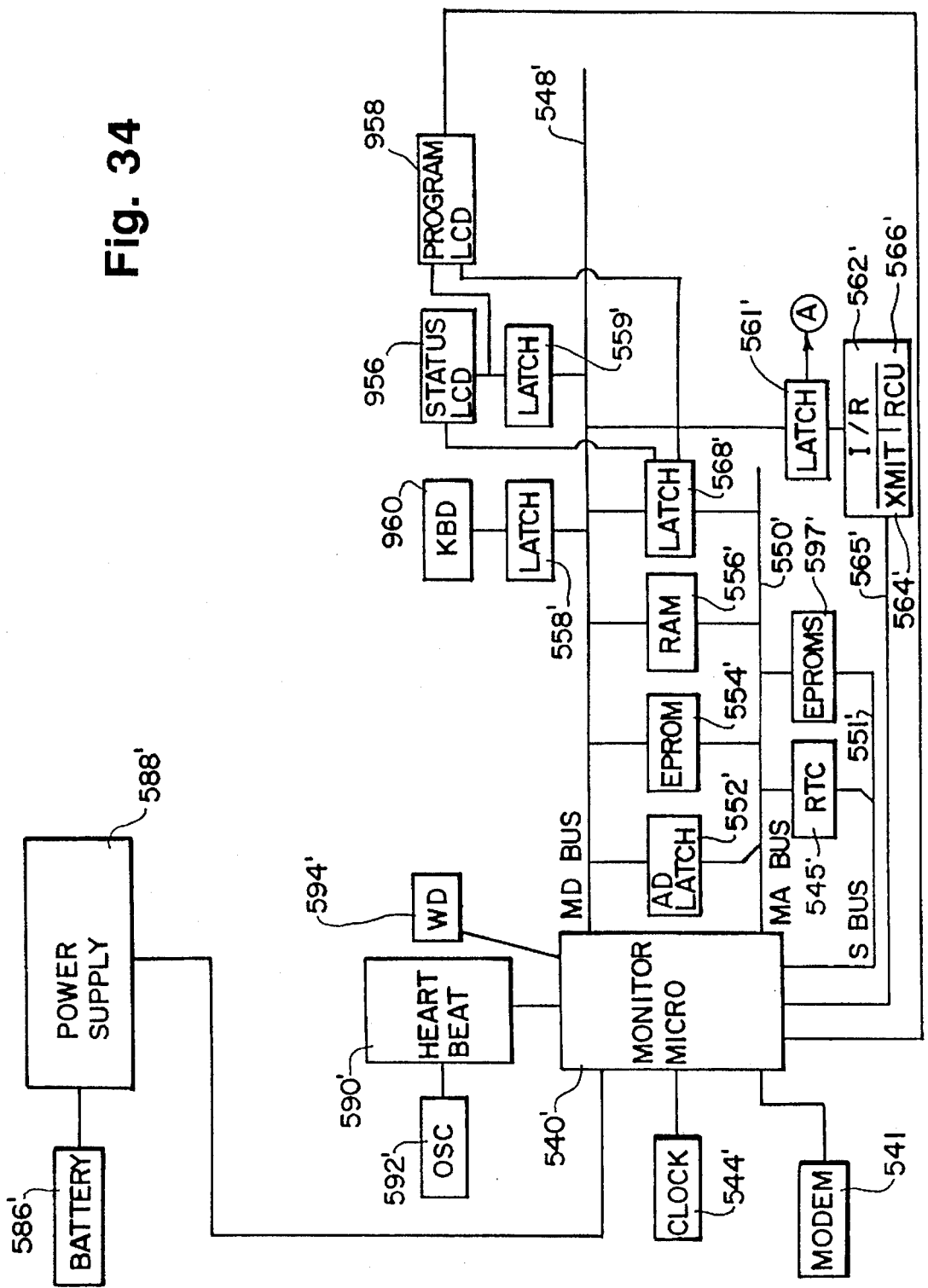
FIG. 34 is a block diagram of an electrical circuit for the remote programmer.

With reference to FIG. 34, a block diagram illustrates an electrical circuit for the remote programmer 952. The circuit is essentially a duplicate of the circuit associated with the monitor microprocessor 540, see FIG. 32. Therefore, the circuit is not described in detail herein. For simplicity, like elements are indicated with like, primed reference numerals. Among the differences are the addition of an internal modem circuit 541 connected to the monitor microprocessor 540'. The modem circuit 541 may include, for example, a type CH1782 modem circuit module. Also, the patient LCD is replaced with the status LCD 956. Both the status LCD 956 and program LCD 958 are connected to the latch circuit 559'. Also, a conventional microprocessor watchdog 594' is used.

The printer 954 is a standard printing device having an IR input/output 966.

FIG. 39 illustrates remote programing use of the remote programmer 952 and the RCIU 950. Communication may be transmitted over commercial phone line 966. The RCIU 950 is located in the immediate vicinity of the pump and is powered by an AC adaptor 970. An IR window 70 of the pump is maintained within approximately six inches of an IR input/output 951 of the RCIU 950. The printer 966 may be linked to a second IR window 70A of the pump 10. At the remote location, the remote programmer 952 is connected directly to the commercial phone line 968. It is powered by an AC adaptor 972. A printer 954 having an IR input/output 966 is maintained in infrared communication with an IR input/output 964 of the remote programmer 952. The programmer 952 can be used for direct wireless programming of the pump by positioning the programmer with its IR input/output 964 in direct IR communication with the IR window 970 of the pump 10 and programming and access to pump data can be conducted in the manner discussed below in Section M4 with respect to FIG. 35D.

M. Monitor Microprocessor Software

As set forth above, the ambulatory infusion pump includes a monitor microprocessor 540 and a control microprocessor 542. The monitor microprocessor and its software generally supports programming, user interface, communication and peripheral hardware with execution of the pumping sequence by the control microprocessor. The flow diagram of FIG. 35A comprises a generalized flow diagram representing the main routine of the monitor microprocessor software. FIGS. 35B-D represent sub-routines called by the monitor microprocessor main routine.

1. Main Monitor Routine

The monitor microprocessor main routine begins at block 620, which represents a user powering on the pump, at which time initialization of the monitor main routine and self-test routines are performed. The self-tests includes RAM test, ROM test, integrity of delivered program, communication between the control and monitor microprocessors and test of the pump beeper and visual alarms. Block 622 represents a routine for supporting the programmer display and the programmer controls. A detailed flow diagram of block 622 is provided in FIG. 35B. Supports for the patient display and the patient controls is provided at block 624. This includes drawing of the patient display such as that illustrated in FIG. 26 and support for the on/off control 38 and the bolus dose control 40 shown in FIG. 25. At block 626 support is provided for the beeper and patient LED which provide both indication of normal pump operation and, under circumstances described below, error notification. Communication with the control microprocessor is conducted at block 628 which is shown in greater detail in the flow diagram of FIG. 35C.

At block 630 the routine determines whether or not the pump is currently delivering a therapy. If not, printer support is provided at block 632. The printer support controls printing of historical data and other operating parameters. Communication with the remote programmer is supported at block 634. A detailed flow diagram of the substantive controlling communication support with the remote programmer is contained in FIG. 35D. The monitor microprocessor is put to sleep at 636. The monitor microprocessor remains asleep until block 638, whereat the next heartbeat awakens the monitor microprocessor and the main routine continues.

Returning to decision block 630, if the pump is delivering a therapy, decision block 640 is reached and a determination is made whether the program entered at block 622 has been mapped by the monitor microprocessor. If it has not, the program is mapped at block 642. At block 642, the monitor microprocessor generates two program maps: a monitor program map and a control program map. The monitor program map contains a series of operations necessary to administer the delivery profile entered at block 622 in the manner described with reference to FIG. 35B. Following compilation of the monitor and control program maps, the monitor program map is executed at block 644. Of course, if the program maps have already been compiled, block 644 is reached directly following decision block 640. If the monitor program map requires actuation of the pump mechanics, an appropriate command is generated and flagged at block 644. The flag is subsequently detected at block 628 and communication with the control microprocessor is conducted in the manner discussed with reference to FIG. 35C. In a like manner, if a control program map is constructed in block 642, it is flagged and communicated to the control microprocessor at block 628.

2. Support Programmer Display and Controls Routine

With reference to FIG. 35B, a flow diagram illustrates the support programmer display and programmer controls of block 622. In describing the support programmer display and programmer control, typical programming sequences are discussed. It should be noted, however, that at those blocks described below where the user is assumed to have taken action, such as block 654 where the user positions the cursor with the "up" and "down" keys, the user may instead press the "cancel" button, thus returning to the previously selected mode screen or the user may do nothing at all, essentially leaving the pump in limbo.

At block 648 the current mode screen is drawn, such as the "intermittent with bolus" mode screen shown in FIG. 29. As discussed with reference to FIG. 27, five delivery modes 517 are available: "continuous", "continuous with PCA", "continuous with taper", "intermittent" and "intermittent with bolus". These delivery modes are discussed in greater detail in Section H above with reference to FIG. 37A-E.

At decision block 650 determination is made whether or not a user has depressed the "change mode" button 526. If the "change mode" button 526 has been pressed, SELECT DELIVERY MODE screen illustrated at FIG. 27 is drawn at block 652. At block 654, the user positions the cursor with the up and down keys 522 to highlight with the cursor the intended delivery mode. The user presses the "select" button 523 at block 656 when the desired delivery mode has been highlighted by the cursor. The mode screen for the selected mode is then drawn at block 658, following which the main routine is resumed.

If at decision block 650 the "change mode" button 526 has not been pressed, at block 660 the routine determines whether the "edit/view" button 525 has been pressed. Pressing of the "edit/view" button allows the user to enter new parameters for the selected delivery mode. At block 662 the "setup" screen is drawn for the selected delivery mode. A sample "setup" screen is illustrated at FIG. 28. At block 664 the user positions the cursor with the "up" and "down" keys 522 for the purpose of entering or altering one of the input options 521.

The program includes a lockout feature to prevent unauthorized or inadvertent alteration of selected input options. A clinician can prevent alteration of selected input options without input of a selected password or code where restricted access to an input option is necessary for patient safety. The feature is controlled by a clinician entering a selected lock level which tells the program whether a particular input option can be altered. If the input option can be altered, the input option line, including the input valves, is highlighted when the cursor is positioned at the particular input option. This highlighting is known as a "regular cursor" and is illustrated at 665 of FIG. 28. If the input option cannot be altered, only a vertical line or "edge cursor" to the immediate left of the input option will be highlighted when the cursor is positioned at that particular input option, as illustrated at 665A of FIG. 28.

At decision block 666 the routine determines whether the user is in lock level "0", which allows unrestricted access. If the user is in lock level "0", the regular cursor is drawn at block 668. If the user is not in lock level "0", at decision block 669 the routine determines whether the new cursor position or input option is lock level protected. If it is not, at block 668 the regular cursor is produced. If the cursor position or input option is lock level protected, at block 670 the edge cursor is produced.

Returning to block 668, if the regular cursor is produced at block 672, the routine inquires whether the user has pressed the "select" key 523. If not, the user may reposition the cursor with the "up" and "down" keys 522 at block 664. If the user has pressed the "select" key 523, the user may then modify the input value parameter with the "up" and "down" keys 522 at block 674. When a desired value is arrived at block 674, the user presses the "select" key 523 at 676. The routine then simultaneously "deselects" the input option retracting the cursor, and "enters" the modified value. Block 678 represents three user options. The user may return to block 664 and reposition the cursor with the "up" and "down" keys 522. Or, the user may press the "cancel" key 527, block 679, deleting the new program. The previous "mode" screen will then be drawn at block 680 with the input option values unchanged. The main routine is then rejoined at block 624. The third option shown at block 682 is for the user to press "finished program". The new "mode" screen with the newly selected values is then drawn at 684. The main routine is then rejoined at block 624.

3. Support Communication with Control Microprocessor Routine

Figure 35A:
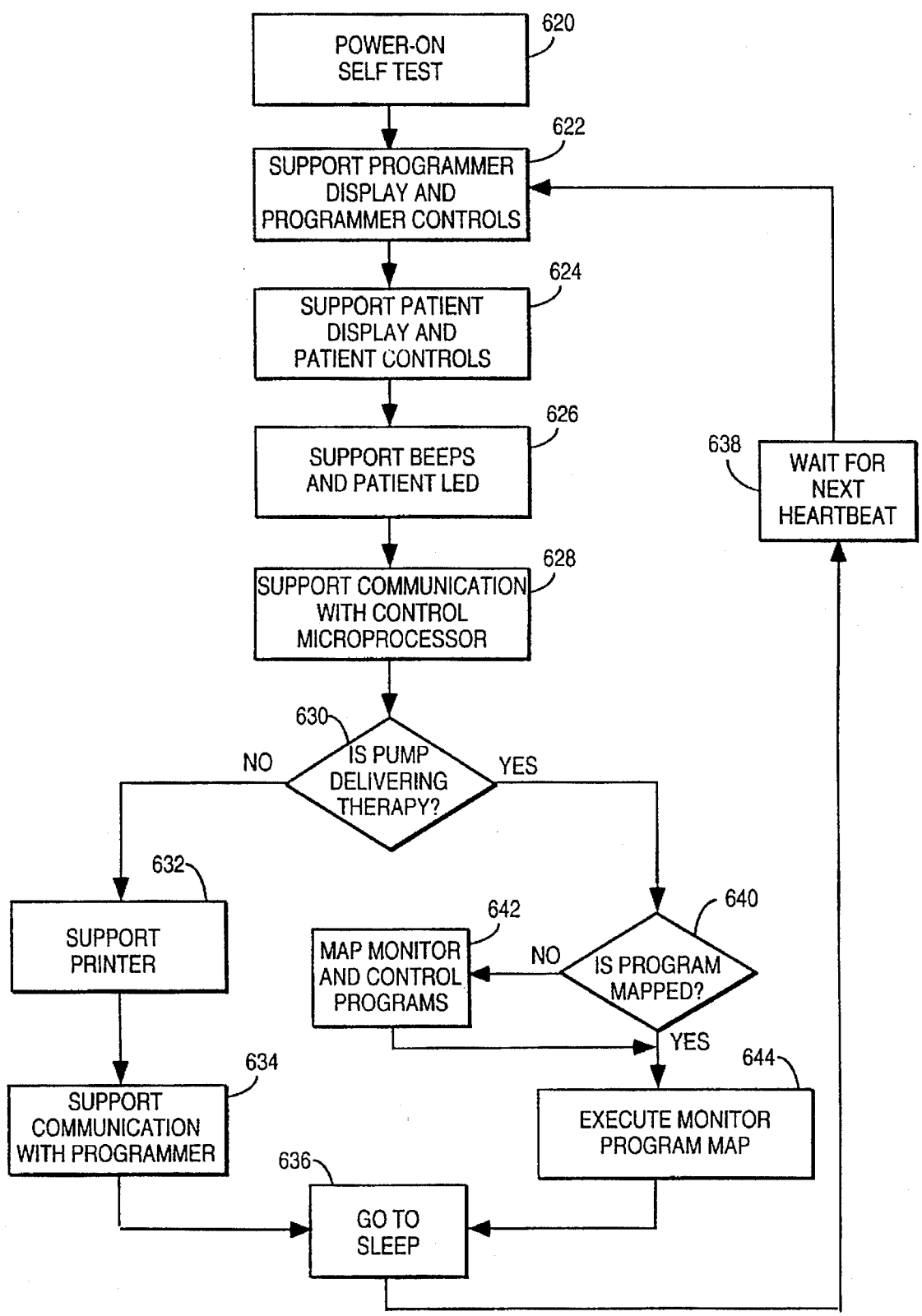
FIG. 35A is a flow diagram of the main routine of the monitor microprocessor software for use with the ambulatory infusion pump.
Figure 35B:
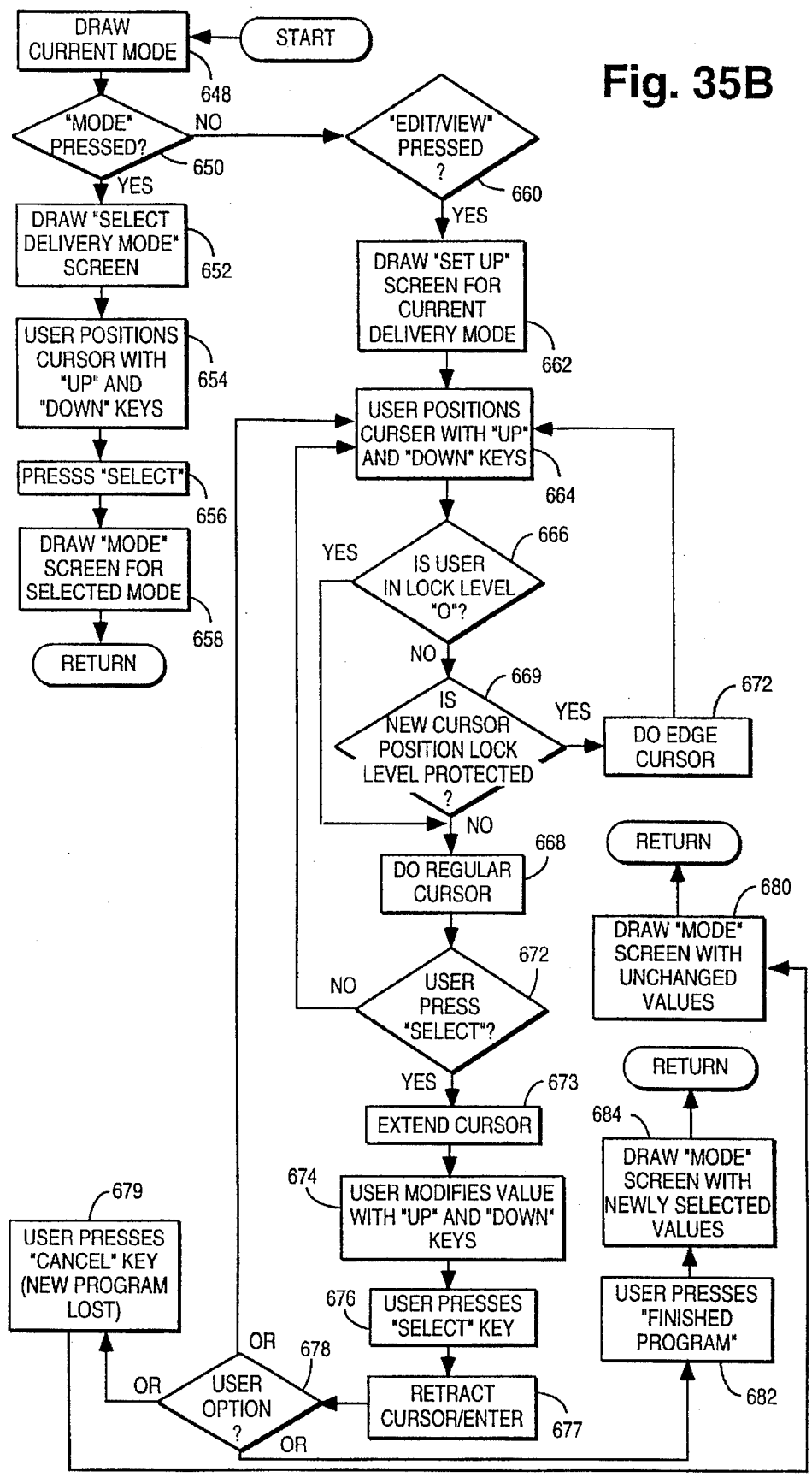
FIG. 35B is a flow diagram of the "support patient display and patient controls" subroutine of FIG. 35A.
Figure 35C:
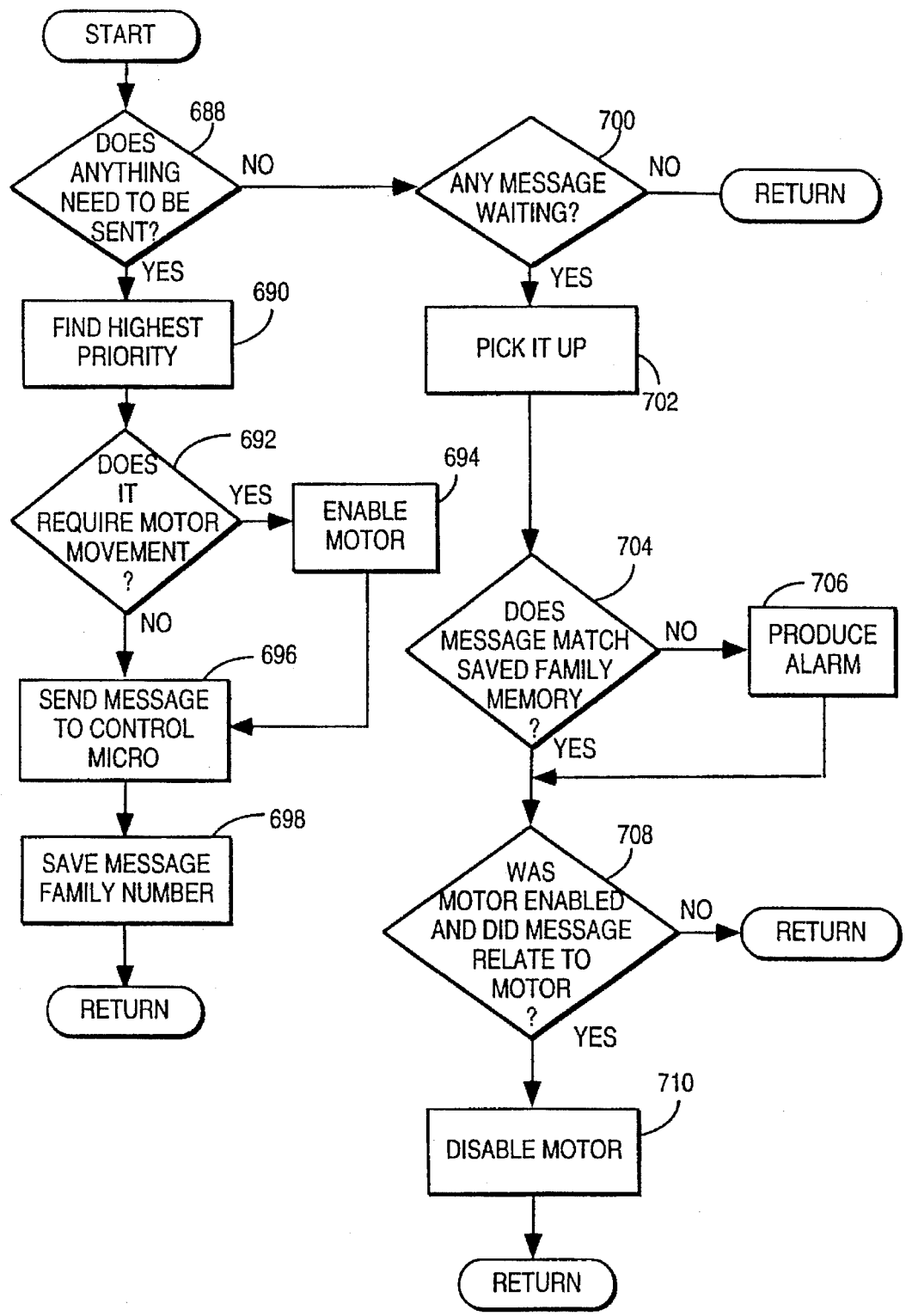
FIG. 35C is a flow diagram of the "support communication with control microprocessor" subroutine of FIG. 35A.
Figure 35D:
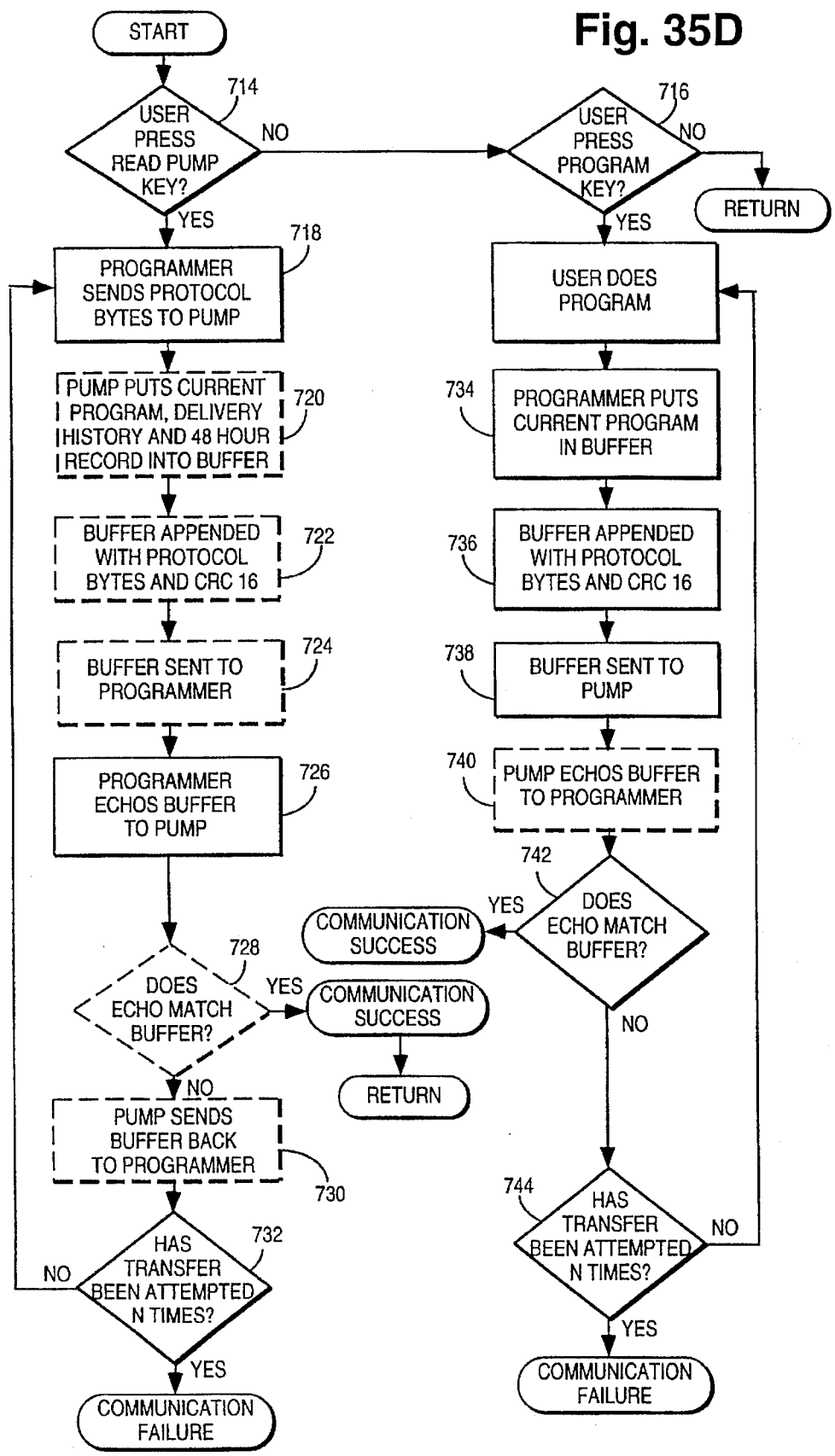
FIG. 35D is a flow diagram of the "support communication with the remote programmer" subroutine of FIG. 35A.

FIG. 35C is a flow diagram illustrating in detail block 628 of FIG. 35A, "support communication with control microprocessor". Communication begins at control block 688, where the routine determines whether a flag or flags have been raised at the "execute monitor program map" block 644 or the "program map" block 642 of the main monitor routine, FIG. 35A. If such a flag has been raised, then the highest priority message will be found at block 690. At decision block 692 determination is made whether the message to be sent requires movement of either the plunger motor or the valve motor. If the answer is yes, the appropriate motor is enabled at block 694. At block 696, the message is then sent to the control microprocessor. At block 698, the message family number is stored. The family number will subsequently be compared with a confirming message conveyed by the control microprocessor as discussed below.

If at decision block 688 there is no message to be sent, at decision block 700 the routine determines whether any message is waiting from the control microprocessor. If no message is waiting, the main monitor microprocessor routine simply continues. If a message is waiting from the control microprocessor, the message is picked up at block 702. At decision block 704 it is determined whether the message picked up matches the message saved at block 698. If the message does not match, an alarm is produced at block 706. Whether the motor had been enabled and whether the picked up message relates to the motor is determined at block 728. If the answer to both questions is yes, the motor is disabled at block 710 and the subroutine returns to the main routine. If the answer is no, the subroutine returns directly to the main routine.

4. Support Communication with Remote Programmer Routine

FIG. 35D is a flow diagram illustrating the "support communication with the remote programmer" subroutine of block 634 of the main monitor routine. Those steps being performed by the remote programmer 952 are shown in solid lines, and those being performed by the monitor microprocessor are shown in dotted lines. Communication between the remote programmer and the pump is conducted in one of three ways detailed in Section L above: 1) directly by infrared linkage; 2) through the remote communication interface unit (RCIU); or 3) by linkage to the remote programmer through a local RCIU, an RCIU at the remote programmer location and phone lines. At decision block 714 the routine determines whether the user has pressed the "Read Pump" key 964 of the remote programmer. If not, at decision block 716 determination is made whether the user has pressed the "Program Pump" key 966. If the answer is no, the routine returns to the main monitor routine and the monitor microprocessor is put to sleep at block 636 (see FIG. 35A).

If at decision block 714 the user has pressed the "Read Pump" key 964, the remote programmer sends protocol bytes to the pump at 718. The protocol bytes include, for example, the respective serial numbers of the pump and remote programmer. At block 720, the monitor microprocessor puts the current program, delivery history and previous forty-eight hour record into a buffer. At block 722, the monitor microprocessor appends the protocol bytes and CRC 16 to the buffer. At block 724, the buffer is sent by the monitor microprocessor to the remote programmer. At block 726, the remote programmer echoes the buffer to the remote microprocessor. At decision block 728, the monitor microprocessor determines whether the buffer echoed at box 726 matches the buffer sent to the remote programmer at box 724. If the answer is yes, the communication is a success and the monitor microprocessor continues the main routine at block 636 of FIG. 35A. If the echo does not match the buffer, at block 730 the pump monitor microprocessor sends the buffer back to the remote programmer. At decision block 732 the remote programmer determines whether the transfer has been attempted a select number, or n times. If it has and the echo fails to match the buffer sent by the monitor microprocessor of the pump, there is a communication failure and an alarm is sounded. If at decision block 732 the remote programmer microprocessor determines the transfer has not been attempted n times, the routine returns to block 718 and is repeated until the echo matches the buffer or transfer has been attempted unsuccessfully n times.

If the user has pressed the "Program Pump" key 966 at decision block 716, the remote programmer puts the current programmer in a buffer. At block 736, the buffer is appended with the protocol bytes e.g., pump and programmer serial numbers and CRC-16. At block 738, the buffer is sent to the pump. At box 740, the pump monitor microprocessor echoes the buffer to the remote programmer. At decision block 742, the remote programmer determines whether the echo matches the buffer sent to the pump. If the answer is yes, the communication is a success, and the main routine of the monitor microprocessor is continued, with the new program being implemented in the same manner as if the program had been entered directly at the pump. If the echo does not match the buffer, at decision block 744 the determination is made whether the transfer has been attempted a select number or n times. If it has not, the routine continues at box 734 and repeats itself until the echo does match the buffer or the transfer has been attempted a n number of times, at which time communication is a failure and an alarm is sounded.

N. Control Microprocessor Software

Figure 36A:
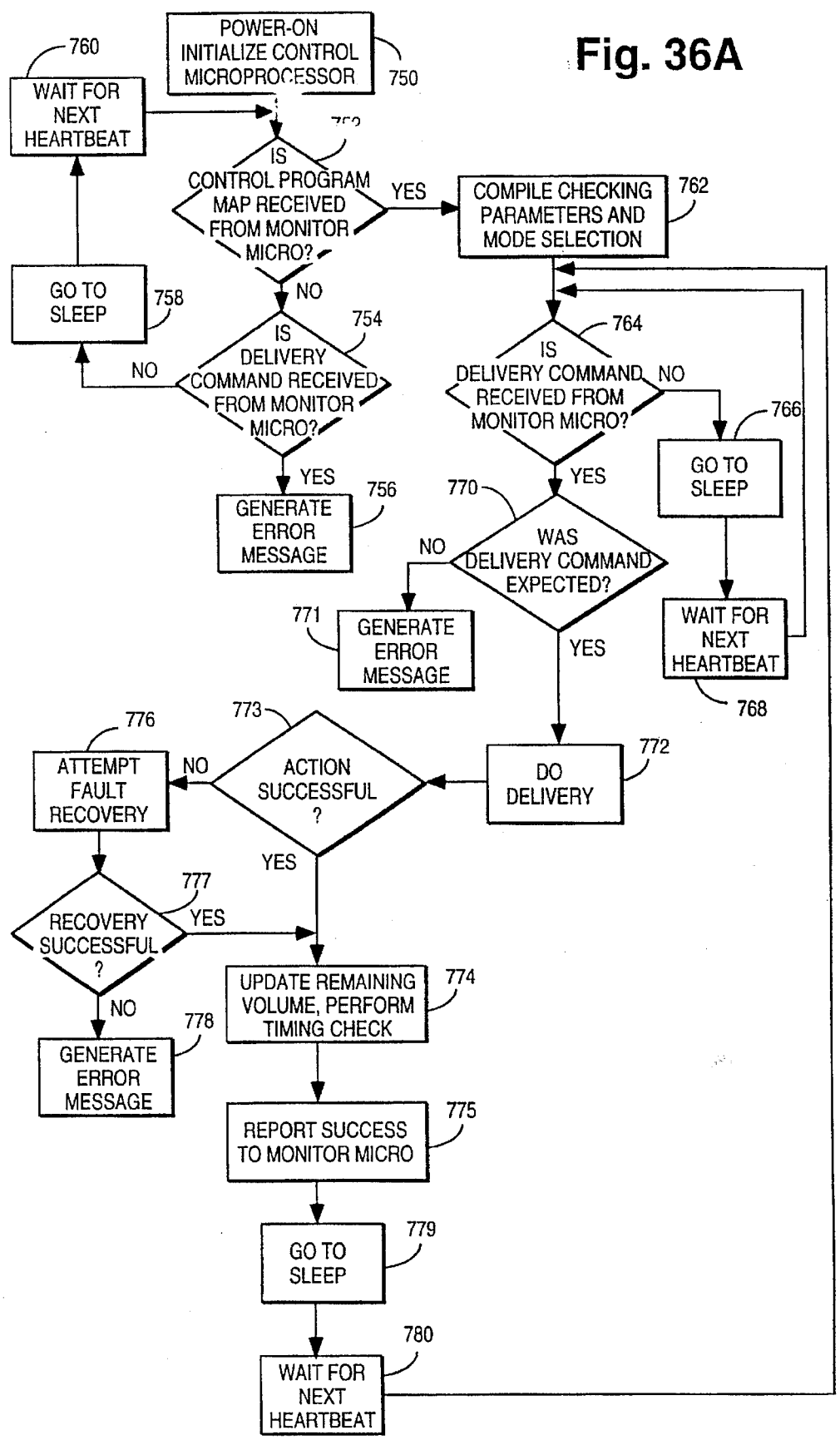
FIG. 36A is a flow diagram of the main routine of the control microprocessor software.

FIG. 36A is generalized flow diagram representing the major operational routine of the control microprocessor 542. The primary function of the control microprocessor 542 is to execute the plunger and valve motion control algorithms which are intended to provide variety of delivery profiles within acceptable predefined accuracy standards while minimizing energy consumption and further while continuously monitoring the pump mechanics to provide prompt notification of any failure conditions. FIGS. 36B–K are flow diagrams of subroutines called by the main control routine.

1. Main Control Routine

The main control routine begins at block 750 of FIG. 36A, wherein the main control microprocessor program is initialized. At decision block 752 it is determined whether the program map complied by the monitor microprocessor 540 at block 642 of FIG. 35A has been received from the monitor microprocessor 540 through execution of the support communication with control microprocessor block 628 of FIG. 35A. If a program map has not been received from the monitor microprocessor 540, at decision block 754 it is determined whether a delivery command has been received from the monitor microprocessor. If a delivery command has been received, at block 756 an error message is generated unless the pump is being primed because a system error has occurred if a delivery command is received by the control microprocessor 542 without having first received a program map. The error message generated at block 756, like all error messages discussed in FIGS. 36A–K, is sent to monitor microprocessor 540, which activates an appropriate alarm. The control microprocessor 542 verifies the activation of an appropriate alarm by the monitor microprocessor 540. If the control microprocessor 542 is unable to verify that the appropriate alarm has been activated, the control microprocessor 542 will directly activate an alarm. If at block 754 a delivery command is not received from the monitor microprocessor 540, the control microprocessor 542 is put to sleep at block 758 and at block 760 the control microprocessor is awakened by the next heartbeat and decision block 752 is again entered.

If at decision block 752 a program map has been received from the monitor microprocessor 540, the program map is compiled at block 762 to set forth checking or verification parameters and further to determine which of the four pump operation modes is required to execute fully the program map. A determination is made at decision block 764 whether a delivery command has been received from the monitor microprocessor 540. If no delivery command has been received, the control microprocessor 542 is put to sleep at block 766 until it is awakened at the next heartbeat at block 768 and the control microprocessor then again executes decision block 764.

If a delivery command has been received from the monitor microprocessor, at decision block 770 it is determined whether the delivery command was expected. If a delivery command was received and was not expected, an error message is generated and conveyed to the monitor microprocessor 540. If the delivery command was expected at decision block 770, a delivery is executed at block 772. Delivery commands from the monitor microprocessor only specify whether the infusion is to be 5, 25 or 125 microliters. The delivery at block 772 is conducted in accordance with the mode selection configured at block 762 to satisfy the delivery profile. Delivery is executed through one of the four delivery routines which are discussed in greater detail with reference to FIGS. 37B–E. Inquiry is made at decision block 773 whether the delivery task has been successfully completed. If the action has been successfully completed, at block 774 the volume remaining in the reservoir is updated and the acceptability of the flow rate is confirmed. That is, when a select volume of liquid has been delivered, the routine determines if the time to deliver the select volume provides an acceptable flow rate. If the flow rate is acceptable, the routine is reset. At block 775 successful completion of the delivery sequence is reported to the monitor microprocessor 540. Although not illustrated in FIG. 36A, if the timing check performed at block 774 does not confirm proper operation of the pump, an error message is sent to the monitor microprocessor.

Returning to decision block 773, if a pumping action has not been successfully completed, at block 776 fault recovery is attempted. The fault recovery routine is shown in detail in FIG. 36H and will be discussed below. At decision block 777 the routine determines whether the recovery was successful. If the recovery was successful, the routine continues at block 774. If the recovery was not successful, an error message is generated at block 778 and conveyed to the monitor microprocessor 540. Continuing with block 775, following report of a successful delivery action to the monitor microprocessor 540, the control microprocessor 542 is put to sleep at block 779 until the next heartbeat at 780, wherein the control microprocessor 542 is awakened and the main routine returns to decision block 764.

As discussed above with reference to blocks 762 and 772, the main control routine includes four subroutines, FIGS. 36B–E, for executing pump modes 2–5. The subroutines actuate the plunger and valve motors so as to discharge the desired volume of medication at the desired rate for the desired time period. An overview of modes 2–5 is contained in FIG. 38. Many of the details set forth in FIG. 38 will be apparent following discussion of FIGS. 36B–E below. For the present purpose, it is only necessary to know that mode 2 delivers liquid at a rate of 0.1–7.9 ml/hr.; mode 3 delivers medication at a rate of 8–49.9 ml/hr.; mode 4 delivers medication at a rate of 50–149 ml/hr.; and mode 5 delivers medication at a rate of 150–390 ml/hr. Determination is made which one of modes 2–5 is executed at the "do delivery" block 772 in accordance with the selected delivery profile delivered to the control microprocessor as the control program map. See FIG. 36A, block 752,762.

2. Mode "2" Delivery Routine

Figure 36B:
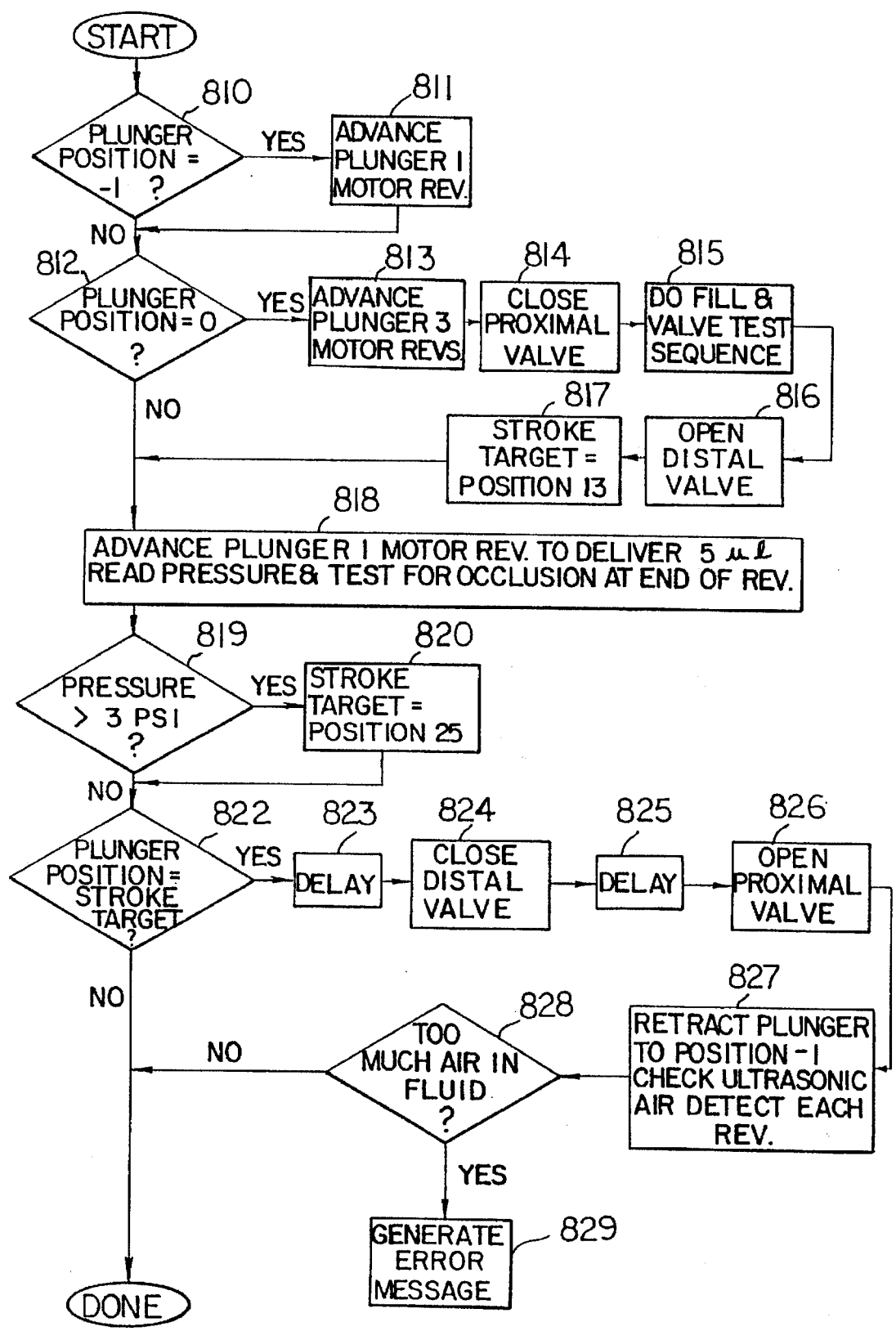
FIG. 36B is a flow diagram of the mode "2" delivery routine.
Figure 44:
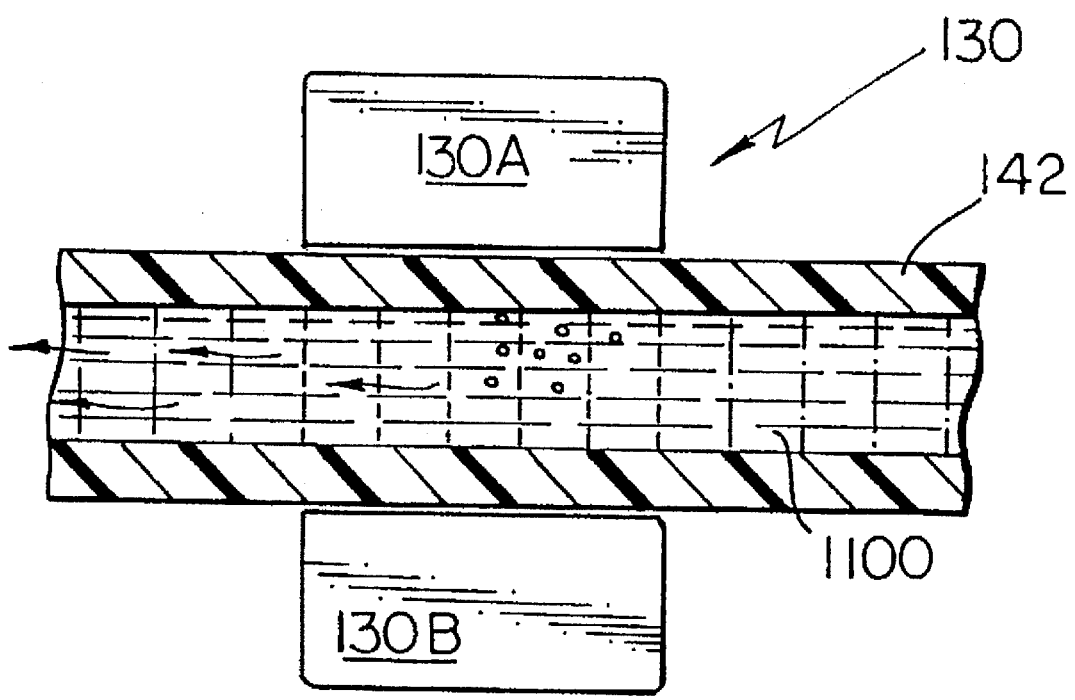
FIG. 44 is a schematic representation of the incremental air detection of the present invention.

The routine for executing delivery mode 2 is illustrated in the flow diagram of FIG. 36B. At decision block 810 the routine determines whether the plunger is in position "–1". If the plunger is in position "–1", the plunger is advanced one motor revolution to position "0" at block 811. Thus, blocks 810–811 constitute a refill compensation sequence which ensures that when the plunger 120 is at position "0", the pump chamber 140 is at the expected volume. If the plunger is not in position "–1", or following block 811, at decision block 812 it is determined whether the plunger is in position "0". If the plunger is in position "0", at block 813 the plunger motor is advanced three revolutions, thereby advancing the plunger to position "3". Advancing the plunger three motor revolutions at block 813 minimizes the effect of "memory" acquired by pump chamber 140 as a result of compression of the pump chamber, and thereby improves pump accuracy. Next, at block 815 the fill valve and leak test sequence is executed. A flow diagram of block 815 is shown in FIG. 36F, and is discussed below. Following execution of the fill valve and leak test sequence at block 815, at block 816 the outlet or distal valve 124 is opened. At block 817 the stroke target is set to "13" and the routine continues at block 818 in the same manner as if the plunger position had not been equal to "0" at decision block 812. "13" is the preferred target position so that the pump chamber is compressed only a total of thirteen revolutions to prevent the pump chamber from acquiring a "memory" of less than the full refill volume as a result of occupying a compressed position for extended periods of time. At block 818 the plunger motor is advanced one revolution to deliver five microliters of medication. Concurrently, pressure within the pump chamber 140 is measured by the pressure transducer 362 for the purpose of detecting a downstream occlusion. The pressure within the pump chamber 140 is compared with a predetermined reference pressure. If the predetermined reference pressure is exceeded, an error message is generated by the control microprocessor 542 and conveyed to the monitor microprocessor 540. If the predetermined reference pressure is not exceeded, the routine continues at decision block 819. At decision block 819 it is determined whether the pump chamber pressure is greater than or equal to three psi above the inlet line pressure which is determined during the valve test sequence at block 815 and is designated in FIG. 36F as (A. If it is, the stroke target position is set to "25" at box 820 in order to ensure that the pump chamber 140 will be subject to sufficient compression during the pumping sequence to generate a pump chamber pressure greater than the reference pressure so as to ensure any downstream occlusion is detected. If the pump chamber pressure is found to be less than three psi above the inlet line pressure at decision block 819, or following setting of the target stroke position to "25" at block 820, it is determined whether the plunger is at the stroke target position at block 822. If it is, at block 823 a delay occurs with the plunger extended. This delay is introduced to dissipate excess pressure in the pump chamber 140 due to a restriction in a downstream connection such as a PIC line. Such excess pressure can cause ballooning of the pump chamber 140, proximal valve 142 or distal valve 144, degrading pump accuracy. As used herein, dissipate does not necessarily mean the excess pressure disappears. Rather, it is intended to mean the pressure decreases sufficiently that ballooning of the pump chamber is substantially eliminated, to the point that pump output is virtually unaffected by the ballooning. The delay is calculated as follows: delay=½ $(T_1-T_2)$, wherein $T_1$ is the time between the beginning of a pumping operation and the beginning of a subsequent pumping operation required to meet a specified pump output flow rate and $T_2$ is the time required for the electromechanical pumping apparatus to physically complete the pumping operation. At block 824 the outlet or distal valve 124 is closed. At block 825 a small delay occurs to provide time for the distal valve 124 to fully close before, at block 826 the inlet or proximal valve 122 is opened. At block 827 the plunger motor is reversed and the plunger is retracted to position "−1" while the ultrasonic air detect 130 is actuated after each plunger motor revolution. The ultrasonic air detect 130 structure is discussed in Section F above. The air detetect operation is illustrated in FIG. 44. As seen in FIG. 44, the air detection segment of the tube lies between the transmitter 130A and the receiver 130B. Approximately 5 microliter segments 1100 are illustrated between the phantom lines of FIG. 44.

The air detection segment of the tube contains approximately 5 of the segments 1100, or approximately 25 microliters. The ultrasonic air detect 130 takes a snapshot of a tube segment between the transmitter and receiver of the ultrasonic air detect 130 containing on the order of 25 microliters of liquid each revolution of the plunger motor. An "air" signal is generated by the receiver if the air detect detects greater than approximately 50% air in the tube segment. As the plunger motor completes the next revolution, a new five microliters is introduced into the tube segment as five microliters leave the tube segment and another pulse is transmitted by the transmitter. At decision block 828 the routine determines if the sum of the "air" signals exceeds a select number for any two consecutive refill cycles. The select number is preferably 15. If the select number is exceeded, pump operation is halted and an error message is generated at block 829. If the amount of air in the fluid is not excessive, the routine returns to block 773 of the main control routine illustrated in FIG. 36A. Likewise, if at decision block 822 the plunger position is not equal to the stroke target, the routine returns to block 773 of FIG. 36A.

3. Mode "3" Delivery Routine

Figure 36C:
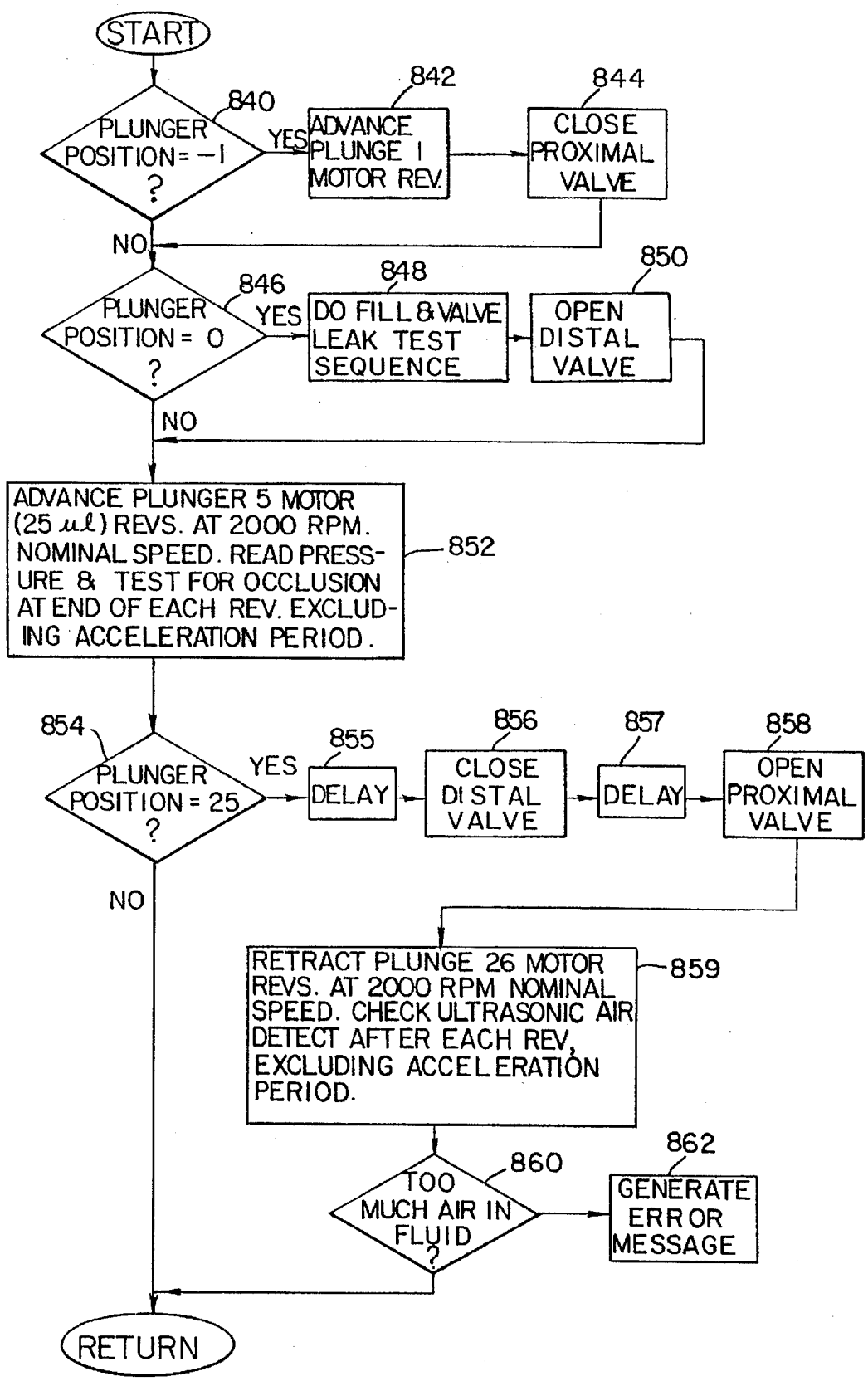
FIG. 36C is a flow diagram of the mode "3" delivery routine.
Figure 36:
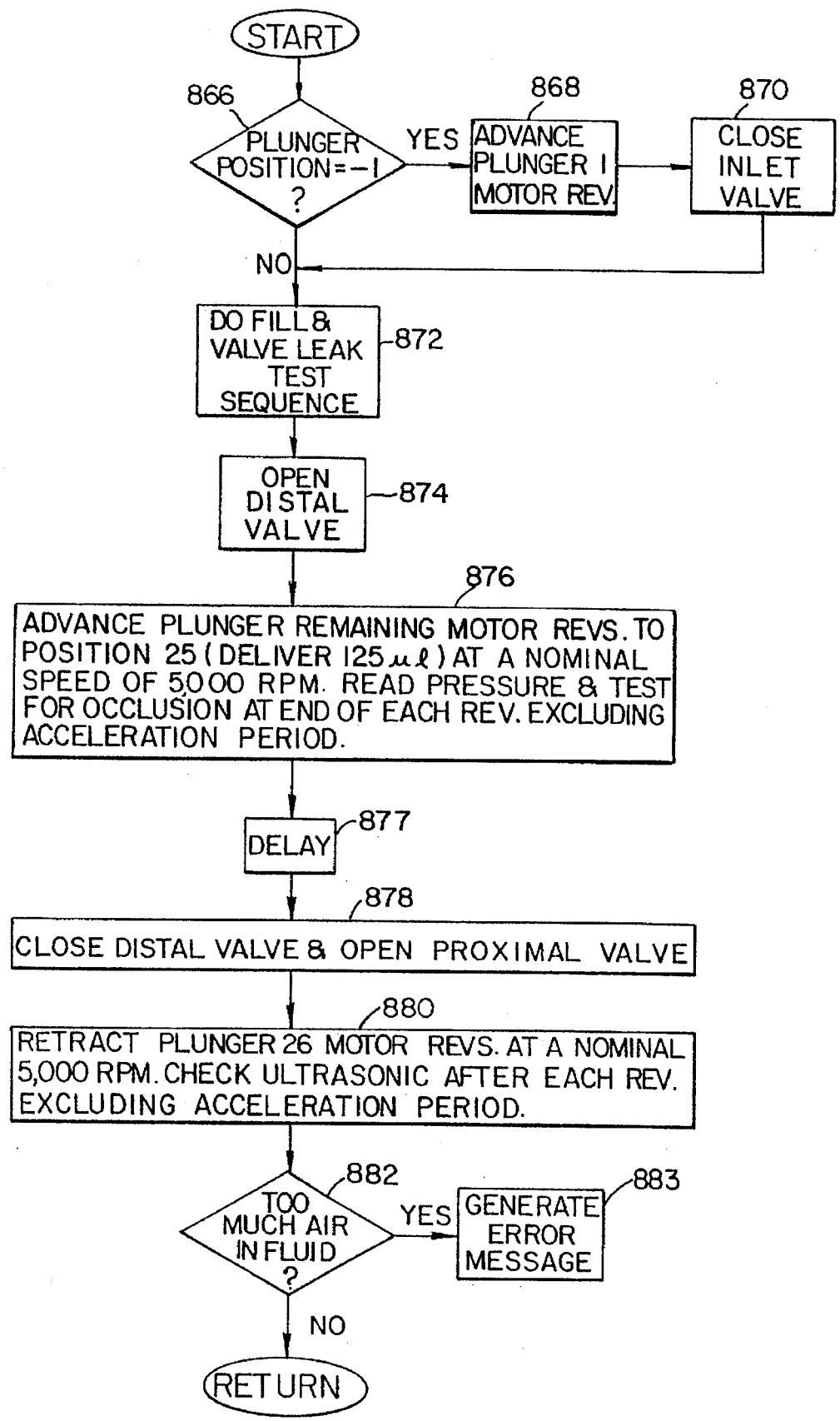
FIG. 36D is a flow diagram of the mode "4" delivery routine.
FIG. 36E is a flow diagram of the mode "5" delivery routine.
FIG. 36F is a flow diagram of the "fill and valve leak test" sequence of FIG. 36A.
FIG. 36G is a flow diagram of the "sleep" routine.
FIG. 36H–36K are a series of flow diagrams of the "fault recovery attempt" routine.

FIG. 36C illustrates the subroutine for executing delivery mode three. Determination is made at decision block 840 whether the plunger position is equal to "−1". If the plunger position is equal to "−1", the plunger is advanced one motor revolution at block 842. If the plunger position is not equal to "−1" at block 840, or following advancing of the plunger at block 842, at decision block 846 it is determined whether the plunger position is equal to "0". If the answer is yes, the fill and valve leak test sequence described in detail with respect to FIG. 36F is performed at block 848. Thereafter, at block 850 the distal or outlet valve is opened. If the plunger position is not equal to "0", or following opening of the distal valve at block 850, at block 852 the plunger motor is advanced five motor revolutions at 2000 rpm nominal speed so as to discharge 25 microliters of medication. At the end of each motor revolution, except during the acceleration period, the pump chamber pressure is monitored to check for downstream occlusions. At decision block 854 it is determined whether the plunger 120 is at position number "25". If it is not, the routine returns to block 774 of FIG. 36A. If the plunger position is equal to "25", at block 855 a delay occurs for dissipation of excess pressure in the pump chamber, as discussed above with reference to block 823 of FIG. 36B. At block 856 the distal or outlet valve 124 is closed, followed by a short delay at block 857 to allow for full closure of the outlet valve before the proximal or inlet valve 122 is opened at block 858. At block 859 the plunger 120 is retracted 26 motor revolutions at a 5000 rpm nominal speed. At the conclusion of each revolution of the plunger motor 256, excluding the acceleration period, ultrasonic air detection takes place. At decision block 860 it is determined whether too much air has entered the pump chamber. If so, an error message is generated at block 862. If the amount of air is acceptable, the routine returns to block 773 of FIG. 36A.

4. Mode "4" Delivery Routine

FIG. 36D illustrates the routine for executing delivery mode four. Determination is made at decision block 866 whether the plunger is at position "−1". If it is, the plunger is advanced one motor revolution at block 868. If the plunger position was not equal to "−1" at decision block 866, or following execution of block 868, at block 872 the fill and valve leak test sequence described below with reference to FIG. 36F is conducted. At block 874 the distal valve is opened. At block 876 the plunger is advanced to position "25" at a nominal speed of 5000 rpm, delivering 125 microliters of medication. Pump chamber pressure is read at the end of each revolution, excluding the acceleration period, to test for downstream occlusions. If a downstream occlusion is detected, an alarm signal is generated. At block 877 a delay allows for dissipation of excess pressure in the pump chamber 140 caused by a downstream flow restriction such as a PIC line, as discussed above with reference to block 823 of FIG. 36B. At block 878 the outlet valve is closed and the inlet valve 122 is opened. At block 880 the plunger 120 is retracted 26 motor revolutions at a nominal speed of 5000 rpm. At the end of each revolution of the plunger motor 256, excluding the acceleration period, the ultrasonic air detect 130 detects any air in the fluid entering the pump chamber 140. At decision block 882 it is determined whether too much air has entered the pump chamber. If excess air has entered the pump chamber, an error message is generated at block 883. If the amount of air is acceptable, the routine returns to block 773 of FIG. 36A.

5. Mode "5" Delivery Routine

Figure 36E:
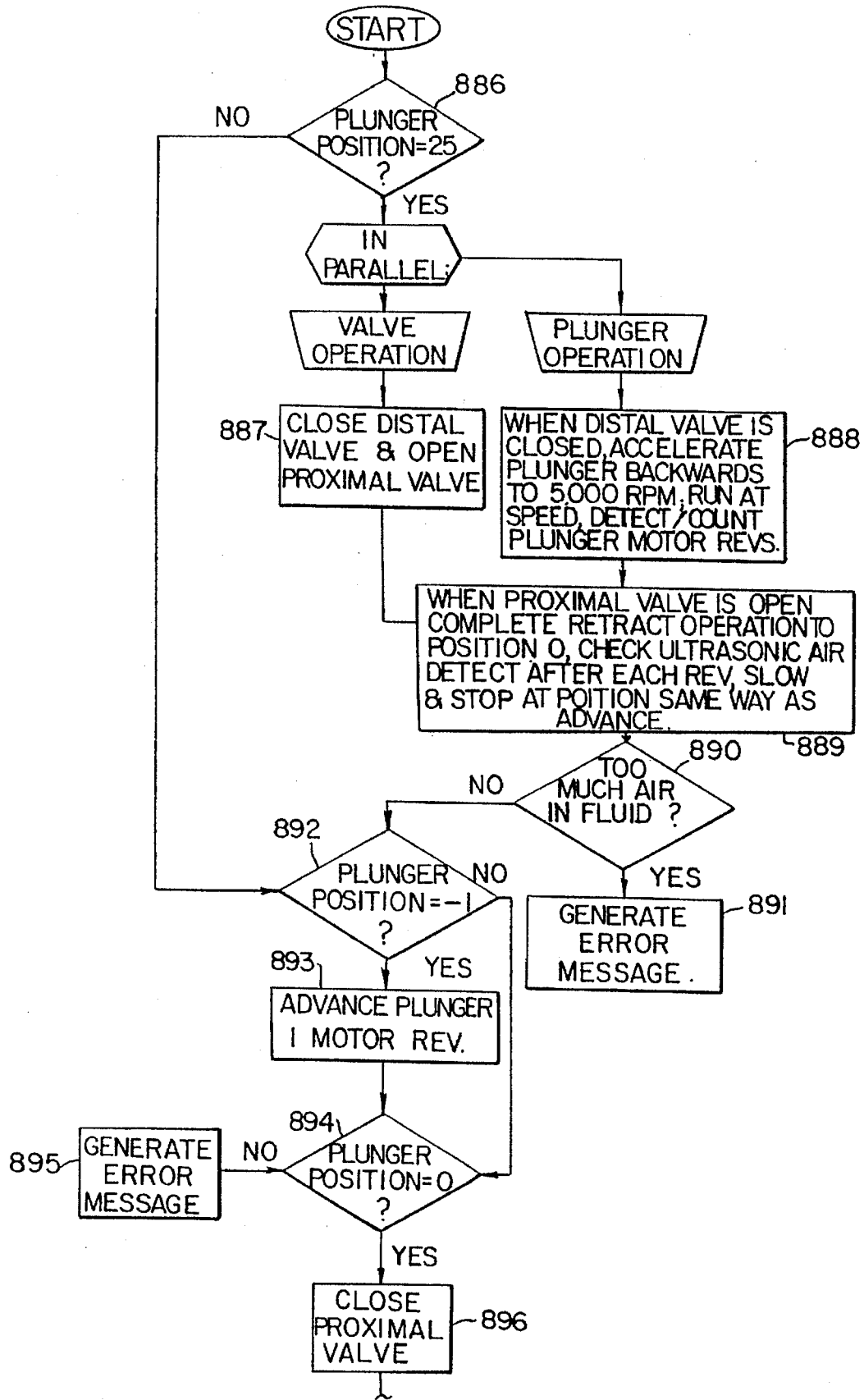
Figure 36E:
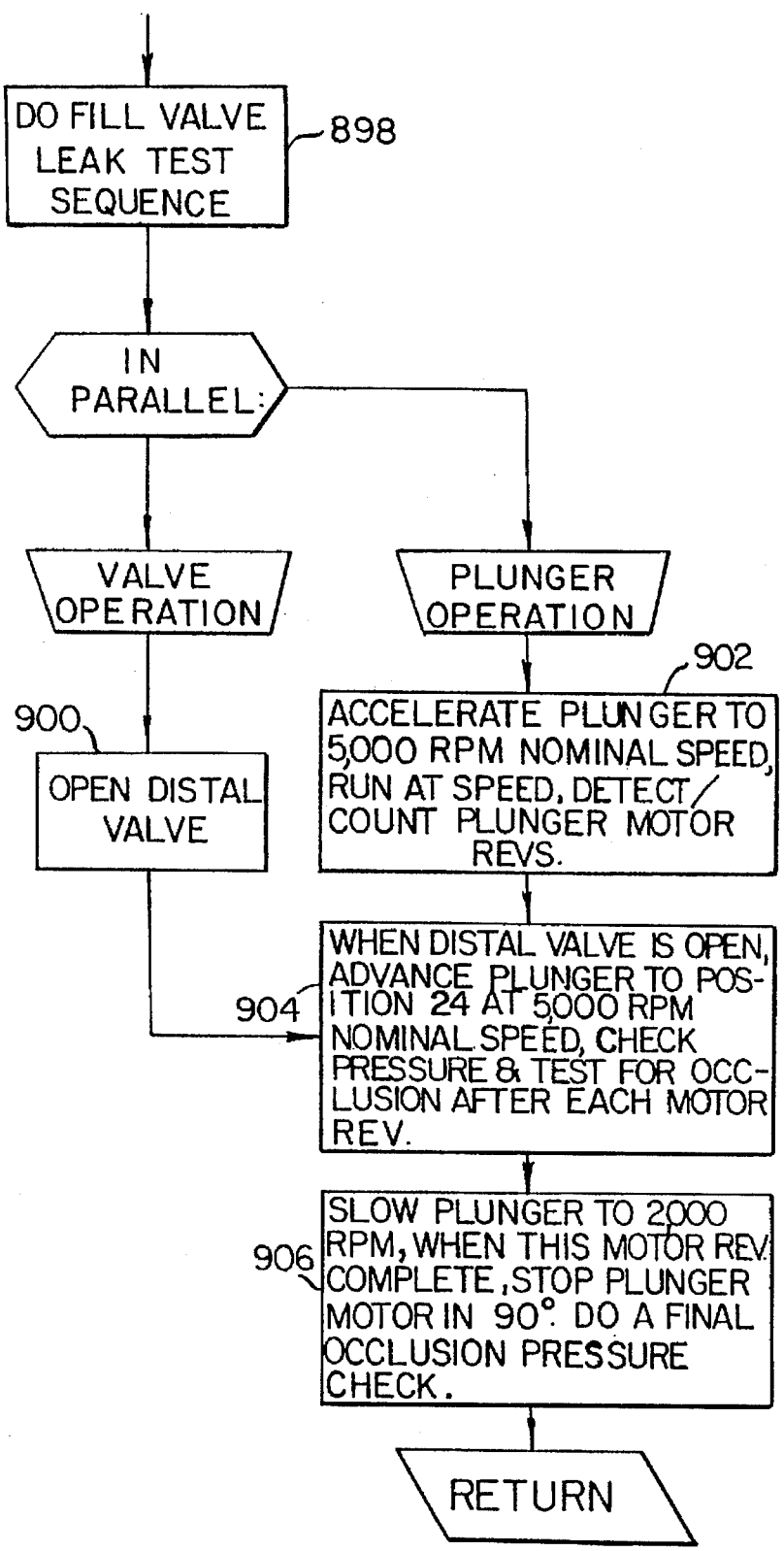
Figure 36F:
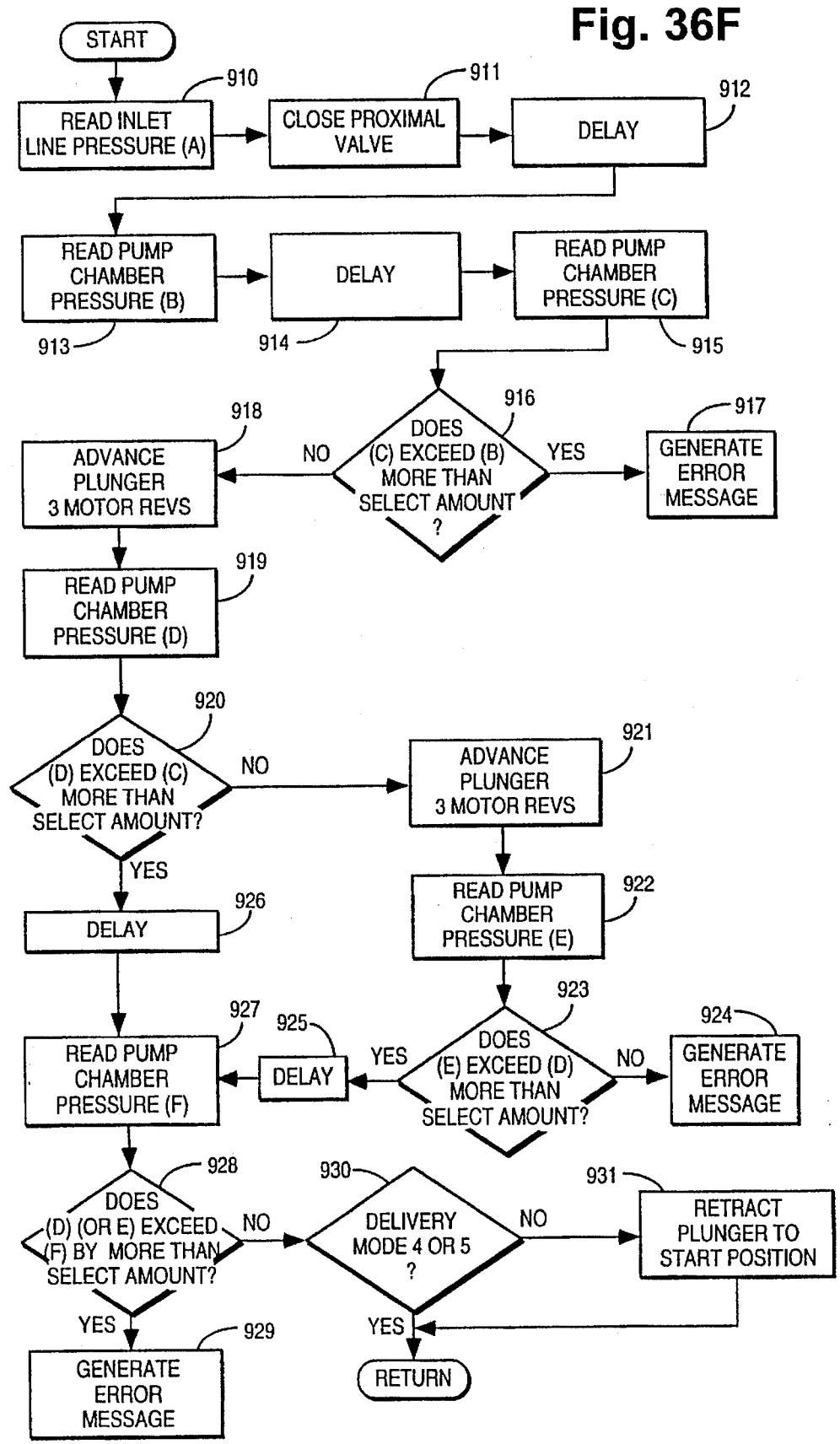

FIG. 36E is a flow diagram illustrating execution of delivery mode 5. At decision block 886 it is determined whether the plunger 120 is in position "25". If the plunger is in position "25", blocks 887 and 888 are performed in parallel. More particularly, at block 887 valve operation is controlled. The distal or outlet valve 124 is closed and the proximal or inlet valve 122 is open. At block 888, following closure of the distal valve at block 887, the plunger is accelerated backwards to 5000 rpm, with the revolutions being counted by monitoring of the Hall sensor 400. At block 889 the plunger motor 256 operates at 5000 rpm until the plunger 120 approaches position "0", at which time the plunger motor is slowed to 2000 rpm and is brought to rest at position "0". More particularly, at block 889 the plunger motor is slowed to 2000 rpm for its 25th revolution. When this revolution is complete, the plunger motor is stopped by the magnetic detent and reversal of motor current following 90 degrees of additional rotation. Ultrasonic air detection occurs after each revolution, excluding acceleration and deceleration. The results of the ultrasonic air detect are evaluated at block 890. If excessive air is detected, an error message is generated at block 891 and pump operation is halted. If the amount of air is acceptable, the routine returns to block 892. If at decision block 886 it was determined that the plunger position was not equal to "25", the routine continues at decision block 892 as well. At decision block 892 it is determined whether the plunger is at position "−1". If the plunger is found to be at position "−1", at block 893 the plunger is advanced one motor revolution of the plunger motor 256 to position "0". If at 892 the plunger is not at position "−1", or following advancement of the plunger one revolution at 893, at decision block 894 it is determined whether the plunger is at position "0". If the plunger is determined not to be at position "0", an error message is generated at block 895 and pump operation halts. If at decision block 894 the plunger is at position "0" the fill valve leak test sequence described in detail with reference to FIG. 36F is performed at block 898. Valve operation at block 900 and plunger operation at block 902 are then performed in parallel. At block 900 the distal valve is opened. At block 902 the plunger motor 256 is accelerated to 5000 rpm nominal speed. The plunger motor revolutions are monitored by means of the Hall sensor 400 on the plunger motor 256. Upon opening of the distal valve at block 900, the plunger motor 256 is advanced to plunger position "24" at 5000 rpm nominal speed. Pressure is checked after each motor revolution for downstream occlusion. Upon reaching position "24", the plunger motor 256 is slowed to 2000 rpm at block 906 for the 25th revolution. When this revolution is complete, the plunger motor is stopped by the magnetic detent following 90° of additional rotation and a final occlusion pressure check is conducted. At the conclusion of the operations at block 906, the routine returns to block 773 of the main control microprocessor routine of FIG. 36A. The plunger remains in position "25" until the start of the next cycle. The time delay between the final extension of the plunger at block 906 to the beginning of the next cycle is important because it allows excess pressure in the pump chamber which may have resulted from back pressure during infusion of the medication to dissipate. As this excess pressure dissipates, additional fluid is discharged from the pump chamber, thereby increasing the accuracy of the pump. By way of example, at the maximum pumping rate of 390 ml/second, approximately 0.2 seconds of delay is provided for dissipation of excess pressure. At lower rates the delay may be up to several seconds.

6. Fill and Valve Leak Test Sequence Routine

The "fill and valve leak test sequence" routine described in each delivery mode subroutine of FIGS. 36B–E is illustrated in the flow diagram of FIG. 36F. At block 910 the inlet line pressure designated herein as "A" is read using the pressure transducer 362. The inlet or proximal valve 122 is then closed at block 911. Following a short delay at block 912, the pump chamber pressure is read again at block 913 and is designated herein as "B". At block 914 a delay occurs which is a function of the rate of delivery at the particular mode. That is, the higher the rate of delivery, the shorter the delay at block 914. At block 915 the pump chamber pressure is read again and is designated herein as "C". At block 916 it is determined whether pressure "C" exceeds pressure "B" by more than a select amount. That is, at decision block 916 it is determined whether the outlet pincher valve 122 is leaking, which may be the case where the outlet line pressure exceeds the pump chamber pressures "B". If pressure "C" exceeds pressure "B" by more than the select amount, an error message is generated at block 917. If it does not, at block 918 the plunger 120 is advanced three revolutions of the plunger motor 256. At block 919 the pump chamber pressure is again read and the read pressure is designated herein as "D". At decision block 920 it is determined whether pressure "D" exceeds pressure "C" more than a select amount. If pressure "D" does not exceed pressure "C" more than a select amount, this is an indication that the pump chamber may be not filled with liquid. The test is then repeated at block 921, where the plunger 120 is advanced three more revolutions of the pump motor. At 922 the pump chamber pressure is again read, and designated "E" herein. At decision block 923 it is determined whether pressure "E" exceeds pressure "D" more than a select amount. If it does not, this confirms that the pump chamber is not filled with fluid, and an error message is generated at block 924. If "E" does exceed "D" by more than a select amount, at block 925 a delay is instituted. Likewise, if at decision block 920 it is determined that pressure "D" does exceed pressure "C" by more than a select amount, at block 926 a delay is instituted. Following the delays at blocks 925, 926, at 927 the pump chamber is again read and designated herein as "F". At decision block 928 it is determined whether pressure "D" or, if at decision block 920 "D" does not exceed "C" by more than a select amount, pressure "E" exceeds "F" by more than a select amount. If it does, this indicates that one of the inlet or outlet pincher valves 122,124 is leaking, and an error message is generated at block 929. If it does not, at block 930 it is determined whether the routine is in delivery mode "4" or "5". If it is not, at block 931 the plunger motor is retracted to the start position, that is, position "3" of mode 2 or position "0" of mode 3. Following retraction of the plunger at block 931, the routine returns to block 816 or 850 of delivery modes 2–3 illustrated in FIGS. 36B–36C, respectively. If at decision block 930 the routine is in delivery mode 4 or 5, the routine returns to block 874 or block 900 of FIGS. 36D and 37E, respectively.

7. Sleep Routine

Figure 36G:
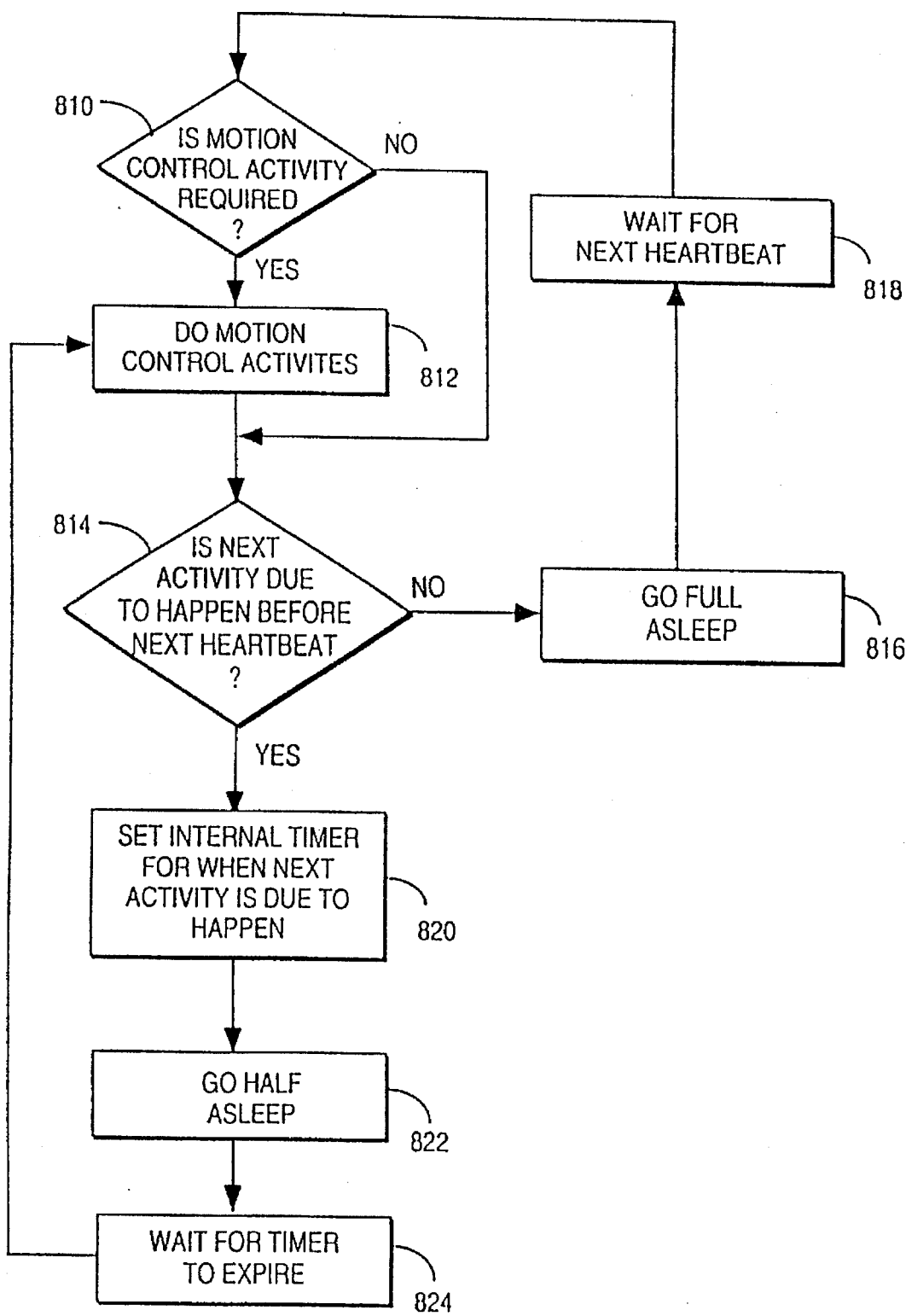

Between each of the blocks of the routines illustrated in FIGS. 36B–E is interposed an electronic sleep feature which, in conjunction with a heartbeat generator 590, see FIG. 31, minimizes power consumption by causing the control microprocessor 542 to power down when no control activity is required. The operation of the electronic sleep feature is illustrated in FIG. 36G. At decision block 810 it is determined whether a motion control activity is required. A motion control activity is required when a change in an output related to motion control must be made. If a motion control activity is required, the motion control activity is initiated at block 812. If no motion control activity is required, or after a motion control activity is completed at block 812, at block 814 determination is made whether the next activity is due to be initiated the next heartbeat. If the activity is not due to happen before the next heartbeat, then the control microprocessor 542 is put to sleep. At block 818 the next heartbeat is detected and the routine returns to decision block 810. If it is determined at decision block 814 that the next activity is due to happen before the next heartbeat, an internal timer for when the next activity is due to happen is set at block 820. The control microprocessor 542 then goes into an idle state or a "half asleep state" at block 822 and at block 824 waits for the timer period to expire. Upon expiration of the timer period, the routine returns to block 812 where the motion control activity is completed.

8. Fault Recovery Routine

The software fault recovery attempts routine, which is called at the block 776 of the main control microprocessor routine illustrated in FIG. 36A, is illustrated in the flow diagram of FIGS. 36H–36K.

Unexpected operating conditions will cause error flags to be set. Within the dual microprocessor software system, detection of fault conditions causes recovery attempts to be made within the constraints of the system. This improves fault tolerance of the pump 10 which in turn improves performance characteristics as it attempts to overcome transient fault conditions such as a patient rolling over on the tubing or a patient pressing against an IV bag.

Figure 36H:
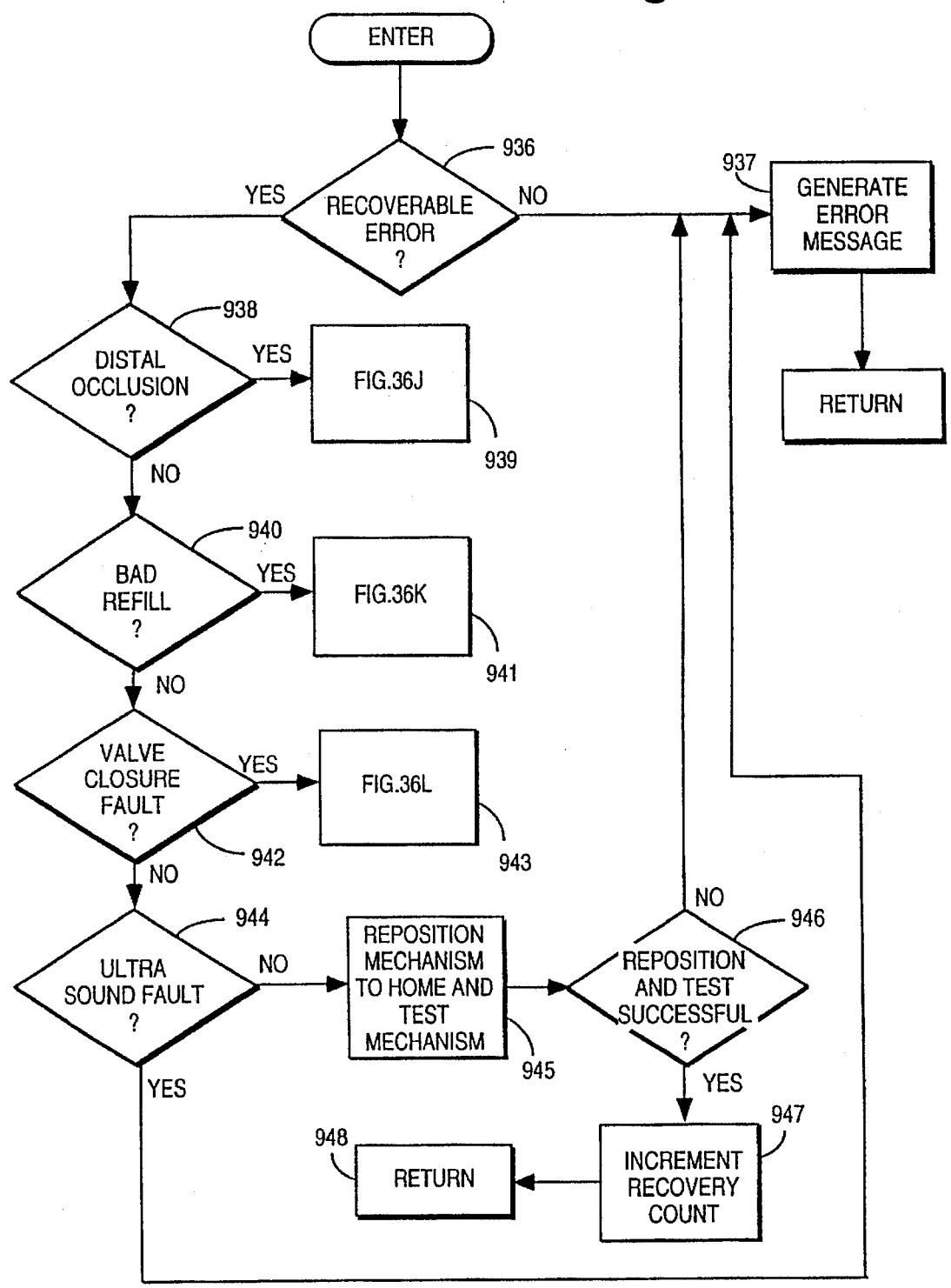

Referring initially to FIG. 36H, a flow diagram illustrates the fault recovery routine. The routine begins at a decision block 936 which determines whether the error detected at the decision block 773 of the main control microprocessor routine of FIG. 36A is a recoverable error.

Non-recoverable errors include an absence of a plunger home signal, absence of a valve neutral signal, a feedback circuitry error, and an illegal pump command (e.g., a command disrupted during transmission from the monitor microprocessor to the control microprocessor). If such a non-recoverable error is identified at decision block 936, at block 937 an error message is generated and conveyed to the monitor microprocessor 540. At block 944 the routine returns to block 777 of the main control microprocessor subroutine of FIG. 36A.

Figure 36I:
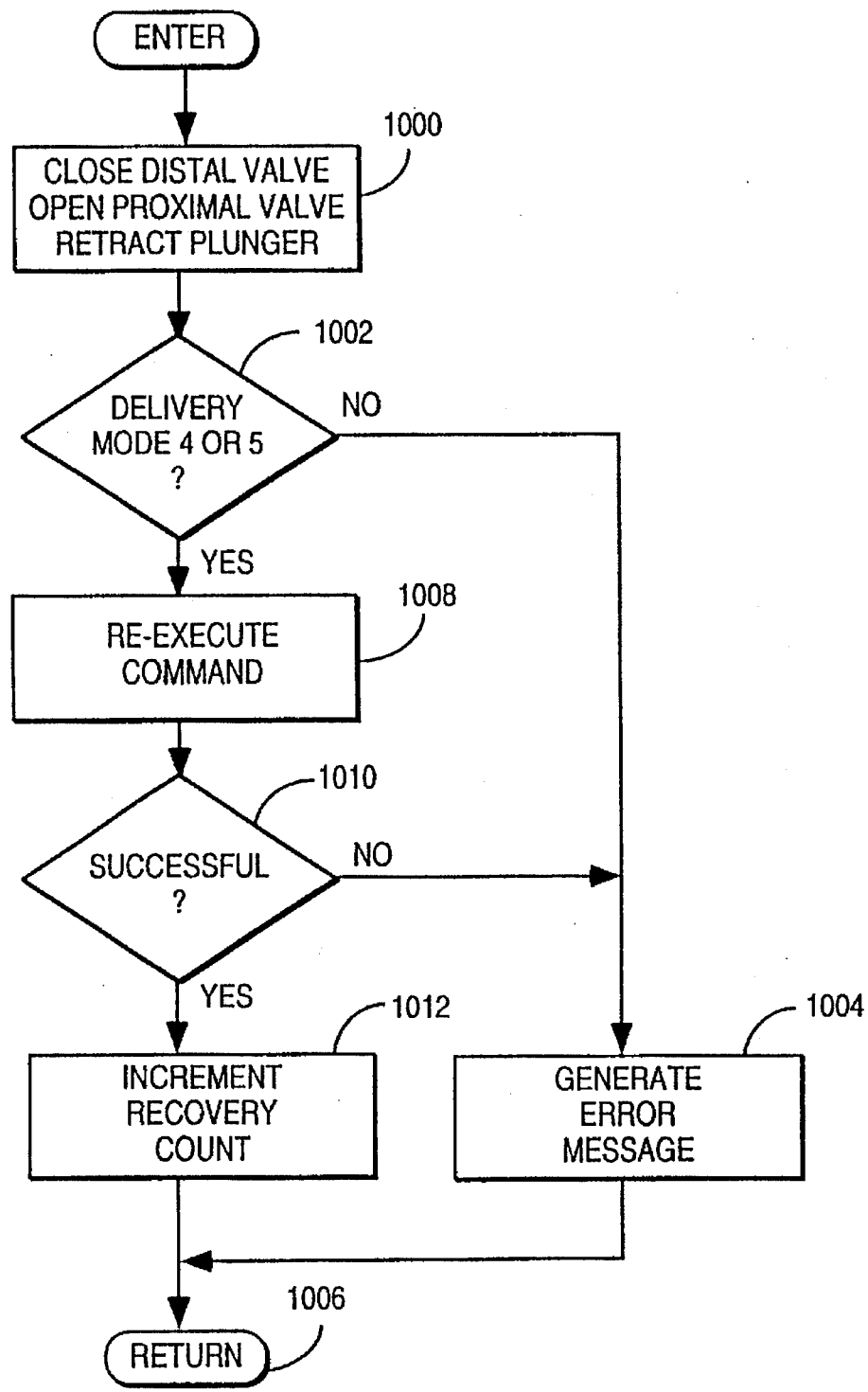
Figure 36J:
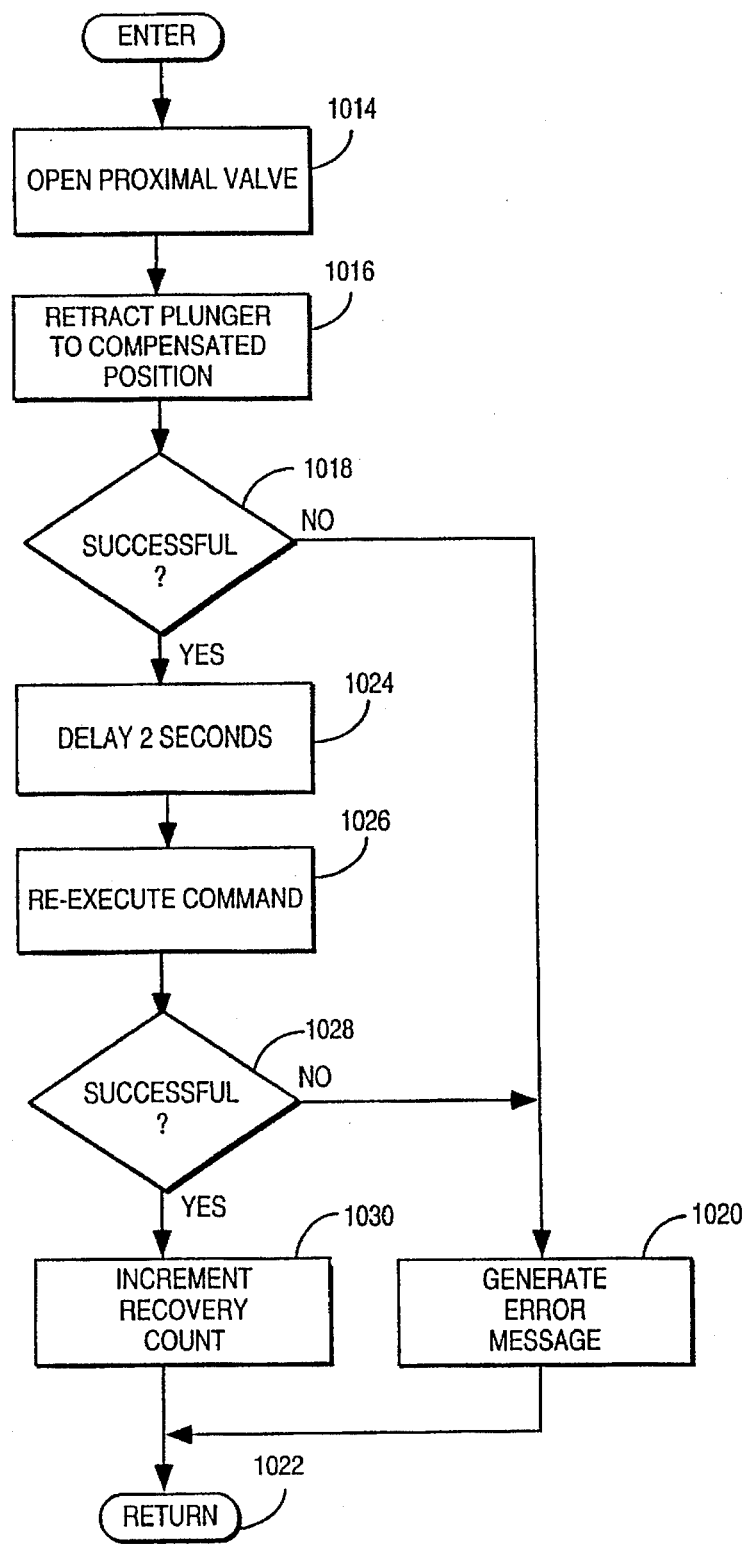

If the error is identified as recoverable error, the routine continues at decision block 938 where it is determined whether the error message is that a distal occlusion condition is present. If a distal occlusion occurs as determined by an excessive pressure rise, then a recovery routine illustrated in FIG. 36I is implemented. This routine begins at a block 1000 by closing the distal or outlet valve 124, opening the proximal or inlet valve 122 and retracting the plunger 120. A decision block 1002 then determines if either delivery mode 4 or 5 was being executed. If not, then an error message is generated at a block 1004 and the routine ends at a block 1006. If either delivery mode 4 or 5 was being executed, then the original command being acted upon at the time the error occurred is reexecuted at a block 1008. A decision block 1010 determines if the command was reexecuted successfully. If not, then control proceeds to the block 1004. If the command was successful, then a recovery count is incremented at a block 1012 and the routine ends.

The recovery count is used to determine if excessive recovery operations have occurred. If too many recovery operations have occurred within a select period of time, then the delivery action could be impacted negatively, warranting shutting down the pump 10 and generating an alarm.

In the flow diagrams, when the recovery count is incremented it is assumed that recovery is successful. This determination is used at the decision block 777 of FIG. 36A. If, instead, an error message is generated, then it is assumed that recovery was unsuccessful and further operation of the pump driving mechanism is halted.

Returning to FIG. 36H, if the error message is not for a distal occlusion, as determined at the decision block 938, then a decision block 940 determines if the error message is for a bad refill of the pump chamber. This occurs when there is an insufficient indicated pressure rise after advancing the plunger 120 with both valves 122 and 124 closed. If a bad refill error has occurred, then control advances to a block 941 to implement a recovery routine illustrated in FIG. 36J.

The bad refill recovery routine begins at a block 1014 which opens the proximal valve 122. The plunger 120 is retracted at block 1016 to a compensated position. A decision block 1018 determines if the commands generated at the blocks 1014 and 1016 were executed successfully. If not, then an error message is generated at a block 1020 and the routine ends at a block 1022. If the commands were successful, then an approximately two second delay is implemented at block 1024 and the original delivery command is reexecuted at a block 1026. A decision block 1028 determines if the original command was reexecuted successfully. If not, then control proceeds to the block 1020. If so, then the recovery count is incremented at a block 1030 and the routine ends.

Figure 36K:
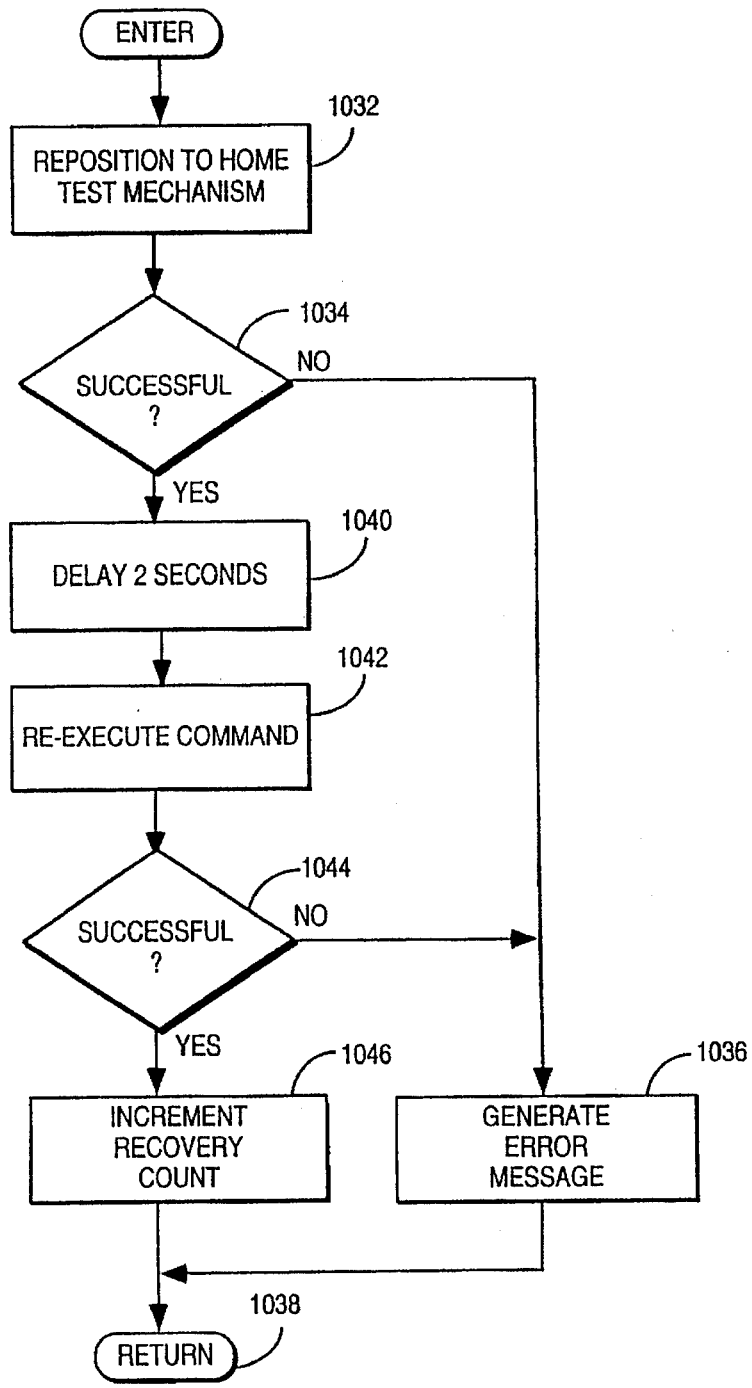

Returning to the flow diagram of FIG. 36H, if the error message was not for a bad refill, as determined at the decision block 940, then a decision block 942 determines if the error was for a valve closure fault. This error condition is reported in blocks 917 or 929 of FIG. 36F. If so, then a recovery routine illustrated in FIG. 36K is implemented at a block 943.

The valve closure fault recovery routine begins at a block 1032 which repositions the mechanism to a "home" position. More particularly, the plunger 120 is returned to its "home" or "zero" position, the distal valve 124 is opened and the proximal valve 122 is closed. Before the mechanism returns to the "home" position, however, each of the inlet valve 122, outlet valve 124 and plunger 120 are tested by actuation to assure they are functioning properly. If they are not, or if the mechanism cannot return to the "home" position, as determined at a decision block 1034, then an error message is generated at a block 1036 and the routine ends at a block 1038. If the repositioning is successful, then a two second delay is implemented at a block 1040. The original command is then reexecuted at a block 142. A decision block 1044 then determines if the original command was reexecuted successfully. If not, then control proceeds to the block 136. If so, then the recovery count is incremented at block 1046 and the routine ends.

Returning to the flow diagram of FIG. 36H, if the error message is not for a valve closure fault, then a decision block 944 determines if the error was for an ultrasound fault. This error occurs if excessive air has been detected by the ultrasonic air detector 130. If so, then an error message is generated at the block 937 and the routine ends. If an ultrasound fault has not occurred, then one of numerous other recoverable errors is assumed. Such errors may include the plunger motor being out of position, or the plunger or valve motor not responding. With such error, control proceeds to a block 945 which repositions the mechanism to the "home" position and tests the mechanism, as done at the block 1032 of FIG. 36K, discussed above. A decision block 946 determines if the repositioning is successful. If not, then control proceeds to the block 937. If so, then the recovery count is incremented at a block 947 and the routine ends.

The fault recovery routine is operable to respond to an error signal indicating error from which the pump driving mechanism can recovery by repositioning the pump driving mechanism to a preselect neutral position prior to continuation of an infusion pumping sequence.

Thus, in accordance with the invention there is illustrated a medical ambulatory infusion pump which accurately and safely administers a wide range of infusion rates.

We claim:

1. An air detecting apparatus for a liquid pump, the liquid pump comprising a liquid conveying conduit including a pump chamber portion, an inlet portion and an outlet portion, a plunger and inlet and outlet valves operatively associated with the pump chamber, inlet and outlet portions of the conduit, means for selectively actuating the plunger, inlet and outlet valves in a continuous series of pump chamber portion discharge and refill cycles, the selectively actuating means extending and retracting the plunger in incremental segments such that each incremental segment produces an essentially equal discharge or refill volume of the pump chamber segment, the air detect apparatus comprising:

an ultrasonic sound generator and an ultrasonic receiver spaced from one another to receive a detection portion of the liquid conveying conduit having a select volume greater than the volume of the pump chamber incremental segment, the detection portion being upstream of the inlet portion, and the ultrasonic receiver including means for determining whether the sound received from the generator is indicative of air or liquid within the detection portion of the conduit and means for out-putting an air signal when air is indicated;

means for actuating the ultrasonic sound generator after each incremental retraction of the plunger; and an electronic control receiving any air signals from the receiver, the electronic control including means for continuously summing the air signals over each refill cycle to determine whether the sum of air signals during the refill cycle exceeds a first select number and means for outputting an alarm signal if the first select number is exceeded.

2. The air detecting apparatus of claim 1 wherein the electronic control further comprises means for determining whether the sum of air signals in any two consecutive refill cycles exceeds a second select number, the alarm out-putting means out-putting an alarm signal if the second select number is exceeded.

3. An apparatus for detecting an excessive concentration of air in a liquid flow through a conduit the apparatus comprising:

an ultrasonic sound generator and an ultrasonic receiver spaced from one another to receive a detection portion of a liquid conveying conduit defining a first select volume therebetween, the ultrasonic receiver including means for determining whether the sound received from the generator is indicative of air or liquid within the first select volume and outputting an air signal if air is indicated;

means for actuating the ultrasonic sound generator to generate a sound upon a second select incremental volume of air or liquid less than the first select volume entering the detection portion and an equal incremental volume of air or liquid leaving the first select volume of the detection portion;

an electronic control receiving the air signal from the receiver, the electronic control including means for summing the air signals over a third select volume passing through the detecting portion to determine whether the sum of air signals in the third select volume exceeds a first select number and means for outputting an alarm signal if the first select number is exceeded.

4. The apparatus of claim 3 wherein the electronic control further comprises means for determining whether the sum of air signals in two consecutive third select volumes exceeds a second select number, the alarm outputting means outputting an alarm signal if the second select number is exceeded.

5. The apparatus of claim 3 wherein the second select incremental volume is about 5 microliters.

6. The apparatus of claim 3 wherein the third select volume of liquid is about 125 microliters.

* * * * *